United States Patent
Ratan et al.

(10) Patent No.: US 9,200,046 B2
(45) Date of Patent: Dec. 1, 2015

(54) REPORTER SYSTEM FOR HIGH THROUGHPUT SCREENING OF COMPOUNDS AND USES THEREOF

(75) Inventors: Rajiv Ratan, Scarsdale, NY (US); Irina Gazaryan, White Plains, NY (US); Natalya A. Smirnova, White Plains, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/538,418

(22) Filed: Jun. 29, 2012

(65) Prior Publication Data

US 2013/0005666 A1    Jan. 3, 2013

Related U.S. Application Data

(60) Provisional application No. 61/502,600, filed on Jun. 29, 2011.

(51) Int. Cl.

| | |
|---|---|
| *C12N 15/63* | (2006.01) |
| *C07K 19/00* | (2006.01) |
| *C12N 9/02* | (2006.01) |
| *C12N 9/38* | (2006.01) |
| *C12N 5/10* | (2006.01) |
| *C12N 5/071* | (2010.01) |
| *C40B 30/06* | (2006.01) |
| *A61K 31/519* | (2006.01) |
| *A61K 31/473* | (2006.01) |
| *A61K 31/4184* | (2006.01) |
| *A61K 31/423* | (2006.01) |
| *A61K 31/365* | (2006.01) |
| *C07K 14/47* | (2006.01) |
| *C12Q 1/37* | (2006.01) |
| *C12Q 1/66* | (2006.01) |
| *G01N 33/50* | (2006.01) |
| *A61K 31/4745* | (2006.01) |
| *A61K 31/496* | (2006.01) |
| *A61K 31/517* | (2006.01) |
| *A61K 31/52* | (2006.01) |
| *A61K 31/55* | (2006.01) |
| *A61K 31/704* | (2006.01) |
| *A61K 31/7076* | (2006.01) |
| *A61K 31/7084* | (2006.01) |
| *A61K 38/00* | (2006.01) |

(52) U.S. Cl.
CPC ........... *C07K 14/4705* (2013.01); *A61K 31/365* (2013.01); *A61K 31/4184* (2013.01); *A61K 31/423* (2013.01); *A61K 31/473* (2013.01); *A61K 31/4745* (2013.01); *A61K 31/496* (2013.01); *A61K 31/517* (2013.01); *A61K 31/519* (2013.01); *A61K 31/52* (2013.01); *A61K 31/55* (2013.01); *A61K 31/704* (2013.01); *A61K 31/7076* (2013.01); *A61K 31/7084* (2013.01); *C12Q 1/37* (2013.01); *C12Q 1/66* (2013.01); *G01N 33/5008* (2013.01); *G01N 33/5058* (2013.01); *A61K 38/00* (2013.01); *C07K 2319/61* (2013.01); *C07K 2319/73* (2013.01); *G01N 2800/285* (2013.01); *G01N 2800/2871* (2013.01); *G01N 2800/7009* (2013.01)

(58) Field of Classification Search
CPC ............ A61K 31/365; A61K 31/4184; A61K 31/423; A61K 31/473; A61K 31/4745; A61K 31/496; A61K 31/517; A61K 31/519; A61K 31/52; A61K 31/55; A61K 31/704; A61K 31/7076; A61K 31/7084; A61K 38/00; C07K 14/4705; C07K 2319/23; C12Q 1/37; C12Q 1/66; G01N 2800/285; G01N 2800/2871; G01N 2800/7009; G01N 33/5008; G01N 33/5058
USPC ........................................................ 514/21.1
See application file for complete search history.

(56) References Cited

U.S. PATENT DOCUMENTS

2008/0070299 A1*    3/2008    Wood et al. .................... 435/325

FOREIGN PATENT DOCUMENTS

GB              2464813 A         5/2010

OTHER PUBLICATIONS

Jung-Hwan Kim, Investigation of Novel NRF2 Partners, RAC3 and IQGAP1, Disseration submitted to Graduate School—New Brunswick, Rutgers University, 2009).*
NCBI GenBank (2008, Reference Sequence:NM_006164.2).*
Clontech Laboratories (pEFGP-C1 Vectpr Information, 1997, Protocol #PT3028-5).*
Vargas, M. R. et al., "Fibroblast Growth Factor-1 Induces Heme Oxygenase-1 via Nuclear Factor Erythroid 2-related Factor 2 (Nrf2) in Spinal Cord Astrocytes" J Biol Chem (2005) pp. 25571-25579, vol. 280, No. 27.
Vargas, M. R. et al., "Nrf2 Activation in Astrocytes Protects against Neurodegeneration in Mouse Models of Familial Amyotrophic Lateral Sclerosis" J Neurosci (Dec. 10, 2008) pp. 13574-13581, vol. 28, No. 50.

(Continued)

*Primary Examiner* — James H Alstrum Acevedo
*Assistant Examiner* — Erinne Dabkowski
(74) *Attorney, Agent, or Firm* — Scully, Scott, Murphy & Presser, P.C.

(57) ABSTRACT

The NF-E2-related factor 2 (Nrf2) is a key transcriptional regulator of antioxidant defense and detoxification. To directly monitor stabilization of Nrf2 we fused its Neh2 domain, responsible for the interaction with its nucleocytoplasmic regulator, Keap1, to firefly luciferase (Neh2-luciferase). It is shown herein that Neh2 domain is sufficient for recognition, ubiquitination and proteasomal degradation of Neh2-luciferase fusion protein. The novel Neh2-luc reporter system allows direct monitoring of the adaptive response to redox stress and classification of drugs based on the time-course of reporter activation. The novel reporter was used to screen a library of compounds to identify activators of Nrf2. The most robust and yet non toxic Nrf2 activators found— nordihydroguaiaretic acid, fisetin, and gedunin-induced astrocyte-dependent neuroprotection from oxidative stress via an Nrf2-dependent mechanism.

12 Claims, 35 Drawing Sheets

(56) References Cited

OTHER PUBLICATIONS

Wang, X. J. et al., "Activation of the NRF2 Signaling Pathway by Copper-Mediated Redox Cycling of Para- and Ortho-Hydroquinones" Chem Biol (Jan. 29, 2010) pp. 75-85, vol. 17.

Westerink, W. et al., "The development of RAD51C, Cystatin A, p53 and Nrf2 luciferase-reporter assays in metabolically competent HepG2 cells for the assessment of mechanism-based genotoxicity and of oxidative stress in the early research phase of drug development" Mutat Res (2010) pp. 21-40, vol. 696.

Wu, J. H. et al., "Identification and Characterization of Novel Nrf2 Inducers Designed to Target the Intervening Region of Keap1" Chem Biol Drug Des, (2010) pp. 475-480, vol. 75.

Yates, M. S. et al., "Pharmacodynamic characterization of chemopreventive triterpenoids as exceptionally potent inducers of Nrf2-regulated genes" Mol Cancer Ther (Jan. 2007) pp. 154-162, vol. 6, No. 1.

Yu, Y. et al., "Withaferin A targets heat shock protein 90 in pancreatic cancer cells" Biochem Pharmacol (2010) pp. 542-551, vol. 79.

Zhang, T. et al., "Characterization of Celastrol to Inhibit Hsp90 and Cdc37 Interaction" J Biol Chem (Dec. 18, 2009) pp. 35381-35389, vol. 284, No. 51.

Zhang, T. et al., "A novel Hsp90 inhibitor to disrupt Hsp90/Cdc37 complex against pancreatic cancer cells" Mol Cancer Ther (Jan. 2008) pp. 162-170, vol. 7, No. 1.

Zhang, D. D. et al., "Keap1 Is a Redox-Regulated Substrate Adaptor Protein for a Cul3-Dependent Ubiquitin Ligase Complex" Mol Cell Biol (Dec. 2004) pp. 10941-10953, vol. 24, No. 24.

Zhang, D. D., "Mechanistic Studies of the Nrf2-Keap1 Signaling Pathway" Drug Metab Rev (2006) pp. 769-789, vol. 38.

Zhu, H. et al., "Role of Nrf2 signaling in regulation of antioxidants and phase 2 enzymes in cardiac fibroblasts: Protection against reactive oxygen and nitrogen species-induced cell injury" FEBS Lett (2005) pp. 3029-3036, vol. 579.

Brandt, G. et al., "Gedunin, a Novel Hsp90 Inhibitor: Semisynthesis of Derivatives and Preliminary Structure—Activity Relationships" J Med Chem (Oct. 23, 2008) pp. 6495-6502, vol. 51, No. 20.

Brownlee, M., "Biochemistry and molecular cell biology of diabetic complications" Nature (Dec. 13, 2001) pp. 813-820, vol. 414.

Burton, N. C. et al., "In vivo Modulation of the Parkinsonian Phenotype by Nrf2" Neuro Toxicology (2006) pp. 1094-1100, vol. 27, No. 6.

Calabrese, V. et al., "Cellular Stress Response: A Novel Target for Chemoprevention and Nutritional Neuroprotection in Aging, Neurodegenerative Disorders and Longevity" Neurochem Res (2008) pp. 2444-2471, vol. 33.

Calkins, M.J. et al., "Protection from mitochondrial complex II inhibition in vitro and in vivo by Nrf2-mediated transcription" Proc Natl Acad Sci USA (Jan. 4, 2005) pp. 244-249, vol. 102, No. 1.

Chanas, S.A. et al., "Loss of the Nrf2 transcription factor causes a marked reduction in constitutive and inducible expression of the glutathione S-transferase Gsta1, Gsta2, Gstm1, Gstm2, Gstm3 and Gstm4 genes in the livers of male and female mice" J. Biochem (2002) pp. 405-416, vol. 365.

Chen, W. et al., "Direct Interaction between Nrf2 and p21Cip1/WAF1 Upregulates the Nrf2-Mediated Antioxidant Response" Mol Cell (Jun. 26, 2009) pp. 663-673, vol. 34.

Cho, H. et al., "Role of NRF2 in Protection Against Hyperoxic Lung Injury in Mice" Am J Respir Cell Mol Biol (2002) pp. 175-182, vol. 26.

Cullinan, S.B. et al., "The Keap1-BTB Protein Is an Adaptor That Bridges Nrf2 to a Cul3-Based E3 Ligase: Oxidative Stress Sensing by a Cul3-Keap1 Ligase" Mol Cell Biol (Oct. 2004) pp. 8477-8486, vol. 24, No. 19.

Dinkova-Kostova, A.T. et al., "Keap1, the Sensor for Electrophiles and Oxidants that Regulates the Phase 2 Response, Is a Zinc Metalloprotein" Biochemistry (2005) pp. 6889-6899, vol. 44.

Dinkova-Kostova, A. T. et al., "Chemical Structures of Inducers of Nicotinamide Quinone Oxidoreductase 1 (NQO1)" Methods Enzymol (2004) pp. 423-448, vol. 382.

Haskew-Layton, R. E. et al., "Controlled enzymatic production of astrocytic hydrogen peroxide protects neurons from oxidative stress via an Nrf2-independent pathway" Proc Natl Acad Sci USA (Oct. 5, 2010) pp. 17385-17390, vol. 107, No. 40.

Hayes, J. D. et al., "NRF2 and KEAP1 mutations: permanent activation of an adaptive response in cancer" Trends Biochem Sci (2009) pp. 176-188, vol. 34, No. 4.

Hur, W. et al., "A Small-Molecule Inducer of the Antioxidant Response Element" Chem Biol (May 28, 2010) pp. 537-547, vol. 17.

Ishii, Y. et al., "Transcription Factor Nrf2 Plays a Pivotal Role in Protection against Elastase-Induced Pulmonary Inflammation and Emphysema" J Immunol (2005) pp. 6968-6975, vol. 175.

Itoh, K. et al., "Keap1 represses nuclear activation of antioxidant responsive elements by Nrf2 through binding to the amino-terminal Neh2 domain" Genes Dev (1999) pp. 76-86, vol. 13.

Itoh, K. et al., "Transcription Factor Nrf2 Regulates Inflammation by Mediating the Effect of 15-Deoxy-Δ12,14- Prostaglandin J2" Mol Cell Biol (Jan. 2004) pp. 36-45, vol. 24, No. 1.

Jain, A. K. et al., "Phosphorylation and Dephosphorylation of Tyrosine 141 Regulate Stability and Degradation of INrf2" J Biol Chem (Jun. 20, 2008) pp. 17712-17720, vol. 283, No. 25.

Kahn, N. W. et al., "Proteasomal dysfunction activates the transcription factor SKN-1 and produces a selective oxidative-stress response in *Caenorhabditis elegans*" J. Biochem (2008) pp. 205-213, vol. 409.

Kandinov, B. et al., "Smoking and tea consumption delay onset of Parkinson's disease" Parkinsonism and Related Disorders (2009) pp. 41-46, vol. 15.

Kaspar, J. W. et al., "Nrf2:INrf2 (Keap1) signaling in oxidative stress" Free Radic Biol Med (2009) pp. 1304-1309, vol. 47.

Kataoka, K. et al., "Induction of Cellular Antioxidative Stress Genes through Heterodimeric Transcription Factor Nrf2/Small Maf by Antirheumatic Gold(I) Compounds" J Biol Chem (2001) pp. 34074-34081, vol. 276, No. 36.

Katoh, Y. el al., "Evolutionary conserved N-terminal domain of Nrf2 is essential for the Keap1-mediated degradation of the protein by proteasome" Arch Biochm Biophys (2005) pp. 342-350, vol. 433.

Kobayashi, A. et al., "Oxidative Stress Sensor Keap1 Functions as an Adaptor for Cul3-Based E3 Ligase to Regulate Proteasomal Degradation of Nrf2" Mol Cell Biol (Aug. 2004) pp. 7130-7139, vol. 24, No. 16.

Kuang, X. et al., "Attenuation of oxidative stress, inflammation and apoptosis by minocycline prevents retrovirus-induced neurodegeneration in mice" Brain Res (2009) pp. 174-184, vol. 1286.

Kwak, M. et al., "Modulation of Gene Expression by Cancer Chemopreventive Dithiolethiones through the Keap1-Nrf2 Pathway" J Biol Chem (2003) pp. 8135-8145, vol. 278, No. 10.

Kwak, M. et al., "Role of Transcription Factor Nrf2 in the Induction of Hepatic Phase 2 and Antioxidative Enzymes in vivo by the Cancer Chemoprotective Agent, 3H-1, 2-Dithiole-3-thione" Mol Med (2001) pp. 135-145, vol. 7, No. 2.

Lapouge, C. et al., "Spectroscopic and Theoretical Studies of the Zn(II) Chelation with Hydroxyflavones" J Phys Chem A (2006) pp. 12494-12500, vol. 110.

Lau, A. et al., "Dual roles of Nrf2 in cancer" Pharmacol Res (2008) pp. 262-270, vol. 58.

McMahon, M. et al., "The Cap 'n' Collar Basic Leucine Zipper Transcription Factor Nrf2 (NF-E2 p45-related Factor 2) Controls Both Constitutive and Inducible Expression of Intestinal Detoxification and Glutathione Biosynthetic Enzymes" Cancer Research (Apr. 15, 2001) pp. 3299-3307, vol. 61.

Moi, P. et al., "Isolation of NF-E2-related factor 2 (Nrf2), a NF-E2-like basic leucine zipper transcriptional activator that binds to the tandem NF-E2/AP1 repeat of the β-globin locus control region" Proc Natl Acad Sci USA (Oct. 1994) pp. 9926-9930, vol. 91.

Motohashi, H. et al., "Nrf2—Keap1 defines a physiologically important stress response mechanism" Trends Mol Med (Nov. 2004) pp. 549-557, vol. 10, No. 11.

Myzak, M. C. et al.,"Chemoprotection by sulforaphane: Keep one eye beyond Keap1" Cancer Lett (2006) pp. 208-218, vol. 233.

Obermann, W. et al., "In Vivo Function of Hsp90 Is Dependent on ATP Binding and ATP Hydrolysis" J Cell Biol (Nov. 16, 1998) pp. 901-910, vol. 143.

(56) References Cited

OTHER PUBLICATIONS

Ramos-Gomez, M. et al., "Sensitivity to carcinogenesis is increased and chemoprotective efficacy of enzyme inducers is lost in nrf2 transcription factor-deficient mice" Proc Natl Acad Sci USA (Mar. 13, 2001) pp. 3410-3415, vol. 98, No. 6.

Rangasamy, T. et al., "Disruption of Nrf2 enhances susceptibility to severe airway inflammation and asthma in mice" J Exp Med (Jul. 2005) pp. 47-59, vol. 202, No. 1.

Safran, M. et al., "Mouse model for noninvasive imaging of HIF prolyl hydroxylase activity: Assessment of an oral agent that stimulates erythropoietin production" Proc Natl Acad Sci USA (Jan. 3, 2006) pp. 105-110, vol. 103, No. 1.

Tong, K. I. et al., "Different Electrostatic Potentials Define ETGE and DLG Motifs as Hinge and Latch in Oxidative Stress Response" Mol Cell Biol. (Nov. 2007) pp. 7511-7521, vol. 27, No. 21.

Shih, A. et al., "Coordinate Regulation of Glutathione Biosynthesis and Release by Nrf2-Expressing Glia Potently Protects Neurons from Oxidative Stress" J Neurosci (Apr. 15, 2003) pp. 3394-3406, vol. 23, No. 8.

Shih, A. et al., "A Small-Molecule-Inducible Nrf2-Mediated Antioxidant Response Provides Effective Prophylaxis against Cerebral Ischemia In Vivo" J Neurosci (Nov. 2, 2005) pp. 10321-10335, vol. 25, No. 44.

Smirnova, N. A. et al., "Utilization of an In Vivo Reporter for High Throughput identification of Branched Small Molecule Regulators of Hypoxic Adaptation" Chem Biol (Apr. 23, 2010) pp. 380-391, vol. 17.

Smirnova, N. A. et al., "Development of Neh2-Luciferase Reporter and Its Application for High Throughput Screening and Real-Time Monitoring of Nrf2 Activators" Chem Biol (Jun. 24, 2011) pp. 752-765, vol. 18.

Son, T. G. et al., "Plumbagin, a noel Nrf2/ARE activator, protects against cerebral ischemia" J Neurochem (2010) pp. 1316-1326, vol. 112.

Stack, C. et al., "Triterpenoids CDDO-ethyl amide and CDDO-trifluoroethyl amide improve the behavioral phenotype and brain pathology in a transgenic mouse model of Huntington's disease" Free Radic Biol Med. (2010) pp. 147-158, vol. 49.

Theodore, M. et al., "Multiple Nuclear Localization Signals Function in the Nuclear Import of the Transcription Factor Nrf2" J Biol Chem (Apr. 4, 2008) pp. 8984-8994, vol. 283, No. 14.

Thimmulappa, R. K. et al., "Identification of Nrf2-regulated Genes Induced by the Chemopreventive Agent Sulforaphane by Oligonucleotide Microarray" Cancer Res (Sep. 15, 2002) pp. 5196-5203, vol. 62.

Tong, K. I. et al., "Two-site substrate recognition model for the Keap1-Nrf2 system: a hinge and latch mechanism" Biol Chem (Oct./Nov. 2006) pp. 1311-1320, vol. 387.

Tong, K. I. et al., "Keap1 Recruits Neh2 through Binding to ETGE and DLG Motifs: Characterization of the Two-Site Molecular Recognition Model" Mol Cell Biol (Apr. 2006) pp. 2887-2900, vol. 26, No. 8.

\* cited by examiner

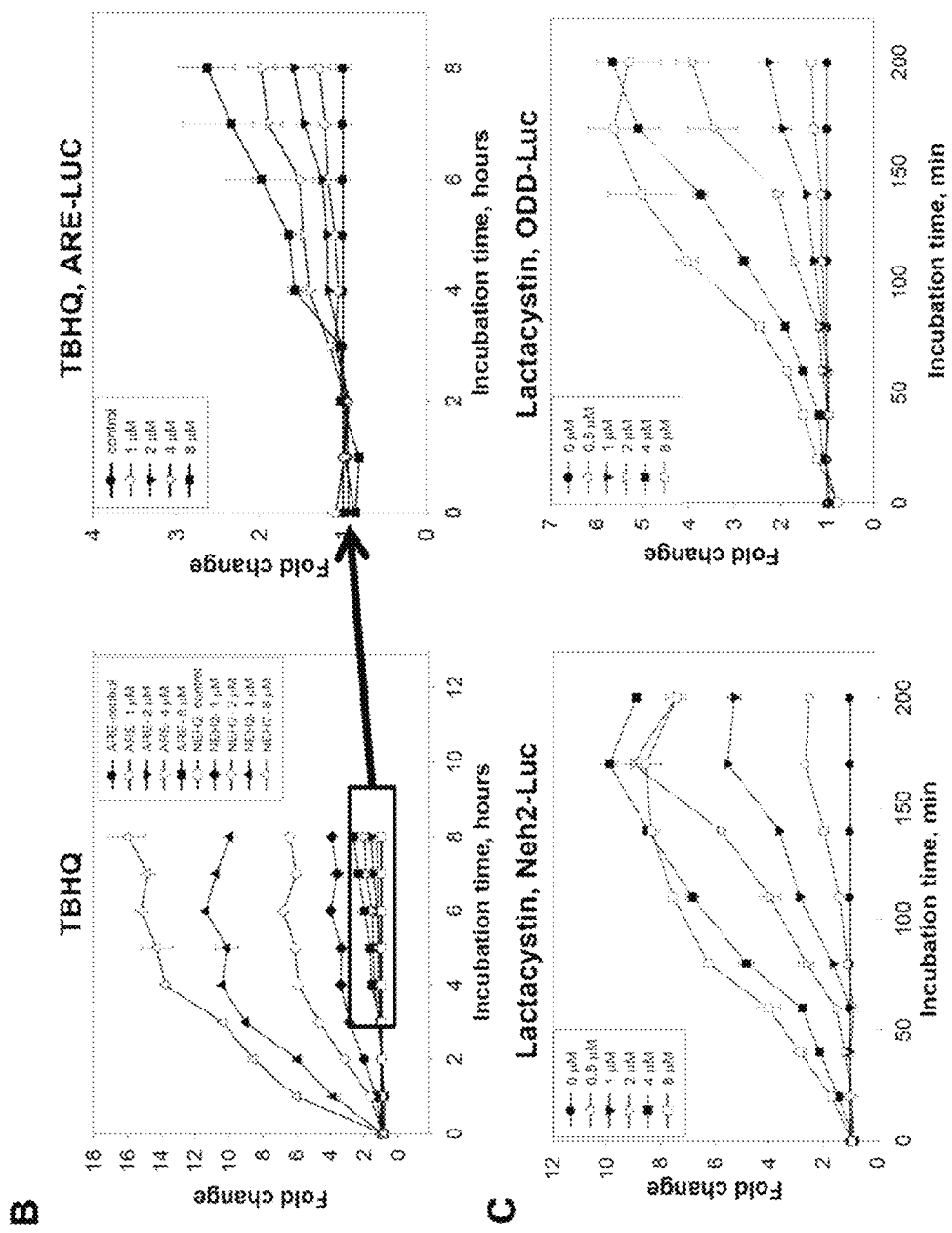
FIGURES 1B-C

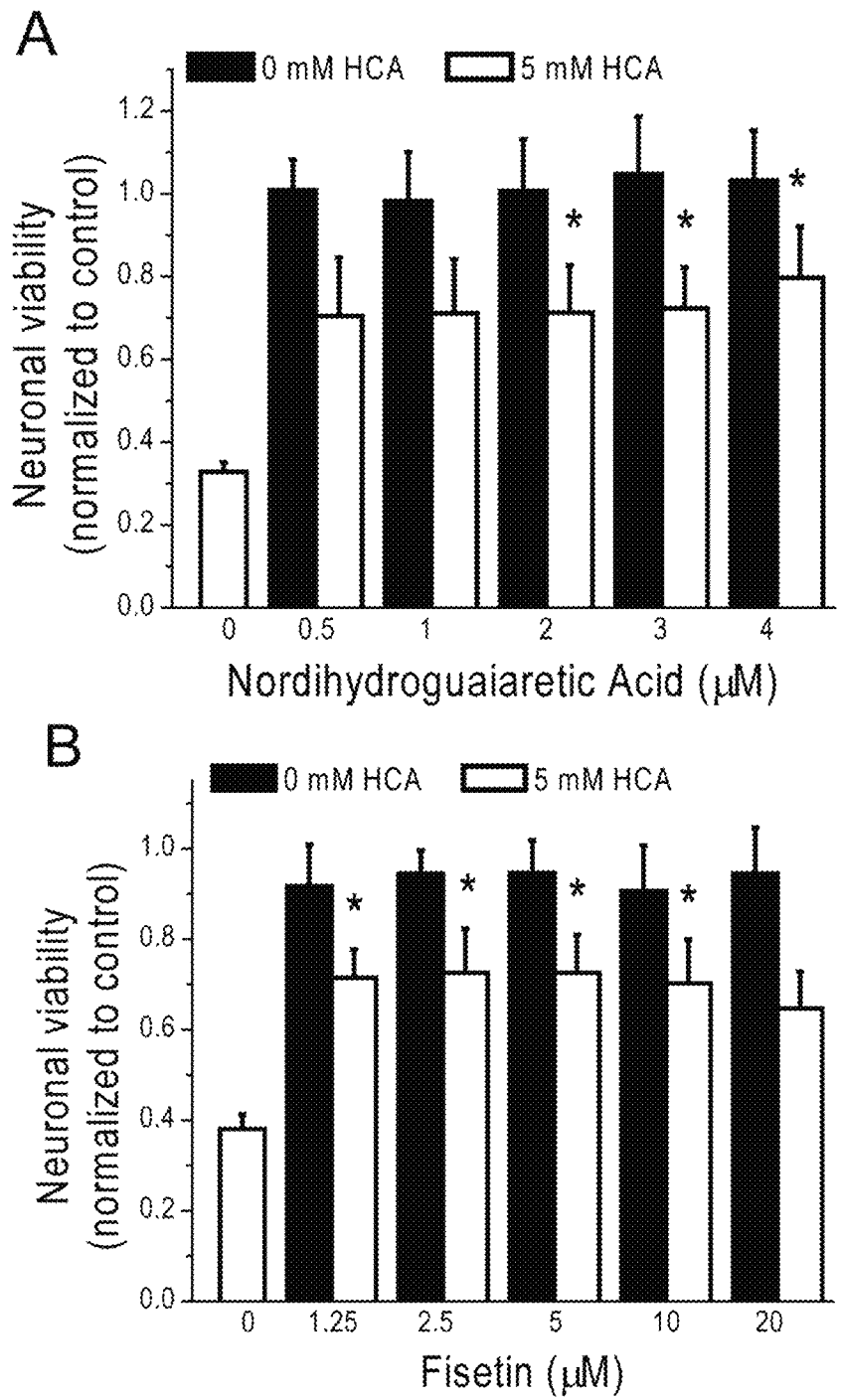
FIGURES 6A-B

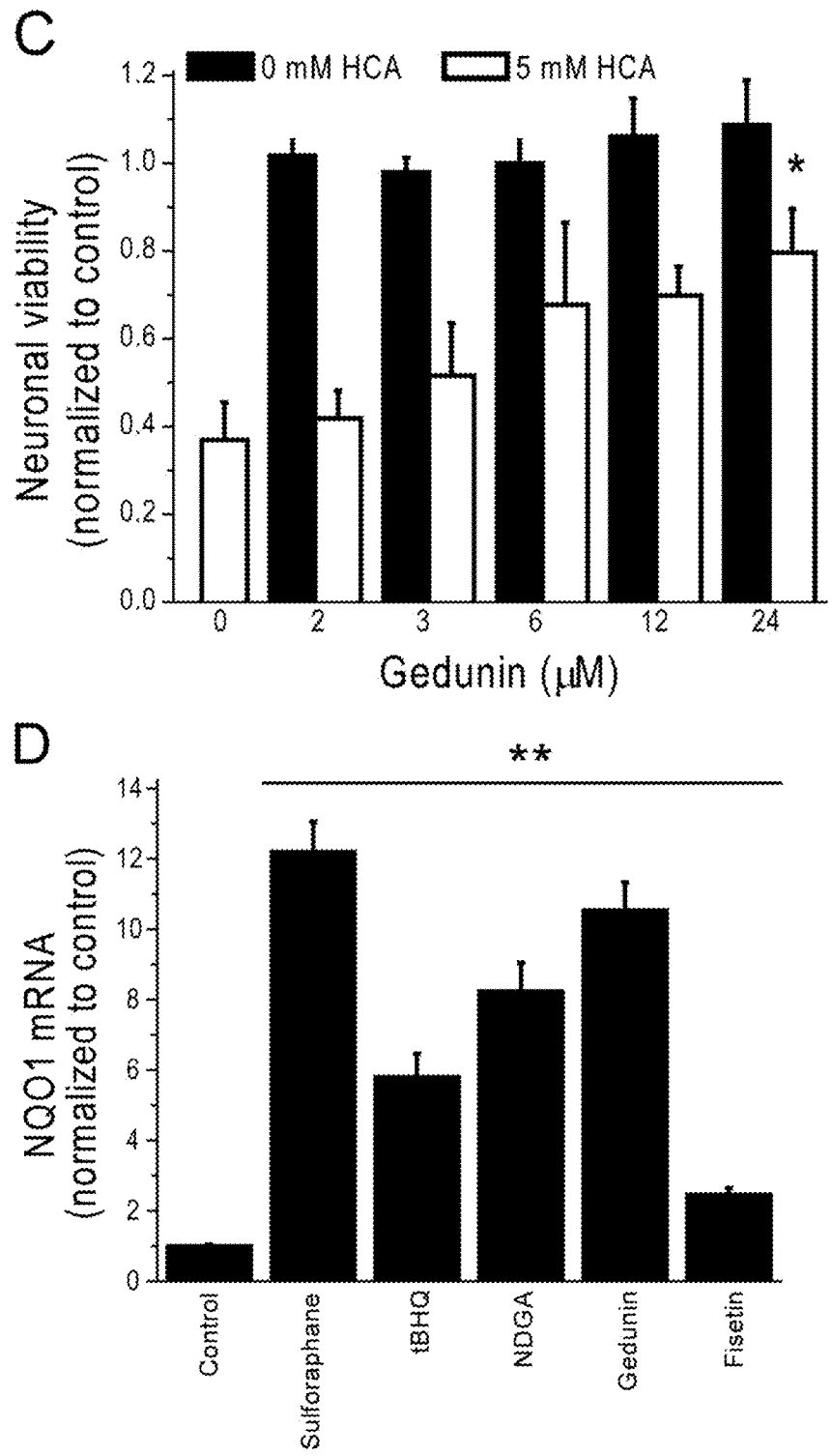
FIGURES 6C-D

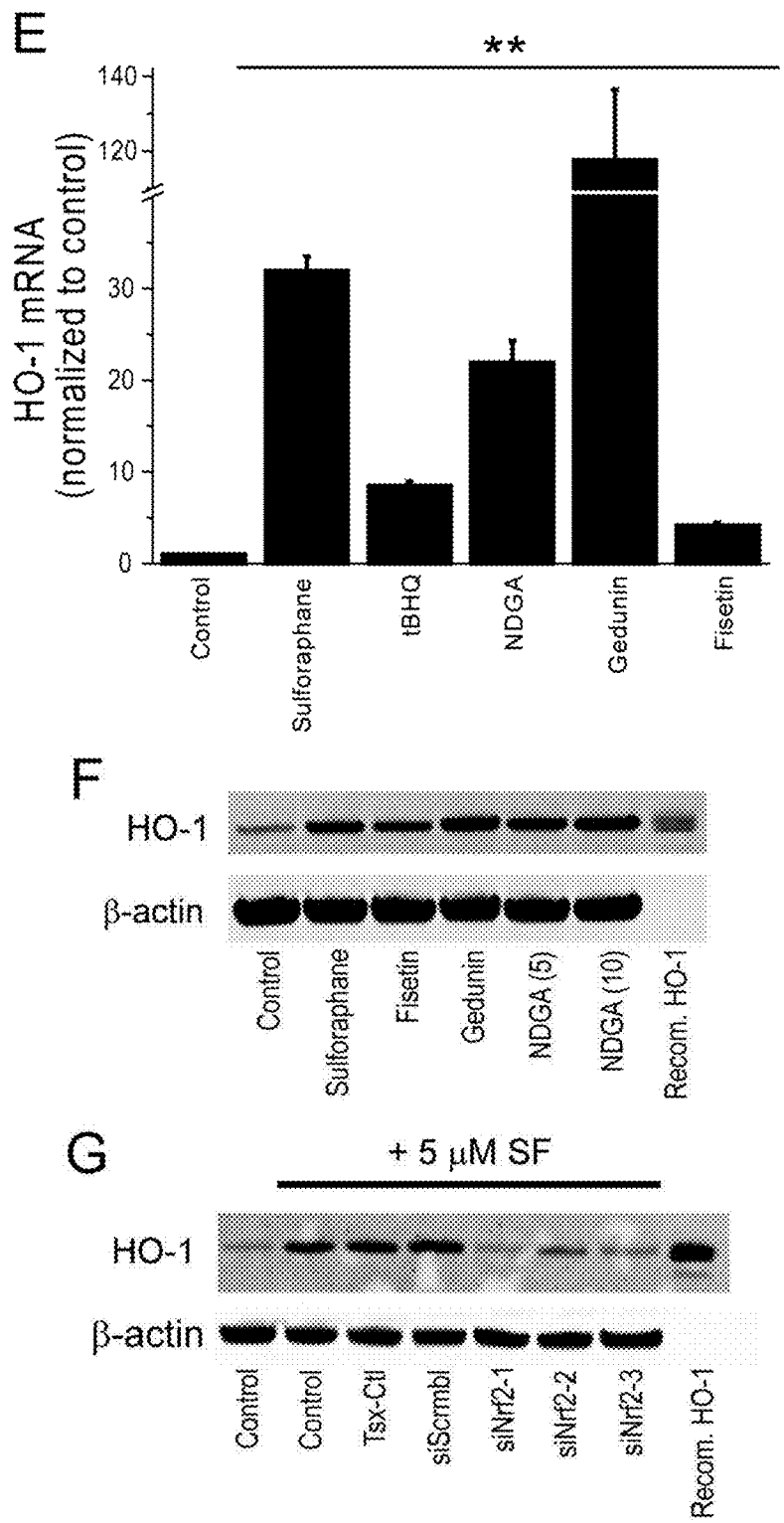
FIGURES 6E-G

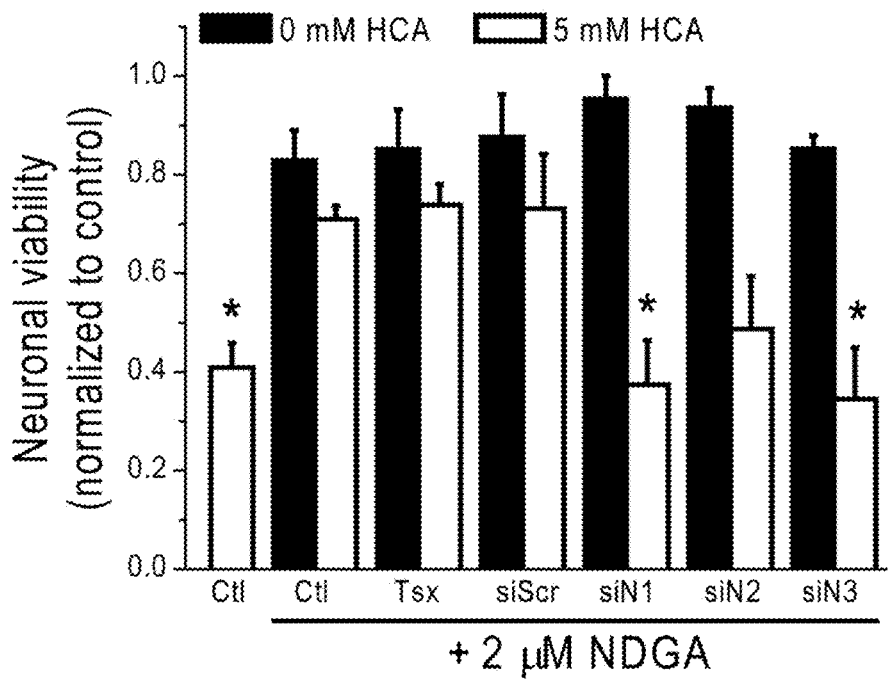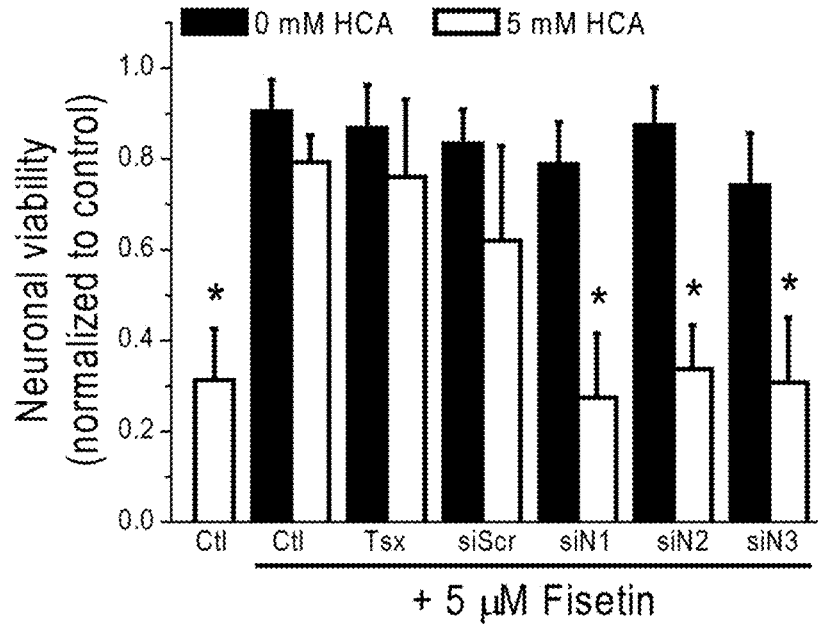
FIGURES 6H-I

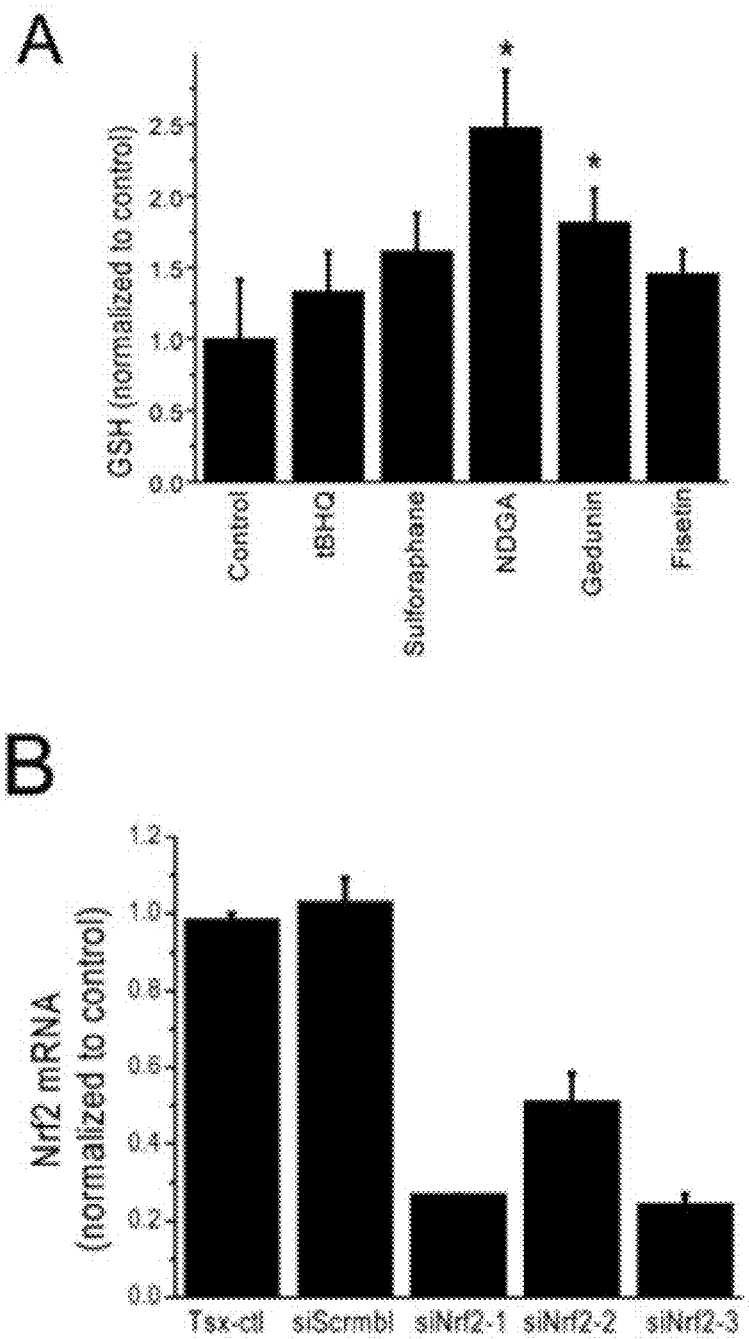
FIGURES 13A-B

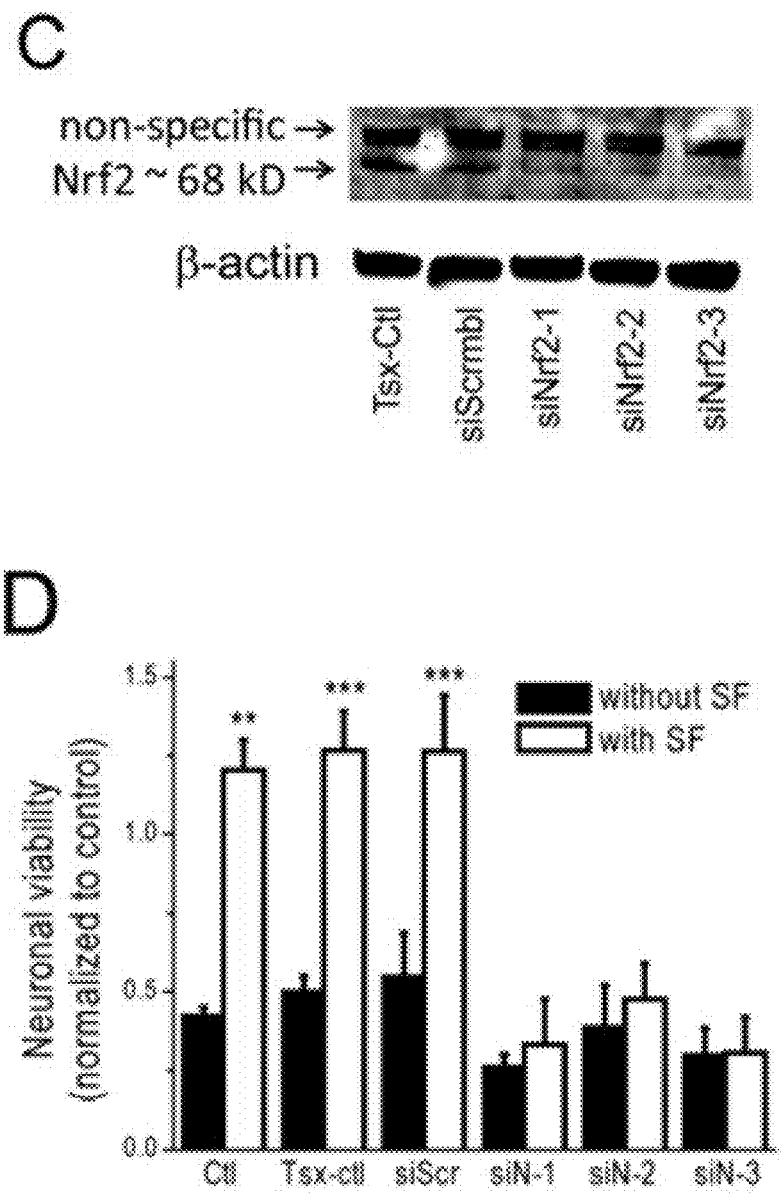
FIGURES 13C-D

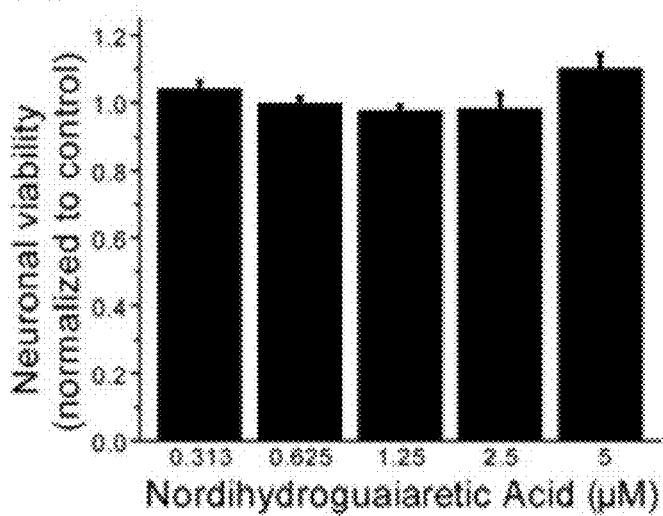
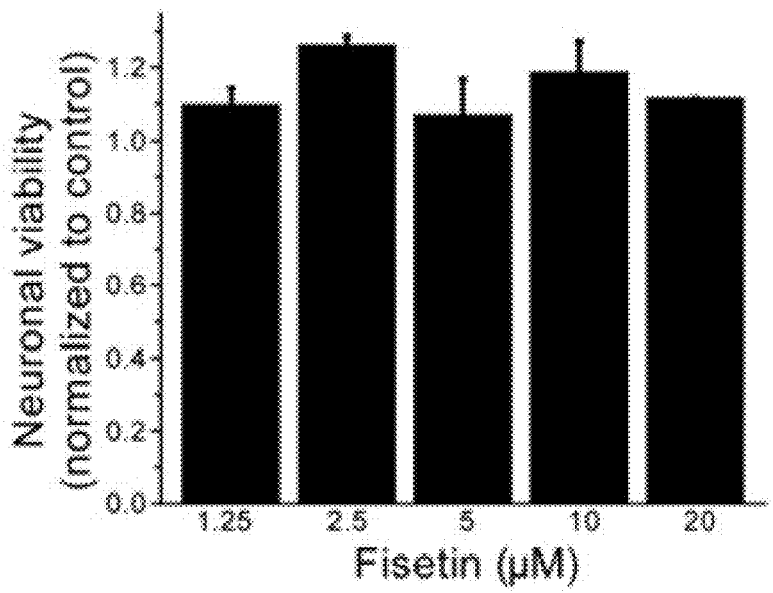
FIGURES 13E-F

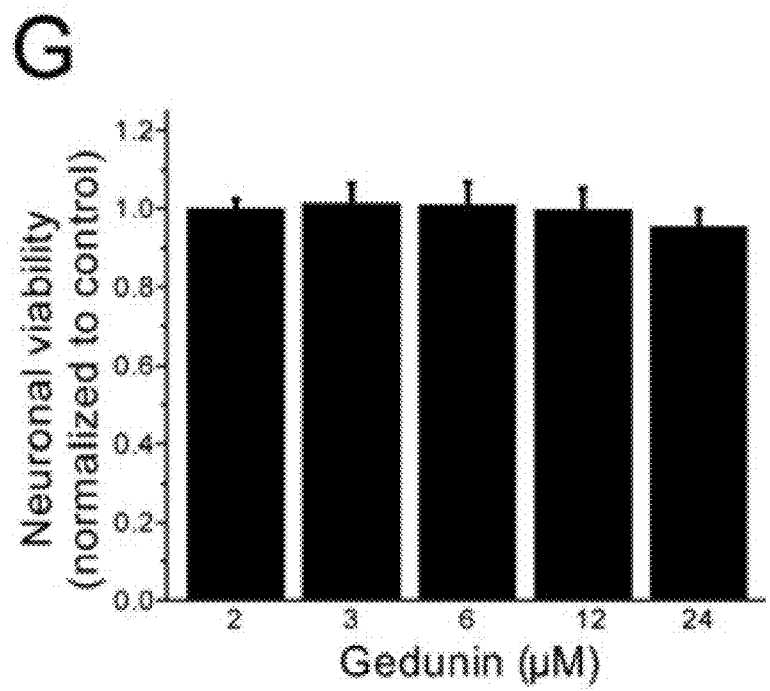
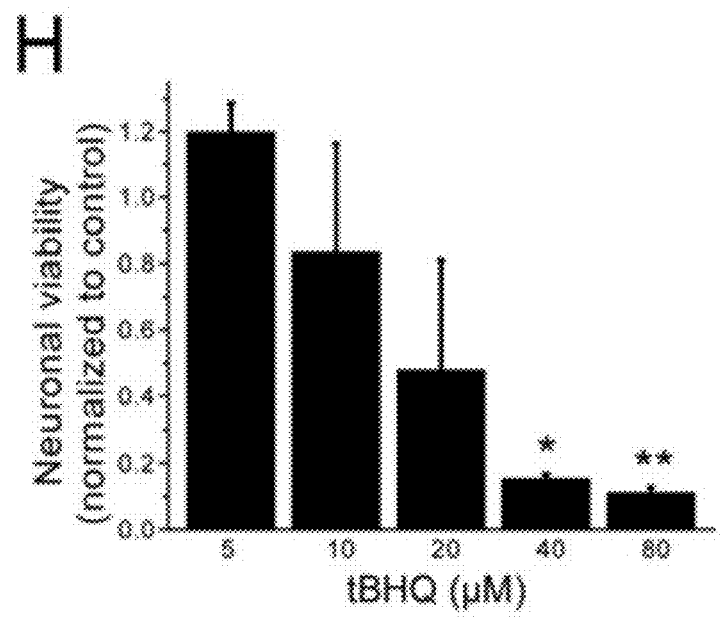
FIGURES 13G-H

SEQUENCE LISTING

<160> NUMBER OF SEQ ID NOS: 17

<210> SEQ ID NO 1

-continued

```
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 1
cccaagcttg gatccgaatt cgccaccatg atggacttgg agctgccgcc gcc    53

<210> SEQ ID NO 2
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 2
tagaatggcg ccgggccttt ctttatgttt ttggcgtctt cactggtttc tga    53

<210> SEQ ID NO 3
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 3
ctcagccttc caaatcgcag tcacagtgac tcagcagaat c                  41

<210> SEQ ID NO 4
<211> LENGTH: 1863
<212> TYPE: DNA
<213> ORGANISM: Homo sapiens

<400> SEQUENCE: 4
gacttggagc tgccgccgcc gggactcccg tcccagcagg acatggattt gattgacata    60
ctttggaggc aagatataga tcttggagta agtcgagaag tatttgactt cagtcagcga   120
cggaaagagt atgagctgga aaaacagaaa aaacttgaaa aggaaagaca agaacaactc   180
caaaaggagc aagagaaagc ttttttcgct cagttacaac tagatgaaga gacaggtgaa   240
tttctcccaa ttcagccagc ccagcacatc cagtcagaaa ccagtggatc tgccaactac   300
tcccaggttg cccacattcc caaatcagat gctttgtact tgatgactg catgcagctt   360 ttggcgcaga cattcccgtt tgtagatgac aatgaggttt cttcggctac gtttcagtca   420
cttgttcctg atattcccgg tcacatcgag agcccagtct tcattgctac taatcaggct   480
cagtcacctg aaacttctgt tgctcaggta gcccctgttg atttagacgg tatgcaacag   540
gacattgagc aagtttggga gcagggccgc cgtcggggag ccccaacaca cggtccacag   600
ctcatcatga tggagctatt atccattcct gagttacagt gtcttaatat tgaaaatgac   660
aagctggttg agactaccat ggttccaagt ccagaagcca aactgacaga agttgacaat   720
tatcattttt actcatctat accctcaatg gaaaaagaag taggtaactg tagtccacat   780
tttcttaatg cttttgagga ttccttcagc agcatcctct ccacagaaga ccccaaccag   840
ttgacagtga actcattaaa ttcagatgcc acagtcaaca cagattttgg tgatgaattt   900
tattctgctt tcatagctga gcccagtatc agcaacagca tgccctcacc tgctacttta   960
agccattcac tctctgaact tctaaatggg cccattgatg tttctgatct atcactttgc  1020
aaagctttca accaaaacca ccctgaaagc acagcagaat caatgattc tgactccggc  1080 atttcactaa acacaagtcc cagtgtggca tcaccagaac actcagtgga atcttccagc  1140
```

-continued

```
tatggagaca cactacttgg cctcagtgat tctgaagtgg aagagctaga tagtgcccct    1200
ggaagtgtca acagaatgg tcctaaaaca ccagtacatt cttctgggga tatggtacaa     1260
cccttgtcac catctcaggg gcagagcact cacgtgcatg atgcccaatg tgagaacaca    1320
ccagagaaag aattgcctgt aagtcctggt catcggaaaa ccccattcac aaaagacaaa    1380
cattcaagcc gcttggaggc tcatctcaca agagatgaac ttagggcaaa agctctccat    1440
atcccattcc ctgtagaaaa aatcattaac ctccctgttg ttgacttcaa cgaaatgatg    1500
tccaaagagc agttcaatga agctcaactt gcattaattc gggatatacg taggaggggt    1560
aagaataaag tggctgctca gaattgcaga aaaagaaaac tggaaaatat agtagaacta    1620
gagcaagatt tagatcattt gaaagatgaa aaagaaaaat tgctcaaaga aaaggagaa     1680 aatgacaaaa gccttcacct actgaaaaaa caactcagca ccttatatct cgaagttttc    1740
agcatgctac gtgatgaaga tggaaaacct tattctccta gtgaatactc cctgcagcaa    1800
acaagagatg gcaatgtttt ccttgttccc aaaagtaaga agccagatgt taagaaaaac    1860
tag                                                                 1863
```

<210> SEQ ID NO 5
<211> LENGTH: 620
<212> TYPE: PRT
<213> ORGANISM: Homo sapiens

<400> SEQUENCE: 5

```
Gln Gly Arg Arg Arg Gly Ala Pro Thr His Gly Pro Gln Leu Ile Met
1               5                   10                  15

Met Asp Leu Glu Leu Pro Pro Gly Leu Pro Ser Gln Gln Asp Met
            20                  25                  30

Asp Leu Ile Asp Ile Leu Trp Arg Gln Asp Ile Asp Leu Gly Val Ser
        35                  40                  45

Arg Glu Val Phe Asp Phe Ser Gln Arg Arg Lys Glu Tyr Glu Leu Glu
    50                  55                  60

Lys Gln Lys Lys Leu Glu Lys Glu Arg Gln Glu Gln Leu Gln Lys Glu
65                  70                  75                  80

Gln Glu Lys Ala Phe Phe Ala Gln Leu Gln Leu Asp Glu Glu Thr Gly
                85                  90                  95

Glu Phe Leu Pro Ile Gln Pro Ala Gln His Ile Gln Ser Glu Thr Ser
            100                 105                 110

Gly Ser Ala Asn Tyr Ser Gln Val Ala His Ile Pro Lys Ser Asp Ala
        115                 120                 125

Leu Tyr Phe Asp Asp Cys Met Gln Leu Leu Ala Gln Thr Phe Pro Phe
    130                 135                 140

Val Asp Asp Asn Glu Val Ser Ser Ala Thr Phe Gln Ser Leu Val Pro
145                 150                 155                 160

Asp Ile Pro Gly His Ile Glu Ser Pro Val Phe Ile Ala Thr Asn Gln
                165                 170                 175

Ala Gln Ser Pro Glu Thr Ser Val Ala Gln Val Ala Pro Val Asp Leu
            180                 185                 190

Asp Gly Met Gln Gln Asp Ile Glu Gln Val Trp Glu Glu Leu Leu Ser
        195                 200                 205

Ile Pro Glu Leu Gln Cys Leu Asn Ile Glu Asn Asp Lys Leu Val Glu
    210                 215                 220

Thr Thr Met Val Pro Ser Pro Glu Ala Lys Leu Thr Glu Val Asp Asn
225                 230                 235                 240
```

```
Tyr His Phe Tyr Ser Ser Ile Pro Ser Met Glu Lys Glu Val Gly Asn
                245                 250                 255

Cys Ser Pro His Phe Leu Asn Ala Phe Glu Asp Ser Phe Ser Ser Ile
            260                 265                 270

Leu Ser Thr Glu Asp Pro Asn Gln Leu Thr Val Asn Ser Leu Asn Ser
        275                 280                 285

Asp Ala Thr Val Asn Thr Asp Phe Gly Asp Glu Phe Tyr Ser Ala Phe
    290                 295                 300

Ile Ala Glu Pro Ser Ile Ser Asn Ser Met Pro Ser Pro Ala Thr Leu
305                 310                 315                 320

Ser His Ser Leu Ser Glu Leu Leu Asn Gly Pro Ile Asp Val Ser Asp
                325                 330                 335

Leu Ser Leu Cys Lys Ala Phe Asn Gln Asn His Pro Glu Ser Thr Ala
            340                 345                 350

Glu Phe Asn Asp Ser Asp Ser Gly Ile Ser Leu Asn Thr Ser Pro Ser
        355                 360                 365

Val Ala Ser Pro Glu His Ser Val Glu Ser Ser Tyr Gly Asp Thr
    370                 375                 380

Leu Leu Gly Leu Ser Asp Ser Glu Val Glu Glu Leu Asp Ser Ala Pro
385                 390                 395                 400

Gly Ser Val Lys Gln Asn Gly Pro Lys Thr Pro Val His Ser Ser Gly
                405                 410                 415

Asp Met Val Gln Pro Leu Ser Pro Ser Gln Gly Gln Ser Thr His Val
            420                 425                 430

His Asp Ala Gln Cys Glu Asn Thr Pro Glu Lys Glu Leu Pro Val Ser
        435                 440                 445

Pro Gly His Arg Lys Thr Pro Phe Thr Lys Asp Lys His Ser Ser Arg
    450                 455                 460

Leu Glu Ala His Leu Thr Arg Asp Glu Leu Arg Ala Lys Ala Leu His
465                 470                 475                 480

Ile Pro Phe Pro Val Glu Lys Ile Ile Asn Leu Pro Val Val Asp Phe
                485                 490                 495

Asn Glu Met Met Ser Lys Glu Gln Phe Asn Glu Ala Gln Leu Ala Leu
            500                 505                 510

Ile Arg Asp Ile Arg Arg Arg Gly Lys Asn Lys Val Ala Ala Gln Asn
        515                 520                 525

Cys Arg Lys Arg Lys Leu Glu Asn Ile Val Glu Leu Glu Gln Asp Leu
    530                 535                 540

Asp His Leu Lys Asp Glu Lys Glu Lys Leu Leu Lys Glu Lys Gly Glu
545                 550                 555                 560

Asn Asp Lys Ser Leu His Leu Leu Lys Lys Gln Leu Ser Thr Leu Tyr
                565                 570                 575

Leu Glu Val Phe Ser Met Leu Arg Asp Glu Asp Gly Lys Pro Tyr Ser
            580                 585                 590

Pro Ser Glu Tyr Ser Leu Gln Gln Thr Arg Asp Gly Asn Val Phe Leu
        595                 600                 605

Val Pro Lys Ser Lys Lys Pro Asp Val Lys Lys Asn
    610                 615                 620

<210> SEQ ID NO 6
<211> LENGTH: 605
<212> TYPE: PRT
<213> ORGANISM: Homo sapiens
```

<400> SEQUENCE: 6

Met Met Asp Leu Glu Leu Pro Pro Gly Leu Pro Ser Gln Gln Asp
1               5                   10                  15

Met Asp Leu Ile Asp Ile Leu Trp Arg Gln Asp Ile Asp Leu Gly
            20                  25                  30

Val Ser Arg Glu Val Phe Asp Phe Ser Gln Arg Arg Lys Glu Tyr
        35                  40                  45

Glu Leu Glu Lys Gln Lys Lys Leu Glu Lys Glu Arg Gln Glu Gln
    50                  55                  60

Leu Gln Lys Glu Gln Glu Lys Ala Phe Phe Ala Gln Leu Gln Leu
65                  70                  75                  80

Asp Glu Glu Thr Gly Glu Phe Leu Pro Ile Gln Pro Ala Gln His
                                85                  90

Ile Gln Ser Glu Thr Ser Gly Ser Ala Asn Tyr Ser Gln Val Ala
            95                  100                 105

His Ile Pro Lys Ser Asp Ala Leu Tyr Phe Asp Asp Cys Met Gln
        110                 115                 120

Leu Leu Ala Gln Thr Phe Pro Phe Val Asp Asp Asn Glu Val Ser
    125                 130                 135

Ser Ala Thr Phe Gln Ser Leu Val Pro Asp Ile Pro Gly His Ile
140                 145                 150

Glu Ser Pro Val Phe Ile Ala Thr Asn Gln Ala Gln Ser Pro Glu
            155                 160                 165

Thr Ser Val Ala Gln Val Ala Pro Val Asp Leu Asp Gly Met Gln
        170                 175                 180

Gln Asp Ile Glu Gln Val Trp Glu Glu Leu Leu Ser Ile Pro Glu
    185                 190                 195

Leu Gln Cys Leu Asn Ile Glu Asn Asp Lys Leu Val Glu Thr Thr
200                 205                 210

Met Val Pro Ser Pro Glu Ala Lys Leu Thr Glu Val Asp Asn Tyr
            215                 220                 225

His Phe Tyr Ser Ser Ile Pro Ser Met Glu Lys Glu Val Gly Asn
        230                 235                 240

Cys Ser Pro His Phe Leu Asn Ala Phe Glu Asp Ser Phe Ser Ser
    245                 250                 255

Ile Leu Ser Thr Glu Asp Pro Asn Gln Leu Thr Val Asn Ser Leu
260                 265                 270

Asn Ser Asp Ala Thr Val Asn Thr Asp Phe Gly Asp Glu Phe Tyr
            275                 280                 285

Ser Ala Phe Ile Ala Glu Pro Ser Ile Ser Asn Ser Met Pro Ser
        290                 295                 300

Pro Ala Thr Leu Ser His Ser Leu Ser Glu Leu Leu Asn Gly Pro
    305                 310                 315

Ile Asp Val Ser Asp Leu Ser Leu Cys Lys Ala Phe Asn Gln Asn
320                 325                 330

His Pro Glu Ser Thr Ala Glu Phe Asn Asp Ser Asp Ser Gly Ile
            335                 340                 345

Ser Leu Asn Thr Ser Pro Ser Val Ala Ser Pro Glu His Ser Val
        350                 355                 360

Glu Ser Ser Ser Tyr Gly Asp Thr Leu Leu Gly Leu Ser Asp Ser
    365                 370                 375

Glu Val Glu Leu Asp Ser Ala Pro Gly Ser Val Lys Gln Asn Gly
380                 385                 390

Pro Lys Thr Pro Val His Ser Ser Gly Asp Met Val Gln Pro Leu
            395                 400                 405

Ser Pro Ser Gln Gly Gln Ser Thr His
        410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
    530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Pro Asp Val Lys Lys Asn
        595                 600                 605

<210> SEQ ID NO 7
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 7

Met Asp Leu Ile Asp Ile Leu Trp Arg Gln Asp Ile Asp Leu Gly Val
1               5                   10                  15

Ser Arg Glu Val Phe Asp Phe Ser Gln Arg Arg Lys Glu Tyr Glu Leu
            20                  25                  30

Glu Lys Gln Lys Lys Leu Glu Lys Glu Arg Gln Glu Gln Leu Gln Lys
        35                  40                  45

Glu Gln Glu Lys Ala Phe Phe Thr Gln Leu Gln Leu
    50                  55                  60

<210> SEQ ID NO 8
<211> LENGTH: 73
<212> TYPE: PRT
<213> ORGANISM: Artificial Sequence
<220> FEATURE:
<223> OTHER INFORMATION: Synthetic Peptide

<400> SEQUENCE: 8

Met Asn Leu Ile Asp Ile Leu Trp Arg Gln Asp Ile Asp Leu Gly Ala
1               5                   10                  15

Arg Arg Glu Val Phe Asp Phe Ser Gln Arg Gln Lys Glu Tyr Glu Leu
            20                  25                  30

Glu Lys Gln Lys Lys Leu Glu Lys Glu Arg Gln Glu Gln Leu Gln Lys
        35                  40                  45

Glu Arg Glu Lys Ala Leu Leu Ala Gln Leu Val Leu Asp Glu Glu Thr

```
                50                  55                  60
Gly Glu Phe Val Pro Ala Gln Pro Ala
 65                  70

<210> SEQ ID NO 9
<211> LENGTH: 72
<212> TYPE: PRT
<213> ORGANISM: Artificial Sequence
<220> FEATURE:
<223> OTHER INFORMATION: Synthetic Peptide

<400> SEQUENCE: 9

Ile Asp Leu Ile Asp Ile Leu Trp Arg Gln Asp Ile Asp Leu Gly Ala
  1               5                  10                  15

Gly Arg Glu Val Phe Asp Tyr Ser His Arg Gln Lys Glu Gln Asp Val
                 20                  25                  30

Glu Lys Glu Leu Arg Asp Gly Gly Glu Gln Asp Thr Trp Ala Gly Glu
             35                  40                  45

Gly Ala Glu Ala Leu Ala Arg Asn Leu Leu Val Asp Gly Glu Thr Gly
         50                  55                  60

Glu Ser Phe Pro Ala Gln Phe Pro
 65                  70

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

Ile Asp Leu Ile Asp Val Leu Trp Arg Ser Asp Ile Ala Gly Glu Lys
  1               5                  10                  15

<210> SEQ ID NO 11
<211> LENGTH: 97
<212> TYPE: PRT
<213> ORGANISM: Artificial Sequence
<220> FEATURE:
<223> OTHER INFORMATION: Synthetic Peptide

<400> SEQUENCE: 11

Met Met Asp Leu Glu Leu Pro Pro Pro Gly Leu Pro Ser Gln Gln Asp
  1               5                  10                  15

Met Asp Leu Ile Asp Ile Leu Trp Arg Gln Asp Ile Asp Leu Gly Val
                 20                  25                  30

Ser Arg Glu Val Phe Asp Phe Ser Gln Arg Arg Lys Glu Tyr Glu Leu
             35                  40                  45

Glu Lys Gln Lys Lys Leu Glu Lys Glu Arg Gln Glu Gln Leu Gln Lys
         50                  55                  60

Glu Gln Glu Lys Ala Phe Phe Ala Gln Leu Gln Leu Asp Glu Glu Thr
 65                  70                  75                  80

Gly Glu Phe Leu Pro Ile Gln Pro Ala Gln His Ile Gln Ser Glu Thr
                 85                  90                  95

Ser

<210> SEQ ID NO 12
<211> LENGTH: 9
<212> TYPE: PRT
<213> ORGANISM: Artificial Sequence
<220> FEATURE:
```

-continued

```
<223> OTHER INFORMATION: Synthetic peptide (DLG motif)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Leu Xaa Xaa Gln Asp Xaa Asp Leu Gly
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Glu Thr Gly Glu
1

<210> SEQ ID NO 14
<211> LENGTH: 597
<212> TYPE: PRT
<213> ORGANISM: Mus musculus

<400> SEQUENCE: 14

Met Met Asp Leu Glu Leu Pro Pro Gly Leu Gln Ser Gln Gln Asp
1               5                   10                  15

Met Asp Leu Ile Asp Ile Leu Trp Arg Gln Asp Ile Asp Leu Gly Val
                20                  25                  30

Ser Arg Glu Val Phe Asp Phe Ser Gln Arg Gln Lys Asp Tyr Glu Leu
                35                  40                  45

Glu Lys Gln Lys Lys Leu Glu Lys Glu Arg Gln Glu Gln Leu Gln Lys
            50                  55                  60

Glu Gln Glu Lys Ala Phe Phe Ala Gln Phe Gln Leu Asp Glu Glu Thr
65                  70                  75                  80

Gly Glu Phe Leu Pro Ile Gln Pro Ala Gln His Ile Gln Thr Asp Thr
                85                  90                  95

Ser Gly Ser Ala Ser Tyr Ser Gln Val Ala His Ile Pro Lys Gln Asp
                100                 105                 110

Ala Leu Tyr Phe Glu Asp Cys Met Gln Leu Leu Ala Glu Thr Phe Pro
                115                 120                 125

Phe Val Asp Asp His Glu Ser Leu Ala Leu Asp Ile Pro Ser His Ala
            130                 135                 140

Glu Ser Ser Val Phe Thr Ala Pro His Gln Ala Gln Ser Leu Asn Ser
145                 150                 155                 160

Ser Leu Glu Ala Ala Met Thr Asp Leu Ser Ser Ile Gly Gln Asp Met
                165                 170                 175

Glu Gln Val Trp Gln Glu Leu Phe Ser Ile Pro Glu Leu Gln Cys Leu
                180                 185                 190

Asn Thr Glu Asn Lys Gln Leu Ala Asp Thr Thr Ala Val Pro Ser Pro
                195                 200                 205

Glu Ala Thr Leu Thr Glu Met Asp Ser Asn Tyr His Phe Tyr Ser Ser
                210                 215                 220

Ile Ser Ser Leu Glu Lys Glu Val Gly Asn Cys Gly Pro His Phe Leu
```

```
                225                 230                 235                 240
His Gly Phe Glu Asp Ser Phe Ser Ser Ile Leu Ser Thr Asp Ala
                245                 250                 255

Ser Gln Leu Thr Ser Leu Asp Ser Asn Pro Thr Leu Asn Thr Asp Phe
                260                 265                 270

Gly Asp Glu Phe Tyr Ser Ala Phe Ile Ala Glu Pro Ser Asp Gly Gly
                275                 280                 285

Ser Met Pro Ser Ser Ala Ala Ile Ser Gln Ser Leu Ser Glu Leu Leu
                290                 295                 300

Asp Gly Thr Ile Glu Gly Cys Asp Leu Ser Leu Cys Lys Ala Phe Asn
305                 310                 315                 320

Pro Lys His Ala Glu Gly Thr Met Glu Phe Asn Asp Ser Asp Ser Gly
                325                 330                 335

Ile Ser Leu Asn Thr Ser Pro Ser Arg Ala Ser Pro Glu His Ser Val
                340                 345                 350

Glu Ser Ser Ile Tyr Gly Asp Pro Pro Pro Gly Phe Ser Asp Ser Glu
                355                 360                 365

Met Glu Glu Leu Asp Ser Ala Pro Gly Ser Val Lys Gln Asn Gly Pro
                370                 375                 380

Lys Ala Gln Pro Ala His Ser Pro Gly Asp Thr Val Gln Pro Leu Ser
385                 390                 395                 400

Pro Ala Gln Gly His Ser Ala Pro Met Arg Glu Ser Gln Cys Glu Asn
                405                 410                 415

Thr Thr Lys Lys Glu Val Pro Val Ser Pro Gly His Gln Lys Ala Pro
                420                 425                 430

Phe Thr Lys Asp Lys His Ser Ser Arg Leu Glu Ala His Leu Thr Arg
                435                 440                 445

Asp Glu Leu Arg Ala Lys Ala Leu His Ile Pro Phe Pro Val Glu Lys
                450                 455                 460

Ile Ile Asn Leu Pro Val Asp Asp Phe Asn Glu Met Met Ser Lys Glu
465                 470                 475                 480

Gln Phe Asn Glu Ala Gln Leu Ala Leu Ile Arg Asp Ile Arg Arg Arg
                485                 490                 495

Gly Lys Asn Lys Val Ala Ala Gln Asn Cys Arg Lys Arg Lys Leu Glu
                500                 505                 510

Asn Ile Val Glu Leu Glu Gln Asp Leu Gly His Leu Lys Asp Glu Arg
                515                 520                 525

Glu Lys Leu Leu Arg Glu Lys Gly Glu Asn Asp Arg Asn Leu His Leu
                530                 535                 540

Leu Lys Arg Arg Leu Ser Thr Leu Tyr Leu Glu Val Phe Ser Met Leu
545                 550                 555                 560

Arg Asp Glu Asp Gly Lys Pro Tyr Ser Pro Ser Glu Tyr Ser Leu Gln
                565                 570                 575

Gln Thr Arg Asp Gly Asn Val Phe Leu Val Pro Lys Ser Lys Lys Pro
                580                 585                 590

Asp Thr Lys Lys Asn
                595

<210> SEQ ID NO 15
<211> LENGTH: 97
<212> TYPE: PRT
<213> ORGANISM: Artificial Sequence
<220> FEATURE:
<223> OTHER INFORMATION: synthetic peptide (mouse Neh2 domain)
```

```
<400> SEQUENCE: 15

Met Met Asp Leu Glu Leu Pro Pro Gly Leu Gln Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Gln Lys Asp Tyr Glu Leu
            35                  40                  45

Glu Lys Gln Lys Lys Leu Glu Lys Glu Arg Gln Glu Gln Leu Gln Lys
50                  55                  60

Glu Gln Glu Lys Ala Phe Phe Ala Gln Phe Gln Leu Asp Glu Glu Thr
65                  70                  75                  80

Gly Glu Phe Leu Pro Ile Gln Pro Ala Gln His Ile Gln Thr Asp Thr
                85                  90                  95

Ser

<210> SEQ ID NO 16
<211> LENGTH: 582
<212> TYPE: PRT
<213> ORGANISM: Gallus gallus

<400> SEQUENCE: 16

Met Asn Leu Ile Asp Ile Leu Trp Arg Gln Asp Ile Asp Leu Gly Ala
1               5                   10                  15

Arg Arg Glu Val Phe Asp Phe Ser Arg Gln Lys Glu Tyr Glu Leu
            20                  25                  30

Glu Lys Gln Lys Lys Leu Glu Lys Glu Arg Gln Glu Gln Leu Gln Lys
            35                  40                  45

Glu Arg Glu Lys Ala Leu Leu Ala Gln Leu Val Leu Asp Glu Glu Thr
50                  55                  60

Gly Glu Phe Val Pro Ala Gln Pro Ala Gln Arg Val Gln Ser Glu Asn
65                  70                  75                  80

Ala Glu Pro Pro Ile Ser Phe Ser Gln Ser Thr Asp Thr Ser Lys Pro
                85                  90                  95

Glu Glu Ala Leu Ser Phe Asp Asp Cys Met Gln Leu Leu Ala Glu Ala
            100                 105                 110

Phe Pro Phe Ile Asp Asp Asn Glu Ala Ser Pro Ala Ala Phe Gln Ser
            115                 120                 125

Leu Val Pro Asp Gln Ile Asp Ser Asp Pro Val Phe Ile Ser Ala Asn
130                 135                 140

Gln Thr Gln Pro Pro Ser Ser Pro Gly Ile Val Pro Leu Thr Asp Ala
145                 150                 155                 160

Glu Asn Met Gln Asn Ile Glu Gln Val Trp Glu Glu Leu Leu Ser Leu
                165                 170                 175

Pro Glu Leu Gln Cys Leu Asn Ile Glu Asn Asp Asn Leu Ala Glu Val
            180                 185                 190

Ser Thr Ile Thr Ser Pro Glu Thr Lys Pro Ala Glu Met His Asn Ser
            195                 200                 205

Tyr Asp Tyr Tyr Asn Ser Leu Pro Ile Met Arg Lys Asp Val Asn Cys
210                 215                 220

Gly Pro Asp Phe Leu Glu Asn Ile Glu Gly Phe Ser Ser Ile Leu
225                 230                 235                 240

Gln Pro Asp Asp Ser Ser Gln Leu Asn Val Asn Ser Leu Asn Asn Ser
                245                 250                 255

Leu Thr Leu Ser Ser Asp Phe Cys Glu Asp Phe Tyr Thr Asn Phe Ile
```

```
            260                 265                 270
Cys Ala Lys Gly Asp Gly Asp Thr Gly Thr Thr Asn Thr Ile Ser Gln
            275                 280                 285

Ser Leu Ala Asp Ile Leu Ser Glu Pro Ile Asp Leu Ser Asp Phe Pro
            290                 295                 300

Leu Trp Arg Ala Phe Asn Asp Asp His Ser Gly Thr Val Pro Glu Cys
305                 310                 315                 320

Asn Asp Ser Asp Ser Gly Ile Ser Leu Asn Ala Asn Ser Ser Ile Ala
                325                 330                 335

Ser Pro Glu His Ser Val Glu Ser Ser Thr Cys Gly Asp Lys Thr Phe
            340                 345                 350

Gly Cys Ser Asp Ser Glu Met Glu Asp Met Asp Ser Ser Pro Gly Ser
            355                 360                 365

Val Pro Gln Gly Asn Ala Ser Val Tyr Ser Ser Arg Phe Pro Asp Gln
            370                 375                 380

Val Leu Pro Ser Val Glu Pro Gly Thr Gln Thr Pro Ser Leu Gln Arg
385                 390                 395                 400

Met Asn Thr Pro Lys Lys Asp Pro Pro Ala Gly Pro Gly His Pro Lys
                405                 410                 415

Ala Pro Phe Thr Lys Asp Lys Pro Ser Gly Arg Leu Glu Ala His Leu
            420                 425                 430

Thr Arg Asp Glu Gln Arg Ala Lys Ala Leu Gln Ile Pro Phe Pro Val
            435                 440                 445

Glu Lys Ile Ile Asn Leu Pro Val Asp Asp Phe Asn Glu Met Met Ser
450                 455                 460

Lys Glu Gln Phe Ser Glu Ala Gln Leu Ala Leu Ile Arg Asp Ile Arg
465                 470                 475                 480

Arg Arg Gly Lys Asn Lys Val Ala Ala Gln Asn Cys Arg Lys Arg Lys
                485                 490                 495

Leu Glu Asn Ile Val Glu Leu Glu Gln Asp Leu Ser His Leu Lys Asp
            500                 505                 510

Glu Arg Glu Lys Leu Leu Lys Glu Lys Gly Glu Asn Asp Lys Ser Leu
            515                 520                 525

Arg Gln Met Lys Lys Gln Leu Thr Thr Leu Tyr Ile Glu Val Phe Ser
            530                 535                 540

Met Leu Arg Asp Glu Asp Gly Lys Ser Tyr Ser Pro Ser Glu Tyr Ser
545                 550                 555                 560

Leu Gln Gln Thr Arg Asp Gly Asn Ile Phe Leu Val Pro Lys Ser Arg
                565                 570                 575

Lys Ala Glu Thr Lys Leu
            580

<210> SEQ ID NO 17
<211> LENGTH: 94
<212> TYPE: PRT
<213> ORGANISM: Artificial Sequence
<220> FEATURE:
<223> OTHER INFORMATION: synthetic peptide (chicken Neh2 domain)

<400> SEQUENCE: 17

Met Asn Leu Ile Asp Ile Leu Trp Arg Gln Asp Ile Asp Leu Gly Ala
1               5                   10                  15

Arg Arg Glu Val Phe Asp Phe Ser Gln Arg Gln Lys Glu Tyr Glu Leu
            20                  25                  30

Glu Lys Gln Lys Lys Leu Glu Lys Glu Arg Gln Glu Gln Leu Gln Lys
```

-continued

```
            35                  40                  45
Glu Arg Glu Lys Ala Leu Leu Ala Gln Leu Val Leu Asp Glu Glu Thr
    50                  55                  60

Gly Glu Phe Val Pro Ala Gln Pro Ala Gln Arg Val Gln Ser Glu Asn
65                  70                  75                  80

Ala Glu Pro Pro Ile Ser Phe Ser Gln Ser Thr Asp Thr Ser
                85                  90
```

REPORTER SYSTEM FOR HIGH THROUGHPUT SCREENING OF COMPOUNDS AND USES THEREOF

CROSS REFERENCE TO RELATED APPLICATION

This application claims the benefit of priority from U.S. Provisional Application No. 61/502,600, filed Jun. 29, 2011, the entire contents of which are incorporated herein by reference.

GOVERNMENT FUNDING

This invention was made with Government support of the Winifred Masterson Burke Relief Foundation, the Adelson Foundation for Neurorehabilitation and Repair, NYS DOH Center of Research Excellence #CO19772, and Thomas Hartman Foundation for Parkinson's Research.

BACKGROUND

Oxidative stress is a major contributor to aging, insulin resistance, and neurodegeneration. An emergent strategy for restoring redox homeostasis involves activation of the transcription factor, Nrf2 (nuclear factor erythroid 2-related factor 2), a member of the cap'n'collar family of basic leucine zipper transcription factors that regulates a coordinated adaptive gene program (MOI et al., *Proc Natl Acad Sci USA*, 91: 9926-9930 (1994)). Indeed, activators of the Nrf2 response are beneficial for the treatment and prevention of chronic degenerative diseases, while inhibitors of its activation may help to fight cancer (CALABRESE et al., *Neurochem Res*, 33: 2444-2471 (2008); HAYES et al., *Trends Biochem Sci*, 34, 176-188 (2009); LAU et al., *Pharmacol Res*, 58: 262-270 (2008)). A major challenge in the development of effective Nrf2 activators is to identify those that lead specifically to Nrf2 stabilization and consequent promoter activation, without imposing general oxidative/electrophilic stress.

Nrf2 is sequestered under homeostatic conditions by binding to its inhibitory protein, Keap1 (Kelch-like ECH-associated protein-1) (MOTOHASHI et al., *Trends Mol Med*, 10: 549-557 (2004); ITOH et al., *Genes Dev* 13: 76-86 (1999)). Keap1 serves as a bridge between Nrf2 and the Cul3-Rbx1 E3 ubiquitin ligase, leading to Nrf2 ubiquitination and thereby targeting Nrf2 for degradation by the 26S proteasome (KOBAYASHI et al., *Mol Cell Biol*, 24: 7130-7139 (2004); CULLINAN et al., *Mol Cell Biol*, 24: 8477-8486 (2004); ZHANG et al., *Mol Cell Biol*, 24: 10941-10953 (2004)). Upon exposure to oxidative stress, xenobiotics, or electrophilic compounds, the Nrf2 protein is released from its complex with Keap1 and translocates to the nucleus. There, it forms heterodimers with other transcription regulators, such as small Maf proteins, and induces the expression of antioxidant genes controlled by the antioxidant response element (ARE) (KASPAR et al., *Free Radic Biol Med*, 47: 1304-1309 (2009)).

Nrf2 is composed of Neh1-Neh6 domains, among which Neh2 is the putative negative regulatory domain that interacts with Keap1, Neh4 and Neh5 are transactivation domains, and Neh1 is the binding domain for ARE (TONG et al., *Biol Chem*, 387: 1311-1320 (2006b)). The functional domains of Keap1 are the Broad complex, Tramtrack and Bric-a-Brac (BTB), the intervening region (IVR), the double glycine repeats domain (DGR), and the C-terminal region (CTR) (TONG et al., *Biol Chem*, 387: 1311-1320 (2006b)). Two motifs in the Neh2 domain, e.g. ETGE and DLG, are recognized by the Keap1 homodimer in a hinge-latch mode (TONG et al., *Mol Cell Biol*, 26: 2887-2900 (2006a); TONG et al., *Biol Chem*, 387: 1311-1320 (2006b); TONG et al., *Mol Cell Biol.*, 27: 7511-7521 (2007)). Keap1 mediates polyubiquitination of the positioned lysines within the central α-helix of the Neh2 domain under homeostatic conditions. Under oxidative/electrophilic stress reactive cysteines within Keap1 are modified and thus Keap1 undergoes conformational changes which lead to the detachment of the weak-binding DLG, resulting in Nrf2 stabilization. However, debate remains as to whether Nrf2 is completely released from its complex with Keap1 (ZHANG, Drug Metab Rev, 38: 769-789 (2006)) or not. Nrf2 activators identified so far are represented by potent alkylating agents (DINKOVA-KOSTOVA et al., *Methods Enzymol*, 382: 423-448 (2004)) and redox active compounds like diphenols, aminophenols and phenylene diamines, the precise mechanism of action of which is controversial. Recent data shows an enhanced effect of these compounds in the presence of exogenously added copper (WANG et al., *Chem Biol*, 17: 75-85 (2010)).

Current techniques for monitoring Nrf2 activation include the ARE-luciferase (MOEHLENKAMP et al., *Arch Biochem Biophys*, 363: 98-106 (1999)), Nrf2 responsive element-luciferase (Westerink et al., *Mutat Res* 696, 21-40 (2010)), or ARE-human placental alkaline phosphatase reporter systems (Son et al., *J Neurochem* 112, 1316-1326 (2010)).

Recently, a GFP fusion protein with the Nrf2 ZIP domain was utilized to study Nrf2 nuclear translocation (THEODORE et al., *J Biol Chem*, 283: 8984-8994 (2008)), while GFP fusion with the *C. elegans* Nrf2 analog was used to analyze Nrf2 activation by proteasomal dysfunction (KAHN et al., *J. Biochem*, 409: 205-213 (2008)). The ARE-GFP reporter assay was used to screen the library of 2,000 biologically active compounds (Spectrum library) and 45 hits identified (SHAW et al., *UK Patent Application* #0918626.3, Priority Date (Oct. 24, 2008), Publ Date (May 5, 2010)), with andrographolide being the most potent. The use of ARE-luciferase reporter for high throughput screening (HTS) purposes has been recently published (HUR et al., *Chem Biol*, 17, 537-547 (2010)). The screen of 1.5 million compounds resulted in discovery of novel alkylating agents targeting Cys 151 in Keap1 as well as a dozen other cellular proteins including phosphatase 2a, and HDAC1 and HDAC2 (HUR et al., *Chem Biol*, 17, 537-547 (2010)).

ITOH et al., *Genes Dev* 13: 76-86 (1999) disclosed a NEH2+ reporter construct, and used it to assay NRF2 activity. This paper describes a chicken Neh2 construct, and a mouse Neh2 construct. The latter is 1-73 aa residues of mouse Neh2 attached to GFP. As shown in FIG. 9 of that paper, the construct provides a very strong fluorescent signal, indicating that it is poorly recognized by endogenous Keap1 and therefore accumulates in the cell. The construct is not applicable for HTS purposes. Itoh et al. demonstrate that their fusion is ubiquitated (prepared for destruction) but they do not show that it is degraded. The reporter in Itoh et al is attached to the N terminus.

SUMMARY OF THE DISCLOSURE

This disclosure presents a novel reporter construct, in which the Neh2 domain is fused to a luciferase gene (Neh2-luc), as a new powerful tool for the high throughput screening and real time monitoring of Nrf2 activation. It is demonstrated herein that a 97 aa Neh2 sequence is sufficient for recognition, ubiquitination and degradation of the fusion where the reporter in attached to C-terminus of Neh2. This disclosure also demonstrates the utility of the Neh2-luc model to identify and classify novel compounds capable of inducing Nrf2-specific astrocyte-dependent neuroprotection from oxidative stress.

BRIEF DESCRIPTION OF THE DRAWINGS

FIG. 8. Supporting experiments to FIG. 1. The properties of New Neh2-Luc reporter. A: Neh2-Luc reporter competes with endogenous NRF2 for Keap1 binding and rescues endogenous NRF2 from degradation. SH-SY5Y cells carried Neh2-Luc reporter show increased transcription of NRF2-regulated genes such as NAD(P)H dehydrogenase (NQO1), heme oxygenase 1 (HO-1), and glutamate-cysteine ligase modifier subunit (GCL M). Data are the means of three independent experiments normalized to GAPDH control. B: Neh2-Luc reporter response to canonical Nrf2 activators-PGJ2, TBHQ, and sulforaphane after 4 hours incubation. Under the same conditions, ODD-Luc reporter line (SMIRNOVA et al., Chem Biol, 17: 380-391 (2010)) did not show increase in luciferase activity.

FIG. 12. Supporting to FIG. 5. Effect of hits on Keap1 labeling with sulforaphane analog, stabilization of Nrf2 in the nucleus and induction of Nrf2-regulated genes. A: structural formulas of the compounds used; B: competition with Keap1 labeling. HEK293 cells transiently expressing FLAG-Keap1 were incubated with 200 µM competing compounds (sulforaphane, fisetin, quercetin, gedunin, TBHQ, ciclopirox, geldanamycin) and then further incubated with 10 µM sulfoxythiocarbate-alkyne (STCA) for 30 min at 37° C. FLAG-Keap1 was immunoprecipitated from cell lysates, subjected to click reaction with biotin azide on beads, and eluted with SDS-loading buffer. Eluted samples were immunoblotted with Streptavidin-HRP (Pierce) and anti-FLAG antibodies: (1) control experiment showing Keap1 labeling with STCA and its almost complete inhibition in the presence of STCB; (2) classic Nrf2 activators sulforaphane and TBHQ behave differently—sulforaphane inhibits Keap1 labeling completely while TBHQ competes very poorly; (3) positive hits fisetin, NDGA and gedunin behave similar to TBHQ and poorly compete with Keap1 labeling; (4) negative controls geldanamycin (Hsp90 inhibitor) and ciclopirox (iron and Zn chelator) show no competition with Keap1 labeling. C: Elevated transcription of NRF2-regulated genes. Increase in transcription of heme oxygenase 1 (HO-1) and glutamate-cysteine ligase modifier subunit (GCL M) genes was observed upon 10 hours treatment of SHS5Y5 Neh2-Luc cells with TBHQ (10 µM), Sulforaphane (8 µM), Fisetin (5 µM), Gedunin (20 µM), and NDGA (5 µM). All values are presented as mean±SEM. All treated samples show elevated (at least 6 fold) luciferase activity.

DETAILED DESCRIPTION

Figure 1A:
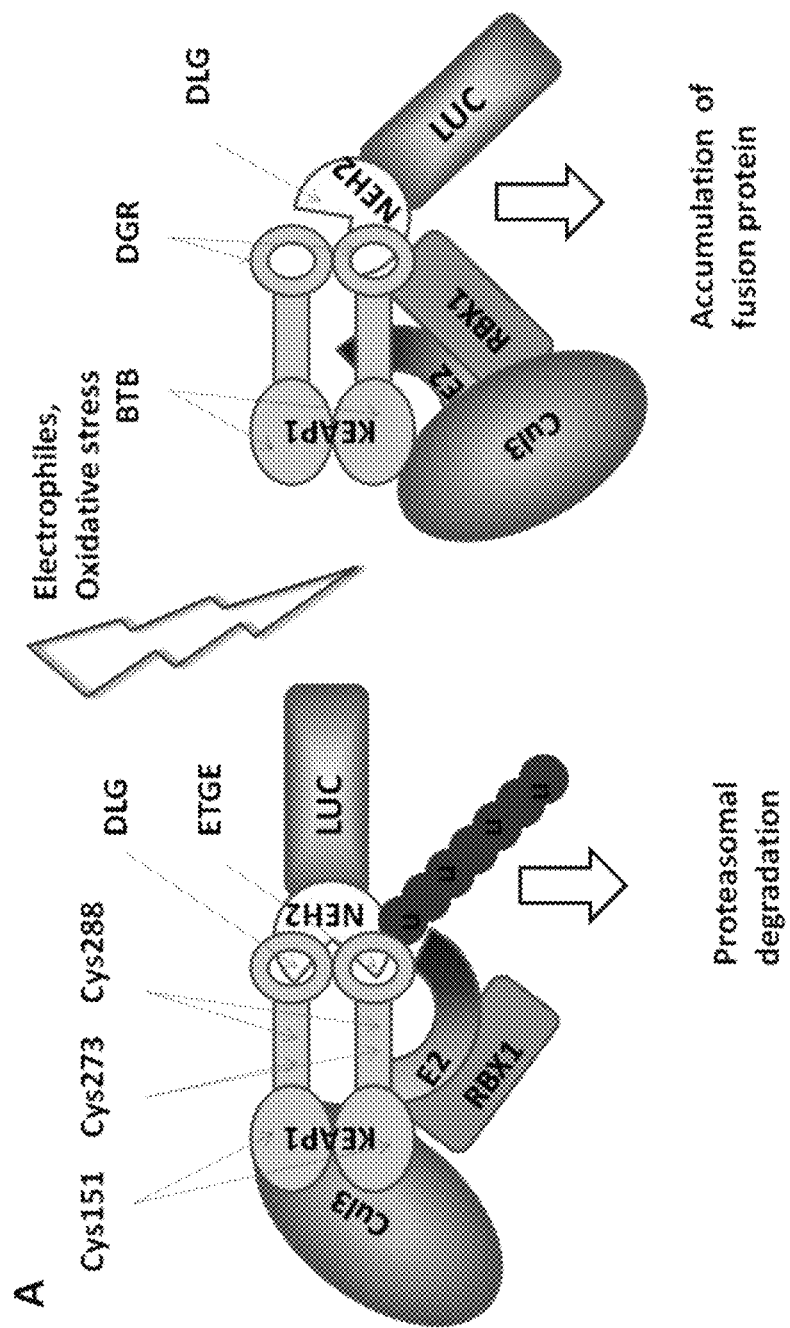
FIG. 1. Development of Neh2-luciferase reporter. A: Schematic presentation of reporter functioning. B: Time-course of the novel reporter response to TBHQ compared to that for the commonly used ARE-luc reporter. C: Time-course of Neh2-luc and HIF ODD-luc reporter responses to lactacystin showing the lag-period shortening with rising concentrations of the proteasomal inhibitor and thus confirming the switch of the rate-limiting step from specific recognition to proteasomal degradation. To supplement FIG. 1.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

DEFINITIONS

For convenience, before further description of the present invention, certain terms employed in the specification, examples, and appendant claims are collected here. These definitions should be read in light of the entire disclosure and understood as by a person of skill in the art.

The articles "a" and "an" are used herein to refer to one or to more than one (i.e., to at least one) of the grammatical object of the article. By way of example, "an element" means one element or more than one element.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "protein", and the terms "polypeptide" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain or an immunoglobulin binding domain.

The term "reporter gene" or "reporter" is known in the art and as used in the present invention with respect to a DNA sequence means any DNA sequence encoding a peptide, a protein or a polypeptide or nucleic acid that can give rise to a signal that can be detected, traced, or measured. As used in the present invention with respect to a DNA sequence, "reporter" will generally means a cDNA sequence (although in some cases a reporter gene may have introns) that encodes a protein or polypeptide or nucleic acid that is used in the art to provide a measurable phenotype that can be distinguished over background signals. The product of said reporter gene may also be referred to a "reporter" and may be mRNA, a peptide, a polypeptide, or protein, and may also be readily measured by any mRNA or protein quantification technique known in the art. "Reporter" may also refer to a tag or label that is affixed to a protein or peptide after it is expressed and may be any such tag or label known in the art. The reporter may, in a preferred embodiment, be a fluorophore.

A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other historically common fluorophores are derivatives of rhodamine (TRITC), coumarin, and cyanine. Newer generations of fluorophores such as the CF dyes, the FluoProbes dyes, the DyLight Fluors, the Oyester dyes, the Atto dyes, the HiLyte Fluors, and the Alexa Fluors are also known in the art.

The term "modulate" or "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. Therefore, an Nrf2 activator means a molecule that up regulates (e.g., activates, stimulates or enhances) a functional property or activity of Nrf2, such as one or more of the functions or activities known to be associated with Nrf2.

For example, Nrf2 has been shown to be a critical factor for the basal and inducible expression of many families of cytoprotective and detoxication genes (RAMOS-GOMEZ et al., *Proc Natl Acad Sci USA*, 98: 3410-3415 (2001); CHANAS et al., *J. Biochem*, 365: 405-16 (2002); THIMMULAPPA et al., *Cancer Res*, 62: 5196-203 (2002); MCMAHON et al., *Cancer Res*, 61: 3299-307 (2001); KWAK et al., *J Biol Chem*, 278: 8135-45 (2003); KWAK et al., *Mol Med*, 7: 135-45 (2001)). The diseases that could be treated or prevented by Nrf2 activation seem extensive as most have an etiology in oxidative stress.

In addition to conjugating and antioxidative genes, Nrf2 regulates other protective mechanisms including anti-inflammatory responses, the molecular chaperones/stress response system, and expression of the ubiquitin/proteasome system (KWAK et al., *J Biol Chem*, 278: 8135-45 (2003)). For this reason, activation of Nrf2 constitutes a broad protective response, making Nrf2 and its interacting partners important targets for anti-aging agents, as well as cancer chemoprevention.

Nrf2 activators have been investigated as anti-cancer drugs, and some have been shown to inhibit cancer formation in a variety of rodent organs, including the bladder, blood, colon, kidney, liver, lung, pancreas, stomach, and trachea, skin, and mammary tissue (ZHANG et al., *Mol Cell Biol,* 24: 10941-10953 (2004)).

In addition to cancer, Nrf2-regulated protective mechanisms may defend against and treat respiratory diseases such as hyperoxic lung injury (CHO et al., *Am J Respir Cell Mol Biol,* 26: 175-82 (2002)), emphysema (ISHII et al., *J Immunol,* 175: 6968-75 (2005)), asthma (RANGASAMY et al., *J Exp Med,* 202: 47-59 (2005)).

Nrf2 also plays a key role in the antioxidant defense of the central nervous system and has been shown to be important for neuroprotection in several acute and chronic neuropathological conditions (CALKINS et al., *Proc Natl Acad Sci USA,* 102: 244-9 (2005); BURTON et al., *Neurotoxicology,* 27(6): 1094-100 (2006)). Relevant CNS conditions include but are not limited to, stroke (both acute and chronic), multiple sclerosis, amyotrophic lateral sclerosis, the paroxysmal disorders (e.g., the epilepsies), autonomic nervous system dysfunction (e.g., arterial hypertension), movement disorders (e.g., hyperkinetic disorders, dyskinesias (resting tremor), basal ganglia hyperkinetic disorders (e.g., Huntington's chorea, hemiballismus), neuropsychiatric disorders (e.g., mania, psychosis obsessive compulsive disorder, and addiction), Alzheimer's disease, Parkinson's disease, hypothalamic disorders such as hyperlactemia, craniopharyngioma, gondotrophin deficiency, growth hormone deficiency, vassopressin deficiency, prolactinomas, obesity, neuropathic pain syndromes, acrodynia, Charcot-Marie-Tooth disease, diabetic neuropathies, nerve compression syndromes, neuralgias, neuromuscular junction diseases, POEMS syndrome, optical nerve injury diseases (e.g., glaucoma), olfactory disorders such as anosmia, hyponosmia, hypernosmia and impaired olfactory learning and memory and various retinal degenerative diseases (e.g., retinitis pigmentosa, macular degeneration).

Nrf2 has been shown to be important in cardiovascular diseases as well, such as cerebral ischemia (SHIH et al., *J Neurosci,* 25: 10321-10335 (2005)), and several other cardiac disorders (ZHU et al., *FEBS Lett,* 579: 3029-36 (2005)).

NRf2 activators have been investigated in the context of metabolic disease and diabetes, including insulin resistance and chronic kidney disease (CKD) in patients with diabetes mellitus. It has been established that there is a clear relationship between oxidative stress and inflammation and the various pathologies associated with diabetes, including diabetic nephropathy and chronic kidney disease. (BROWNLEE, *Nature,* 414 (6865): 813-20 (2001)).

The term "condition that is susceptible to treatment with a compound that upregulates NRF2" refers to any medical disease or condition for which there is evidence that NRF2 activity may be beneficial. Said condition may involve the nervous system, including the central nervous system.

The term "treating" as used herein is intended to encompass curing as well as ameliorating at least one symptom of any condition or disease.

A "patient," "subject" or "host" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats. The subject may be male or female, and may be elderly, an adult, adolescent, child, or infant. The term "juvenile" shall refer to infants, children, adolescents—any organism from the time between its birth and the maturation of its nervous system. The human subject may be caucasian, african, asian, semitic, or of other or mixed racial background. Preferred subjects include human patients suffering from or at risk for the neural diseases, conditions, and disorders described herein.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "NRF2" is an abbreviation for "nuclear factor (erythroid-derived 2)-like 2" or "NF-E2-related factor 2" or "NFE2-related factor 2" or "nuclear factor erythroid-derived 2-like 2." All terms are used interchangeably by those of skill in the art. Other terms used by those of skill in the art to refer to human NRF2 proteins include "NFE2L2", "HEBP1", "OTTHUMP00000205251", or "OTTHUMP00000207980." Nrf2 belongs to the Cap'n'Collar (CNC) family of transcription factors that contain a conserved basic region-leucine zipper structure. The Online Mendelian Inheritance in Man reference number for NRF2 is 600492. The term includes mutated NRF2 proteins.

The term "NEH2" is an abbreviation for "Nrf2-ECH homology 2". Neh2 is located at the N terminus of Nrf2 and acts as the regulatory domain for cellular stress response. There are two evolutionarily conserved motifs within the Neh2 domain among the CNC protein family. The DLG motif, which locates at the N-terminal region, has been reported to be important for ubiquitination and degradation of Nrf2, while the ETGE motif is essential for interacting with Keap1. In addition, seven lysine residues of the Neh2 domain, which reside upstream of the ETGE motif, have been shown to be indispensable for Keap1-dependent polyubiquitination and degradation of Nrf2.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. Infectious expression vectors, such as recombinant baculoviruses, are used to express proteins in cultured cells. Other infectious expression vectors, such as recombinant adenoviruses and vaccinia viruses, are used as vaccines to express foreign antigens in vaccines. However, the invention is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

Construction and Validation of Neh2-luc Reporter

This reporter construct of this invention is composed of a nucleic acid encoding a fusion protein between an Neh2 domain and a reporter protein.

Neh2 domains suitable for use in the present reporter construct include Neh2 domains from naturally occurring Nrf2 molecules of a mammal, such as human, mouse, chicken, among others.

In some embodiments, the Neh2 domain used in the reporter construct is the Neh2 domain of human Nrf2. In a specific embodiment, this Neh2 domain of human Nrf2 is composed of amino acids 1-97 of human Nrf2, as shown in SEQ ID NO: 11. Naturally occurring allelic variants and functional derivatives of SEQ ID NO: 11 are also suitable for use in the reporter construct of this invention.

In other embodiments, the Neh2 domain used in the reporter construct is the Neh2 domain of murine Nrf2 or chicken Nrf2. The native Neh2 domains of these molecules are set forth in SEQ ID NO: 15 and SEQ ID NO: 17, respectively. Naturally occurring allelic variants and functional derivatives of these naturally occurring Neh2 domains are also suitable for use in the reporter construct of this invention.

As used herein, a "functional derivative" of a naturally occurring Neh2 domain maintains characteristic structural features of a Neh2 domain attributable to its function (e.g., interacting with Keap1). In this context, relevant characteristic structural features of a Neh2 domain include the DLG motif and the ETGE motif and the lysine residues between them. For purposes of this invention, these motifs should be intact to preserve the function of the Neh2 domain (e.g., its ability to interact with Keap1), while amino acid residues outside of these motifs are relatively more tolerant to modifications (such as substitutions, including both conservative and non-conservative substitutions, and deletions or insertions at the N or C-terminus of the Neh2 domain).

The DLG motif refers to the peptide sequence, LXXQDXDLG (SEQ ID NO: 12), which is widely conserved in CNC factors. See, e.g., Katoh et al. (*Arch Biochm Biophys* 43: 342-350 (2005). The residue "X" at position 2 is often a bulky hydrophobic residue such as W or Y; "X" at position 3 is a positively charged residue such as R or K; and "X" at position 6 is a hydrophobic residue such as I or V. The ETGE motif refers to the peptide, ETGE (SEQ ID NO: 13). Thus, suitable functional derivatives of a naturally occurring Neh2 domain include, for example, peptides that share at least 95%, 96%, 97%, 98% or 99% of sequence identity with SEQ ID NO: 11, or have 1, 2, 3, 4, or 5 amino acid differences from SEQ ID NO: 11, where the differences occur outside of the DLG and ETGE motifs. Preferably, the differences consist of conservative amino acid substitutions at internal locations of an Neh2 domain, or deletions or additions at the N- or C-terminus. As examples of deletions at the N or C terminus, peptide composed of 92, 93, 94, 95, or 96 contiguous amino acids of SEQ ID NO: 11 may be suitable for use in this invention.

Examples of conservative substitutions include the substitution of a non-polar (hydrophobic) residue such as I, V, L or M for another; the substitution of one polar (hydrophilic) residue for another polar residue, such as R for K, Q for N, G for S, or vice versa; and the substitution of a basic residue such as K, R or H for another or the substitution of one acidic residue such as D or E for another. Examples of non-conservative substitutions include the substitution of a non-polar (hydrophobic) residue such as I, V, L, A, M for a polar (hydrophilic) residue such as C, Q, D, K and/or vice versa.

In the reporter construct of this invention, a nucleic acid encoding an Neh2 domain is linked to a reporter gene. A variety of reporter genes can be used which are capable of generating a detectable signal. Examples of suitable reporter genes include, but are not limited to, luciferase gene, lactosidase gene, green fluorescent protein gene, or a yellow fluorescent protein gene, or cyan fluorescent gene, or red fluorescent gene.

In some embodiments, a nucleotide sequence encoding an amino acid linker is included in a reporter construct between the Neh2 domain and the reporter. Use of linkers in making fusion proteins is well documented in the art. Linkers are generally short peptides composed of small amino acid residues such as Glycine and Serine.

A nucleic acid which codes for an Neh2-reporter fusion is placed in an operable linkage to a promoter functional in a recipient cell, which can be a constitutive promoter or an inducible promoter to drive the expression of the Neh2-reporter fusion molecule in the recipient cell. A CMV promoter and a SV40 promoter are examples of promoters that can drive strong expression in a wide spectrum of cell types and are suitable for use in the reporter constructs of this invention.

A nucleic acid construct or vector, which carries an Neh2-reporter fusion nucleic acid, can be introduced into an appropriate host cell by various means available in the art, such as liposome-mediated transfection, electroporation, calcium phosphate precipitation, DEAE-Detxan followed by polyethylene glycol, among others. While the examples disclosed herein exemplify a human neuroblastoma cell line as a recipient cell, a variety of mammalian cell lines including human cell lines are available for use. The resulting cell line can be used to screen for useful compounds, such as Nrf2 modulators (activators or inhibitors), as further disclosed hereinbelow.

In a specific embodiment, the Pcmv-driven Neh2-luc reporter supports the constitutive, intracellular synthesis of a novel fusion protein composed of amino acid 1-97 of human Nrf2 (containing the Neh2 domain) and firefly luciferase. Since the Neh2 domain is known to be sufficient for recognition by the ubiquitin-ligase complex and subsequent ubiquitination of the fusion protein, the recombinant luciferase labeled protein should undergo proteasomal degradation. The steady-state concentration of the fusion protein should correspond to the equilibrium between its synthesis and degradation (FIG. 1A). The background luminescence signal calibrated with recombinant luciferase allows us to estimate the steady-state concentration of the Neh2-luciferase fusion protein: the background is ca. 15-20 rlu, which corresponds to 0.25-0.33 pg luciferase protein and is more than two orders of magnitude lower than that observed for the cell line expressing wild-type luciferase under control of the same promoter. The low steady state luciferase activity (recalculated as 0.6-0.8 nM fusion protein for 30,000 cell/well density and $233\mu^3$ single cell volume) suggests that in spite of forced expression of the Neh2-luciferase fusion protein, it is successfully recognized by the endogenous Keap1-Cul3 complex and almost fully degraded. The findings support prior observations that the Neh2 domain is critical for Keap1 binding and sufficient for recognition and degradation of Neh2-containing fusion protein (ZHANG et al., *Mol Cell Biol*, 24: 10941-10953 (2004)).

Figure 8A:
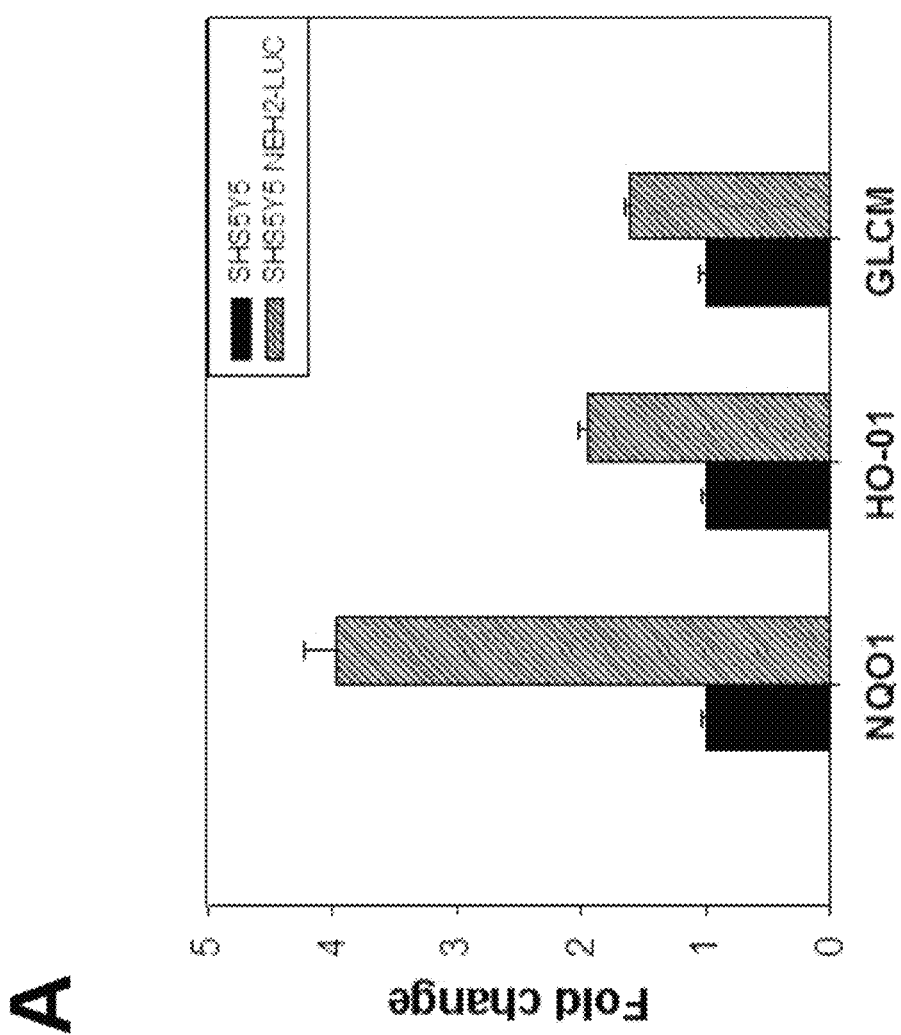
FIG. 8 shows (A) increased expression of Nrf2-regulated genes in the Neh2-luc reporter line as a result of rescue of endogenous Nrf2 in the presence of the overexpressed Neh2-luciferase fusion; and (B) reporter response to canonical Nrf2 activators—PGJ2, TBHQ, and sulforaphane—in comparison to the absence of any response for HIF ODD-luc reporter confirming the specificity of each reporter.

The overexpressed Neh2-luciferase fusion protein successfully competes with endogenous Nrf2 for Keap1 binding and thus, rescues endogenous Nrf2 from degradation: the reporter cell line shows a 4-6-fold increase in mRNA for Nrf2-regulated genes such as HO-1 and GSLM (FIG. 8A). The reporter exemplifies the action of an "ideal Nrf2 activator" which stabilizes endogenous Nrf2 by competing for Keap1 binding and not by modifying Keap1 chemically. Of note, stabilization of endogenous Nrf2 and the upregulated expression of protective genes may explain the increased stability of the reporter cell line as compared to the original non-transfected cell line.

Figure 8B:
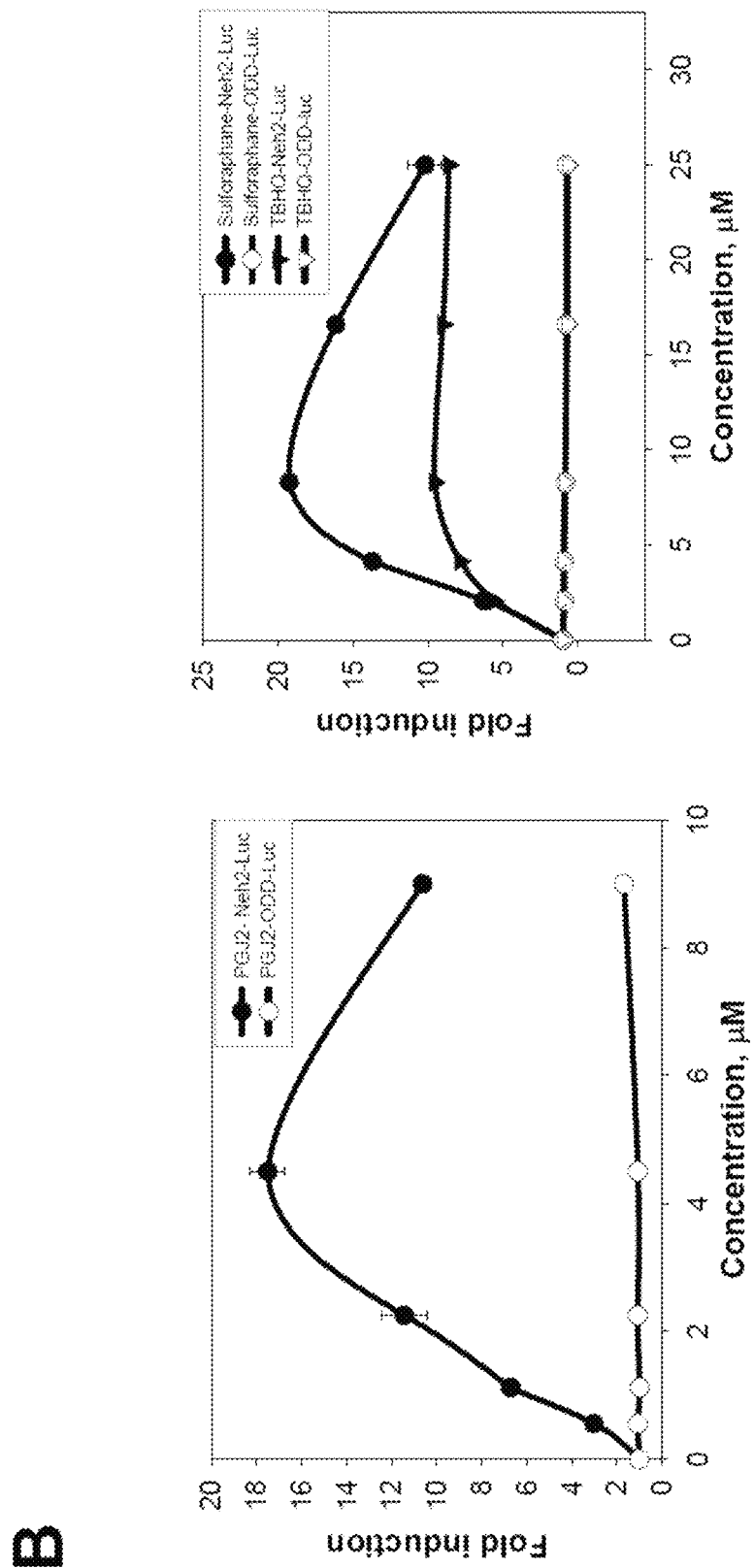

Canonical activators of Nrf2 such as 15-deoxy-prostaglandin J2 (15d-PGJ2) (ITOH et al., *Mol Cell Biol* 24: 36-45 (2004)), sulforaphane (MYZAK et al., *Cancer Lett*, 233: 208-218 (2006)) and tert-butylhydroquinone (TBHQ) (MOEHLENKAMP et al., *Arch Biochem Biophys*, 363: 98-106 (1999)) disrupt the interaction in the Neh2luc-Keap1-Cul3 complex leading to a measureable increase in luciferase activity and protein (FIG. 8B). This effect is not observed for the reporter cell line bearing another construct, HIF ODD-luciferase, where HIF-1α oxygen degradable domain is fused to luciferase (SMIRNOVA et al., *Chem Biol*, 17: 380-391 (2010)), thus indicating the specific character of Neh2-luc reporter response (FIG. 8B).

If compared to commonly used ARE-luc reporter, the newly developed one has an obvious advantage to monitor immediate changes upon the addition of Nrf2 activators: the response of ARE-luc reporter to TBHQ is 3 h delayed (FIG. 1B). The response of both Neh2-luc and HIF ODD-luc reporters to a proteasomal inhibitor is similar (FIG. 1C): there is a concentration-dependent delay (lag-period) in reporter response. The shortening lag-periods observed with rising concentrations of the proteasomal inhibitor provides evidence for the switch of the rate-limiting step from the disruption of the Neh2-Keap1-Cul3 complex to the proteasomal degradation step. The comparison of Neh2-luc and HIF ODD-luc reporter performance with respect to Nrf2 activators (FIG. 8B) and proteasomal inhibitors (FIG. 1C) proves the specific character of each reporter.

Figure 2:
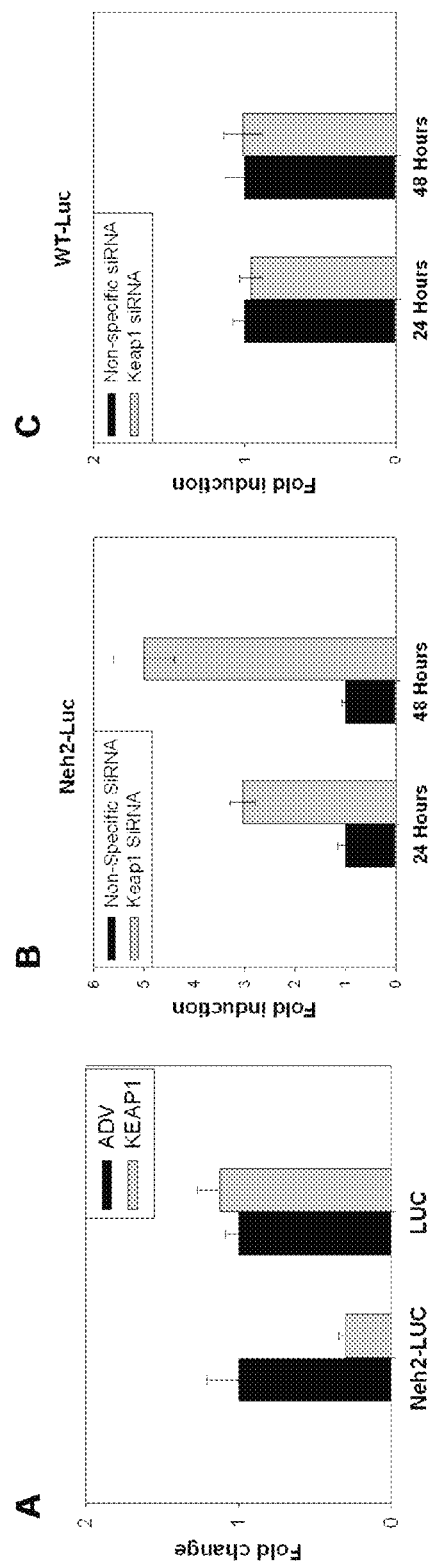
FIG. 2. Neh2-Luc reporter response to up- and down-regulation of Keap1 levels. A: Keap1 overexpression resulted in a decreased level of luminescence in Neh2-luc cells transfected by Keap1 adenovirus. The efficiency of transfection of Neh2-luc cell line with FLAG-labeled Keap1-overexpressing adenovirus was 45-70% as judged by immunostaining with anti-FLAG antibodies (see FIG. 9A). B: siRNA Keap1 knockout resulted in an increased level of luminescence only in Neh2-luc cell line, but not in WT-luc line. The siRNA Keap1 knockout was confirmed by RT-PCR: decreased levels of Keap1 mRNA and increased levels of mRNA of Nrf2 regulated genes in both Neh2-luc and WT-luc cell lines (see FIG. 9B).
Figure 9A:
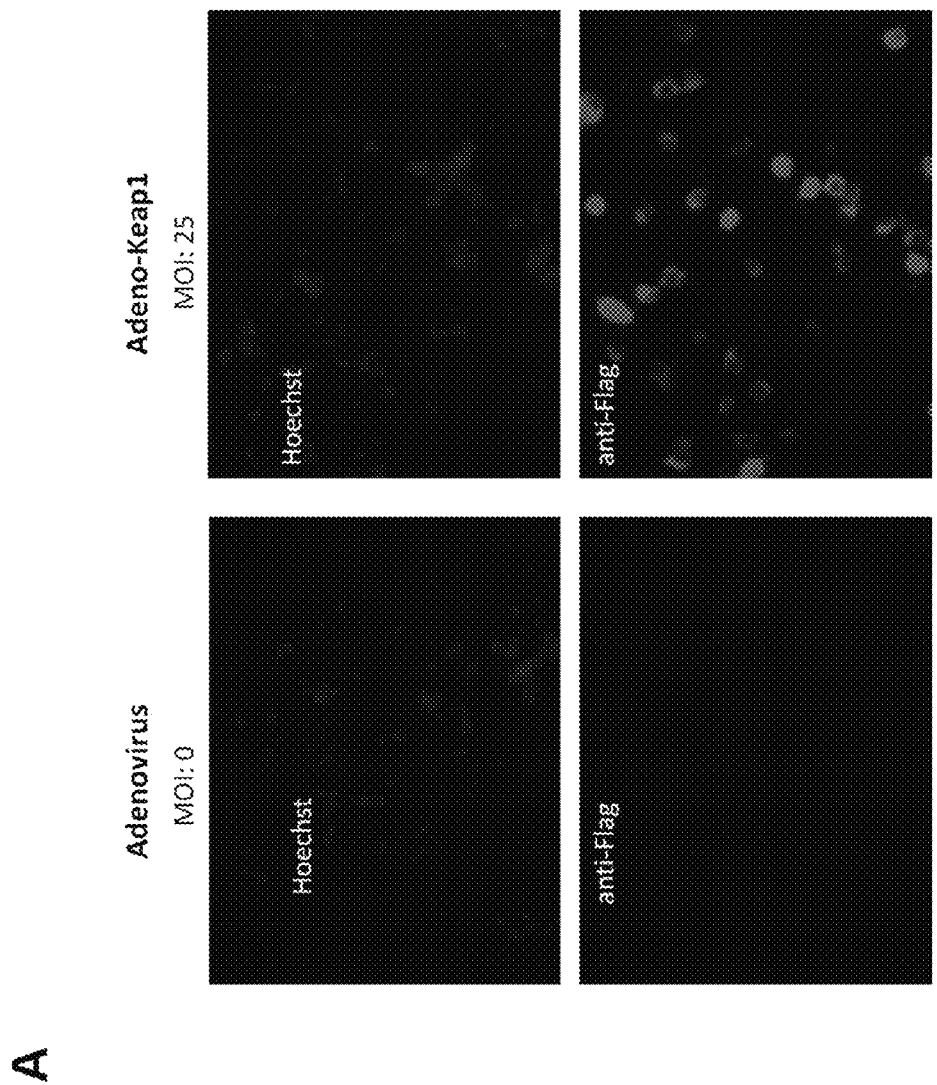
FIG. 9. Validation of Neh2-luc reporter system. Control experiments for FIG. 2. A: The efficiency of transfection of Neh2-luc cell line with FLAG-labeled Keap1-overexpressing adenovirus was 45-70% as judged by immunostaining with anti-FLAG antibodies. The Hoechst staining is a nuclear stain and the anti-FLAG recognizes a FLAG sequence contained within the exogenous Keap1. The transduction efficiency for this particular image is ~45%. B: siRNA knockout of Keap1 inhibited the expression of Keap1 and induced transcription of Nrf2-regulated genes such as NAD(P)H dehydrogenase (NQO1), heme oxygenase 1 (HO-1), glutamate-cysteine ligase catalytic subunit (GCLC), and glutamate-cysteine ligase modifier subunit (GCL M) in both cell lines, e.g. carrying Neh2-luc fusion and plain luciferase. Data are the means±SEM of three independent experiments normalized to GAPDH control.
Figure 9B:
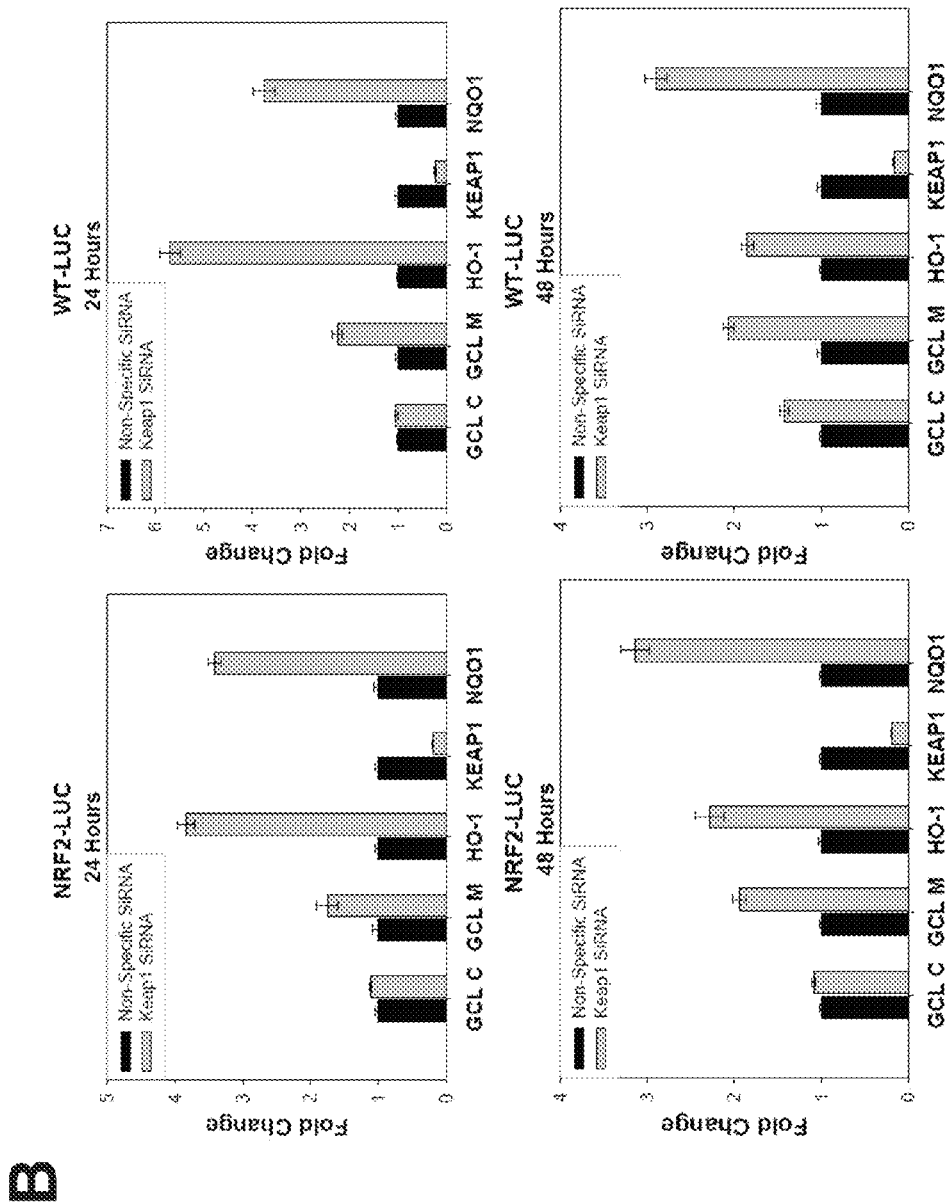

The Neh2-luc reporter system is a novel tool to monitor the direct effect of a particular compound on the first step controlling Nrf2 stability, i.e. Nrf2-Keap1 and/or Keap1-Cul3 interaction. Validation studies further performed using traditional approaches (FIG. 2) demonstrate that Keap1 regulates the stability of the Neh2-reporter in the same manner as for endogenous Nrf2: forced expression of Keap1 in the Neh2-luc reporter cell line (FIG. 9A) led to a 3.5-fold decrease in the background luminescence (FIG. 2A). In contrast, Keap1 reduction by siRNA resulted in a steady state increase in Neh2-luc reporter activity (FIG. 2B) and an induction of transcription of Nrf2-regulated genes in both Neh2-luc and WT-luc expressing cell lines (FIG. 9B). Keap1 depletion had no effect on the levels or activity of a native firefly luciferase expressed under the same CMV promoter, confirming the key role of the Neh2 domain in the Keap1-dependent regulation of the Neh2-luciferase fusion protein (FIG. 2C). The results of Keap1-overexpression (FIG. 2A) or siRNA mediated reduction in Keap1 levels (FIG. 2B) establish that the stability of the Neh2-luc reporter directly depends on the expression level of Keap1.

In contrast to the previously utilized ARE-based promoter-reporter constructs, the novel reporter provides real time monitoring of Nrf2 stabilization and can be successfully used for high throughput screening purposes (see below) as well as in vivo bioluminescent imaging.

Pilot HTS of Spectrum library

In a further aspect, reporter cells line disclosed herein are used to screen for compounds, such as Nrf2 modulators (activators or inhibitors). In some embodiments, compounds being tested are small molecule compounds, e.g., organic compounds having a molecular weight of less than 1500 Dalton, 1200 Dalton, 1000 Dalton or even 800 Dalton. Peptides or other classes of molecules may also be screened.

In accordance with this invention, the level of expression of the reporter gene from a Neh2-reporter construct, hence the amount of signal detected, reflects the ability and extent a compound can modulate Nrf2. Thus, an Nrf2 modulator can be identified by contacting a reporter cell line with candidate compounds, detecting signals generated from the reporter, and comparing the amount of signals with a control. In some embodiments, the control represents the amount of signals detected from a reporter cell line in the absence of a candidate compound under identical conditions. In other embodiments, the control represents the amount of signals detected from a reporter cell line in the presence of a known activator compound under identical conditions, as exemplified hereinbelow.

The exemplary reporter cell line generated herein was stable for more than a year providing constant readings for all control Nrf2 activators. It has been shown to be suitable for HTS purposes: the results of a pilot screen of the Spectrum library using the novel Neh2-luc reporter cell line with 10 μM tert-butylhydroquinone (TBHQ) as a positive control are presented below. TBHQ has been used in vivo for prophylaxis against ischemic stroke (SHIH et al., *J Neurosci*, 25: 10321-10335 (2005)). TBHQ was chosen among other canonical activators tested since the concentration titration curve had no peaks and showed a saturation plateau (FIG. 8B), and thus was ideal for signal normalization. Induction of luciferase activity is reported throughout as percent of activation by 10 μM TBHQ.

The screen revealed 224 hits exhibiting Neh2-luc reporter activity equal or higher than 25% of TBHQ; among those, 100 showed activation of at least 75% of that induced by TBHQ. Thus, 5% of biologically active compounds and drugs presented in the Spectrum library are at least 75% as potent as TBHQ in activation of Nrf2. The prevalence of hits may reflect the important role that Nrf2 plays in xenobiotic detoxification of a large number of chemical entities.

As a further test of specificity of the identified Nrf2 activators, the inventors compared 200 putative Nrf2 activators to almost 30 hits from HTS of the same library found using a HIF1 ODD-luc reporter, HIF-1α oxygen degradable domain fused to luciferase, as described (SMIRNOVA et al., *Chem Biol*, 17: 380-391 (2010)). Upon hydroxylation at proline 564 in normoxia, the ODD-luciferase recruits the E3 Ubiquitin Ligase, Von Hippel Lindau protein, and targets the ODD-luciferase for proteasomal degradation (SMIRNOVA et al., *Chem Biol*, 17: 380-391 (2010)). The observation that the Nrf2 (Neh2-luc) or HIF1 (ODD-luc) screens of the identical 2,000 compound library give hits that do not overlap is the strongest evidence for specific chemical control of the stability of both reporters. The findings suggest that rate-limiting step in reporter activation is determined by Neh2 (of Nrf2) or ODD (of HIF1α) and not by proteasomal degradation. In other words, the reporters select unique activators of Nrf2 and HIF1, respectively, and not common inhibitors of proteosomal degradation.

Well-known drugs and hormones were found in the screen as potent activators of the Neh2-luc reporter, for example minocycline (KUANG et al., *Brain Res*, 1286: 174-184 (2009)), sulindac, auranofin (KATAOKA et al., *J Biol Chem*, 276: 34074-34081 (2001)), teniposide, podophyllotoxin derivatives, which showed 200% activation over the canonical TBHQ-induced Neh2-luc response. Purpurogallin carboxylates (FIG. 3, Ic), prevalent components of black tea, were extremely potent in activating the reporter up to 500% of TBHQ levels. It is of interest to note that drinking black tea 3-times a day was recently reported to delay Parkinson's disease symptoms onset by more than 7 years (KANDINOV et al., *Parkinsonism Relat Disord*, 15: 41-46 (2009)). Also found in the screen were representatives of all structural classes (FIG. 3) which were described previously as inducers of the Nrf2-regulated gene nicotinamide quinone oxidoreductase 1 (NQO1) (DINKOVA-KOSTOVA et al., *Methods Enzymol*, 382: 423-448 (2004)). This fact provides additional evidence for reliability of the novel reporter, which is capable of identifying all hits reported previously using ARE-luc reporter or those inducing Nrf2-dependent genes.

The hits included phenolic antioxidants; diphenols (FIG. 3, I); aminophenols or their derivatives, for example, acetaminophen exhibiting more than 50% activation; phenylene diamines; substituted coumarines, and especially those containing adjacent hydroxy-groups (FIG. 3, II); other cyclic lactones and enones; Michael reaction acceptors such as fumaric, maleic, acrylic, crotonic, ferulic and caffeic acid derivatives, with bis-salicylfumarate (FIG. 3, IIIa) being the most potent hit in this group (>300% activation); chalcones providing activation up to 400% (FIG. 3, IIIc); sappanones and sappanols; flavanones; flavones (FIG. 3, IV), such as 3,7,3',4'-tetrahydroxyflavone, fisetin, and 3,5,7,3',4'-pentahydroxyflavone, quercetin, showing >300% activation, and isoflavones such as koparin (>200%) and genistein (>100%).

Structure-activity relationship studies for flavones indicate the necessary presence of 3-hydroxy-group, since 3',4'-dimethoxy-3-hydroxyflavone and kaempferol (3,5,7,4'-tetrahydroxyflavone) are 2.5-fold less effective than quercetin and fisetin. Luteolin (5,7,3',4'-tetrahydroxyflavone) has an effect similar to kaempferol and thus, is much lesser active than fisetin and quercetin, although they all have two adjacent hydroxy-groups on a freely rotating phenyl ring. Additionally, double Michael reaction acceptors such as curcumins showing more than 200% activation (FIG. 3A, V), dithiolethiones, dimercaptanes, and isothiocyanates (FIG. 3, VI) came up as hits. Sulforaphane (FIG. 3, VIc) is the prototypic activator of Nrf2 (FIG. 8A). Heavy metals, such as cadmium and cisplatin, were also hits showing modest activation of 30-50%.

Of the 45 hits from the ARE-GFP screen of the same library (SHAW et al., UK Patent Application #0918626.3, Priority Date (Oct. 24, 2008), Publ Date (May 5, 2010)), 37 of those were among our hits. The conditions of HTS were very different, in particular the incubation time (24 h ARE-GFP vs 3 h Neh2-luc), so some of the hits missed were likely to induce extremely delayed effects. The lesser number of hits in the ARE-GFP screen could reflect both prolonged incubation and lesser sensitivity of the assay: the cell number per well was at least 7 times higher and ebselen as a positive control induced only a 3-fold increase in the reporter signal (SHAW et al., UK Patent Application #0918626.3, Priority Date (Oct. 24, 2008), Publ Date (May 5, 2010)) compared to more than 10-fold activation by TBHQ in the case of Neh2-luc reporter (FIG. 1B).

Novel Classes of Nrf2 Activators

Figure 3:
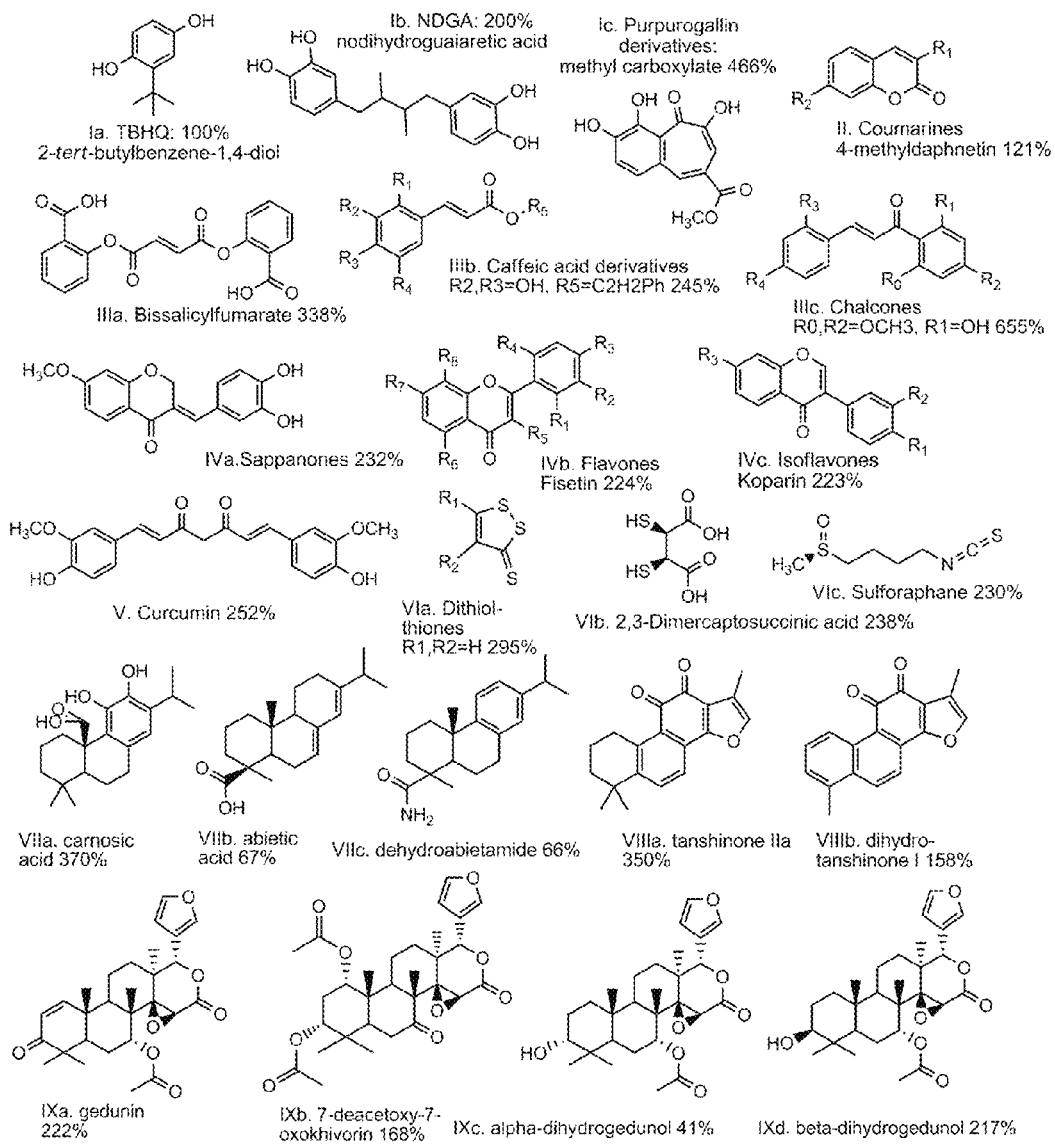
FIG. 3. Structural formulas of HTS Hits. Activation effects are shown in % for 16 µM of the representative hits. See also FIGS. 10, 15, 16, and 17 for other scaffolds identified.

The previously unknown classes of hits included:

(1) all members of gedunin/khivorin family (18 compounds) were among the hits (see FIG. 3, group IX). The finding of numerous gedunins as hits was unexpected. Moreover, some of the tricyclic hits (FIG. 3, group VII) resembled the structure of gedunin very closely. The stereo-effects in play are obvious from comparison of tanshinone (FIG. 3, VIIIa) and dihydrotanshinone (VIIIb), the major components of danshen, one of the most important traditional Chinese medicines widespread in Asian countries: both compounds have a clear quinone motif, but the change from planar to 3D-scaffold leads to a significant increase in the reporter activation. Although one may ascribe the effects of group VII and VIII compounds (FIG. 3) exclusively to the presence of neighboring hydroxy-groups/quinone moiety, the activation by dihydroabietamide (VIIc) cannot be explained by alkylation or redox cycling mechanism. The structure-activity relationship within the gedunin/khivorin group (FIG. 3, IX) clearly points to the structural effects in play: the most remarkable is the comparison between alpha- and beta-dihydrogedunols which differ only by the orientation of a hydroxy-group (activation effects are 40% and 220%, respectively).

(2) planar $Zn^{2+}$ chelators such as 8-hydroxyquinoline and chloroacetoxyquinoline (60% activation). The presence of $Zn^{2+}$-atom in Keap1 was documented for the recombinant protein produced in *E. coli*, and an estimate for $Zn^{2+}$ binding constant was on the order of pM (DINKOVA-KOSTOVA et al., *Biochemistry*, 44: 6889-6899 (2005)). We recently identified a number of novel branched oxyquinolines as inhibitors of the HIF prolyl hydroxylases (SMIRNOVA et al., *Chem Biol*, 17: 380-391 (2010)). None of these compounds (which are also zinc chelators with Ki below 200 nM) showed any Neh2-luciferase activation, pointing to specific structural requirements for oxyquinoline zinc chelators as Nrf2 activators. 3-Hydroxyflavone was found as a modest Nrf2 activator and is known to bind zinc better than 5-hydroxyflavone or 3'4'-dihydroxyflavone (LAPOUGE et al., *J Phys Chem A*, 110: 12494-12500 (2006)).

Figure 10:
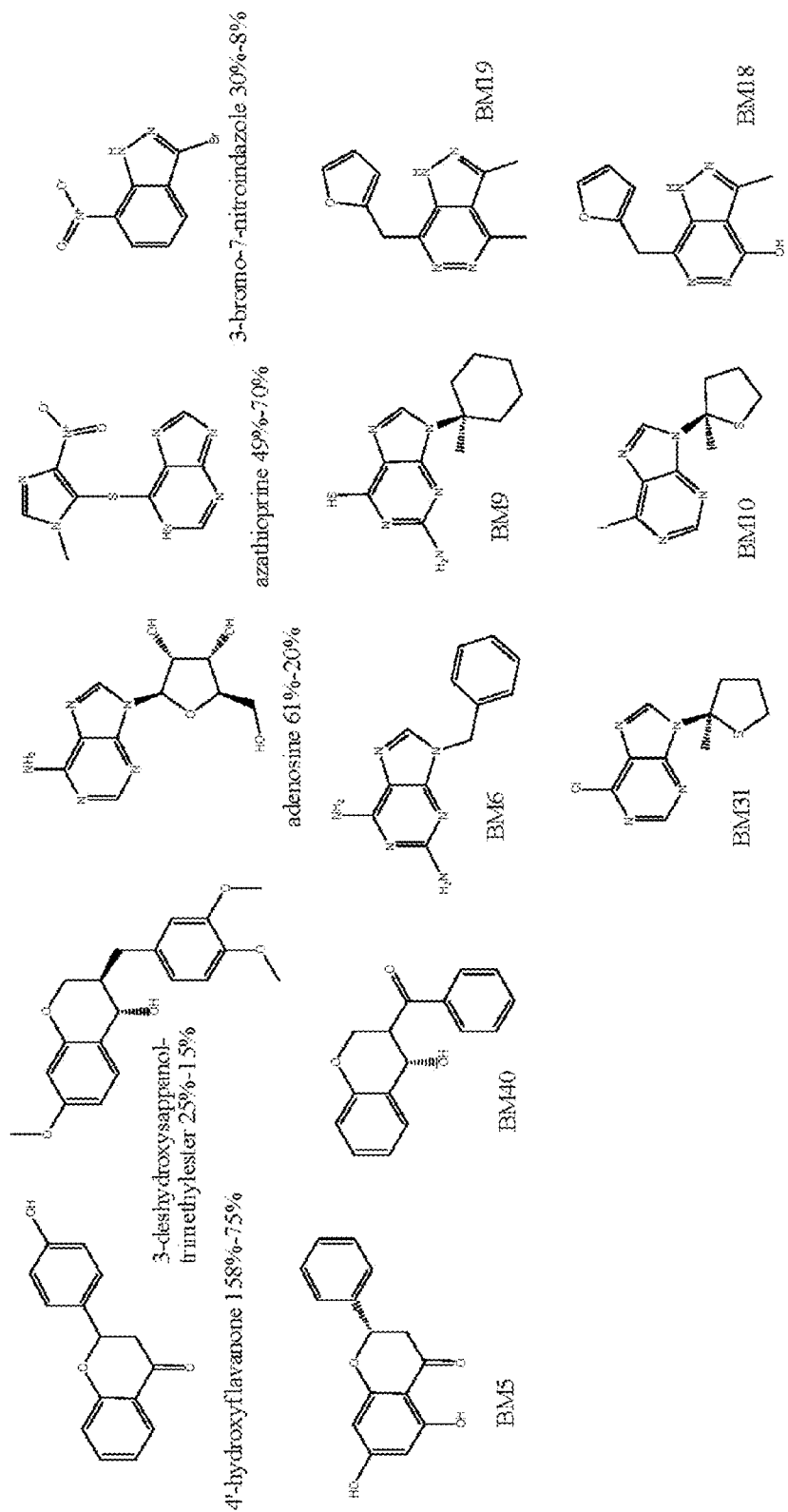
FIG. 10. Similarity in scaffolds of purine, flavanone and sappanol hits from HTS with Neh2-luc reporter (upper line) and those reported from virtual screening of compounds docking the intervening region of Keap1 (purines BM 6,9,10, 31; pyrazolopyridazines B18, B19; 5,7-dihydroxyflavanone BM5; and sappanol derivative, ((4S)-4-hydroxychroman-3-yl)(phenyl)methanone BM40) 31. B10,31 and 40 were shown to be the best ones in activating Nrf2-induced genes 31. Activation effect of HTS hits shown in %% for 16 and 32 µM of the corresponding compound upon 3 h incubation.

(3) adenosine, azathioprine, bromonitroindazole were modest hits in our screen: they resemble the recently published structures of novel Nrf2 inducers supposedly targeting the intervening region of Keap1 (WU et al., *Chem Biol Drug Des*, 75: 475-480 (2010)) (see FIG. 10). In the latter paper, the authors performed virtual screening of chemical databases for putative Nrf2 inducers showing best scores for docking into the newly built 3D model of the Keap1 intervening domain with subsequent verification by ARE-luciferase based assay (WU et al., *Chem Biol Drug Des*, 75: 475-480 (2010)). They found substituted purines with a freely rotating tetrahydrothiophene ring in the 7th position (BM10 and BM31 in FIG. 10), with lower potency than sulforaphane (WU et al., *Chem Biol Drug Des*, 75: 475-480 (2010)). Of note, the tetrahydrothiophene ring is extremely sensitive to oxidation and it is not clear to which extent the mechanism of action of these new compounds can be ascribed to specific interaction with Keap1.

Time-Course of Reporter Activation as a Tool for Hit Classification

As mentioned, the novel reporter provides the possibility of real time monitoring for changes in the stability of Nrf2 in the form of the luciferase labeled Neh2 domain for the first time. By following the kinetics of reporter activation one may expect to discriminate the mechanism of action of various Nrf2 activators, i.e. direct activators will exert immediate effects, while those acting indirectly will show lag-periods of different durations.

The mechanism of Nrf2 activation has been postulated to occur due to the chemical modification of key thiols in Keap1. Accordingly, all alkylating agents tested were hits. The exact mechanism of action of redox-cycling compounds like ortho- or para-dihydroxy-phenols is not known, although they are supposed to undergo oxidation resulting in formation of potential alkylating compounds.

Among well-known classes of hits, particularly those of catechol-type, with two adjacent hydroxy-groups, e.g. fisetin, quercetin, but not luteolin (class IV, FIG. 3), and nordihydroguaiaretic acid (NDGA, class I, FIG. 3), demonstrated the best parameters of activation, i.e. the lowest half-activation concentration, the highest amplitude, and the lowest toxicity in the concentration range providing maximum activation of the reporter. Moreover, in contrast to other hits of the screen, and especially in comparison with the established Nrf2 activators showing a gradual response on a concentration titration curve (FIG. 8B), NDGA and fisetin exhibit a very steep concentration response curve (FIG. 4A-B).

Figure 4:
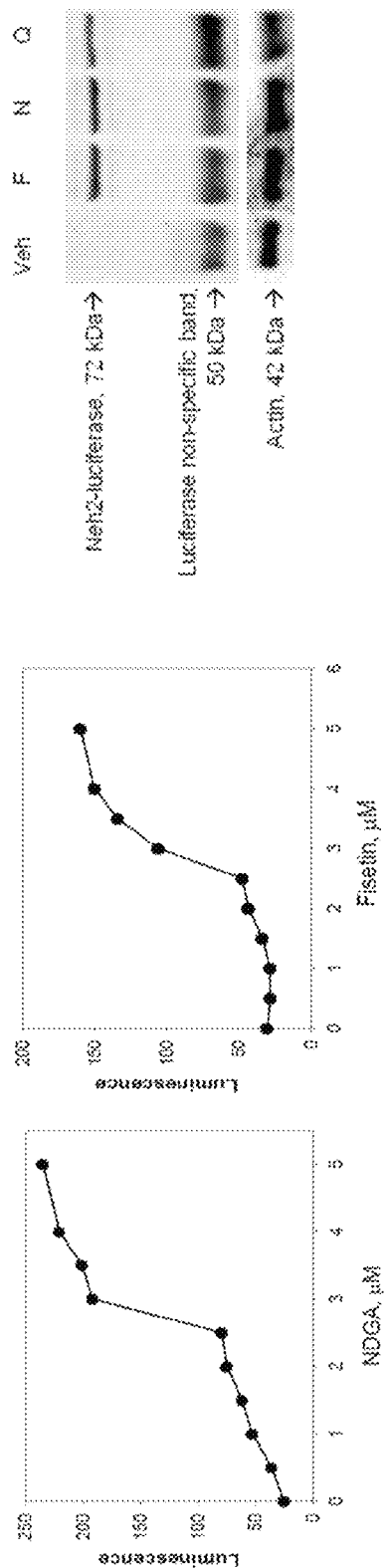
FIG. 4. Concentration dependence of luciferase signal for "switch"-type hits (A-B) and confirmation of fusion protein accumulation by Western blot (C). 3 h treatment with 5 µM Fisetin (F), 5 µM NDGA (N), and 4 µM quercetin (Q). The control cell lines WT-luc and HIF ODD-luc (SMIRNOVA et al., Chem Biol, 17: 380-391 (2010)) did not accumulate luciferase fusion under the same exposure conditions (FIG. 11).
Figure 11:
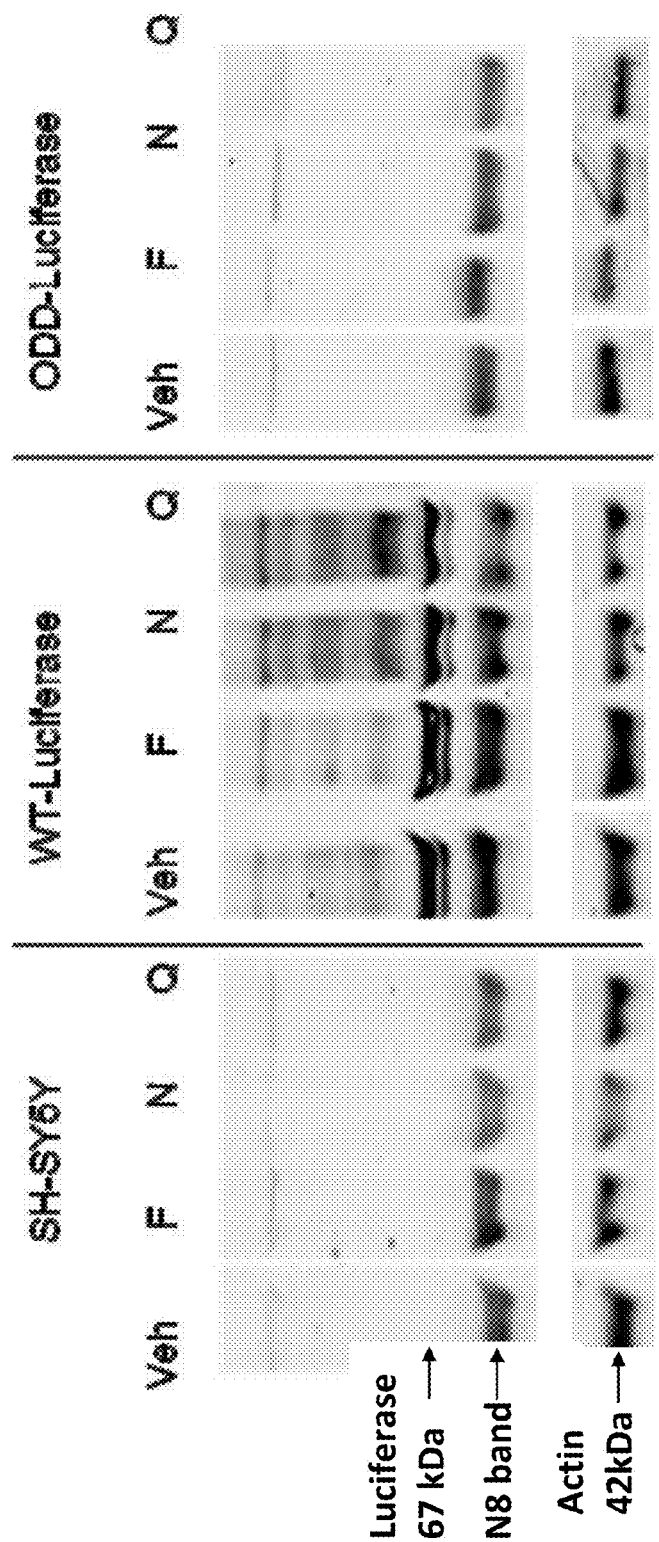
FIG. 11. Control experiment for FIG. 4C. Western blot analysis of all control cell lines incubated for 3 h with 5 µM Fisetin (F), 5 µM NDGA (N), and 4 µM quercetin (Q). The control cell lines SH-SY5Y and SH-SY5Y transfected with pcDNA3-ODDLUC8 did not accumulate luciferase or luciferase fusion under the same exposure conditions, while SH-SY5Y cells carrying pcDNA3-LUC3 express plain luciferase protein independent of any treatment.

We decided to undertake a separate study to use the kinetics of reporter activation to compare the mechanism of action of our best hits using the Neh2-luc reporter system. In addition to providing a novel categorization of Nrf2 activators, our central interest was to further characterize our best hits, which exhibited a very steep concentration response over a very narrow range of concentrations (FIG. 4). An increase in Neh-2 luciferase activity was shown to correspond to the accumulation of the fusion protein monitored by immunoblotting with selective anti-luciferase antibodies after treatment with our most potent hits (FIG. 4C). Under basal conditions, no fusion protein was detectable consistent with a model in which Keap1 binding to the Neh2-luciferase triggers its efficient proteasomal degradation (FIG. 4C and FIG. 11).

For the comparative studies we selected a number of hits, suspected to work via different mechanisms: TBHQ, orthophenylene diamine (oPD), o-catechol, NDGA, quercetin, and fisetin as representatives of redox-cycling compounds; sulforaphane, and pyrithione as alkylating compounds; $Cd^{2+}$, as a heavy metal of unknown mechanism of action; geldanamycin, specific inhibitor of Hsp90 working via blockade of ATP-binding site (OBERMANN et al., *J Cell Biol*, 143: 901-910 (1998)), trichostatin A (TSA), a general inhibitor of HDACs resulting in destabilization of Hsp90, and gedunin, which is supposed to disrupt the association of Cdc37 and Hsp90 (Brandt et al. 2008).

In accord with the time-course of reporter activation (FIG. 5), we have classified hits into 5 groups: (1) immediate activation but gradual stabilization over time, like sulforaphane, pyrithione, TBHQ, quercetin, gedunin; (2) gradual stabilization with a barely detectable (20 min) lag-period (catechol); (3) gradual stabilization with a short lag-period of 40-50 min (oPD), (4) stabilization after a prolonged lag-period, 1-3 h ($Cd^{2+}$, TSA, geldanamycin); and (5) activation via a switch or receptor, i.e. showing sharp conversion from almost no effect to full activation over a narrow concentration range (NDGA and fisetin—the best hits in the screen).

The similar behavior of TBHQ, sulforaphane, auranofin, pyrithione and gedunin permits their classification into one group of "alkylators". Catechol is likely to undergo quick transformation and then also works as an "alkylator". Apparently oPD and catechol behave differently: oPD has a clearly defined short lag-period, which may reflect the additional modification step of the inducer, such as enzymatic oxidation with copper-dependent enzymes (WANG et al., *Chem Biol*, 17: 75-85 (2010)): oPD is possibly the one working through redox cycling.

The effect of $Cd^{2+}$ is more than 1 hour-delayed, so it either has problems with getting into the cell, or more likely, has an indirect effect on the system via inactivation of thiol-disulfide exchange by inhibiting thioredoxin reductase/thioredoxin system. It is of interest to note that increased concentrations of $Cd^{2+}$ shorten the lag-period, while in the case of oPD, the lag-period duration barely depends on the inducer concentration.

Figure 5:
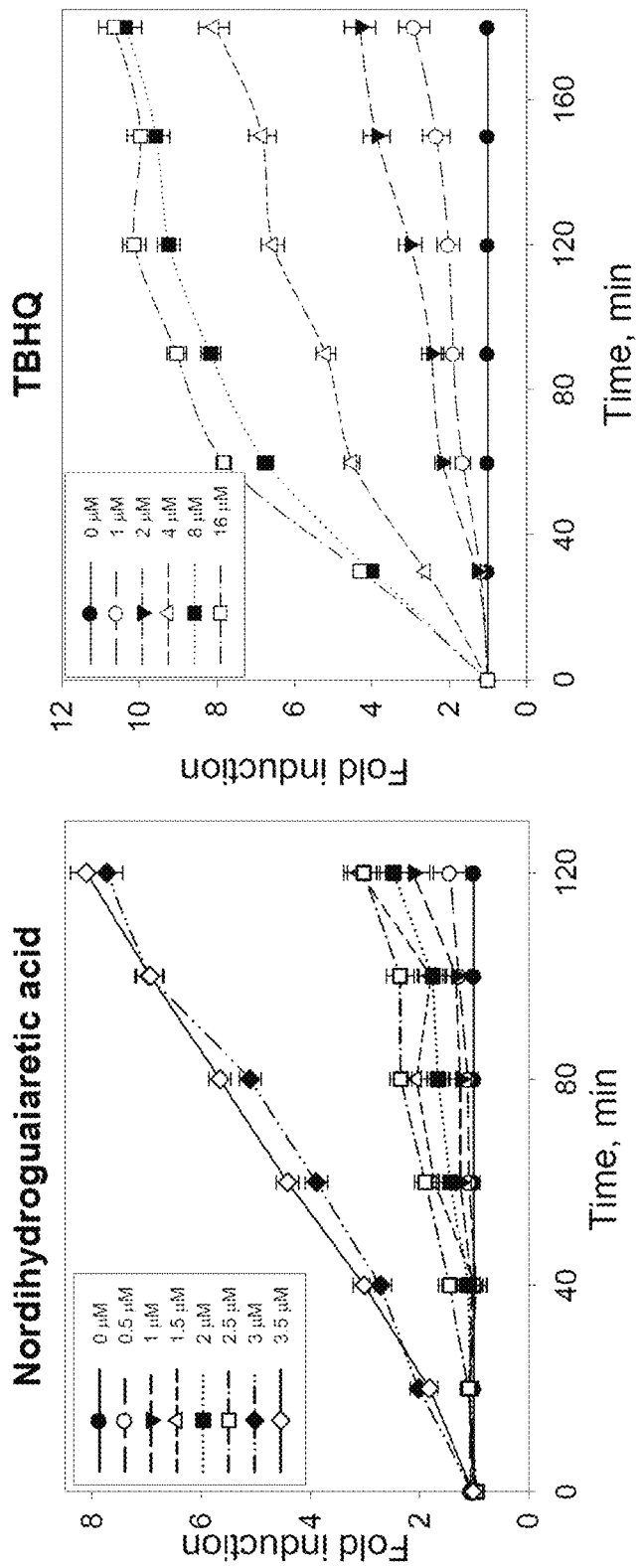
FIG. 5. Classification of HTS best hits based on kinetics of reporter activation: switch-type activators (NDGA and fisetin); immediate alkylators (TBHQ, quercetin, sulforaphane, pyrithione); redox-cycling compounds undergoing prior oxidation and showing lag-period (catechol, o-phenylene diamine); heavy metals (cadmium) working via inhibition of thiol-disulfide exchange and corresponding enzymes; Hsp90 inhibitors/destabilizers showing prolonged lag-period (geldanamycin, TSA); and gedunin. Protein concentration 5.1±0.2 µg per well. To supplement FIG. 5.
Figure 5:
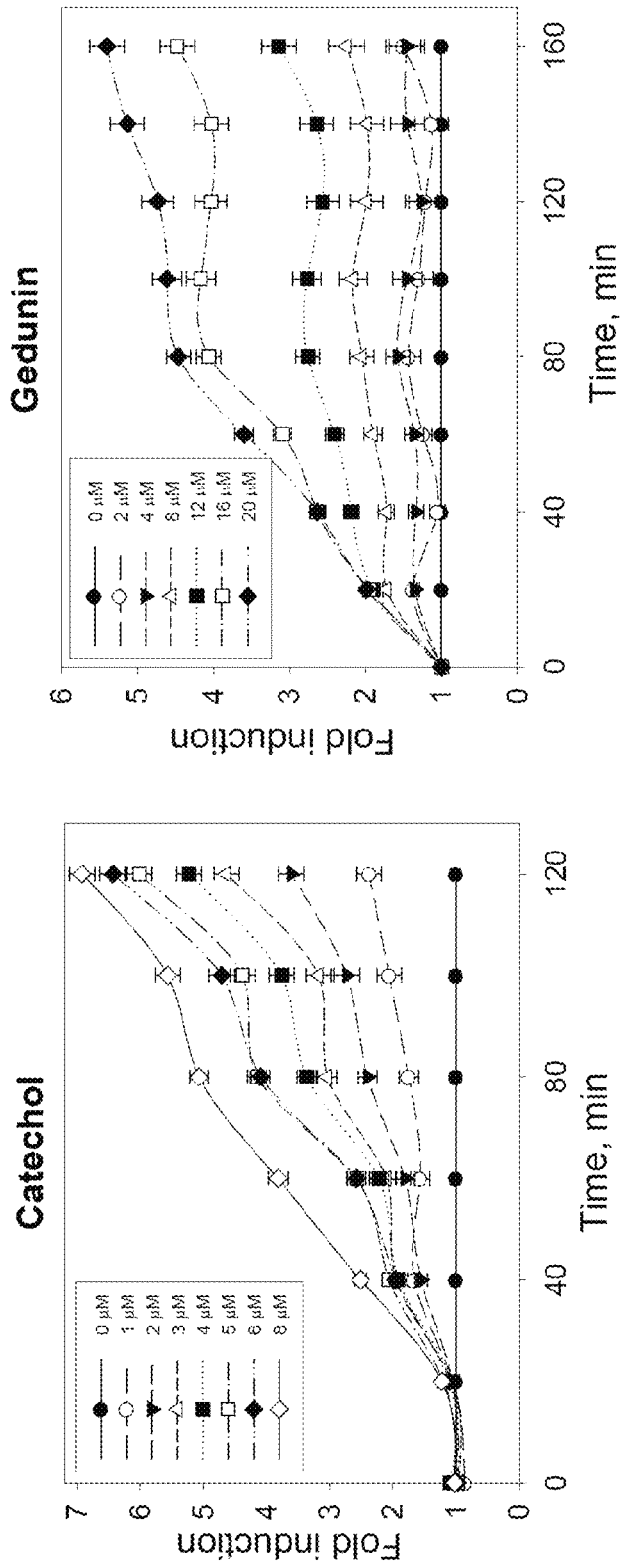
Figure 5:
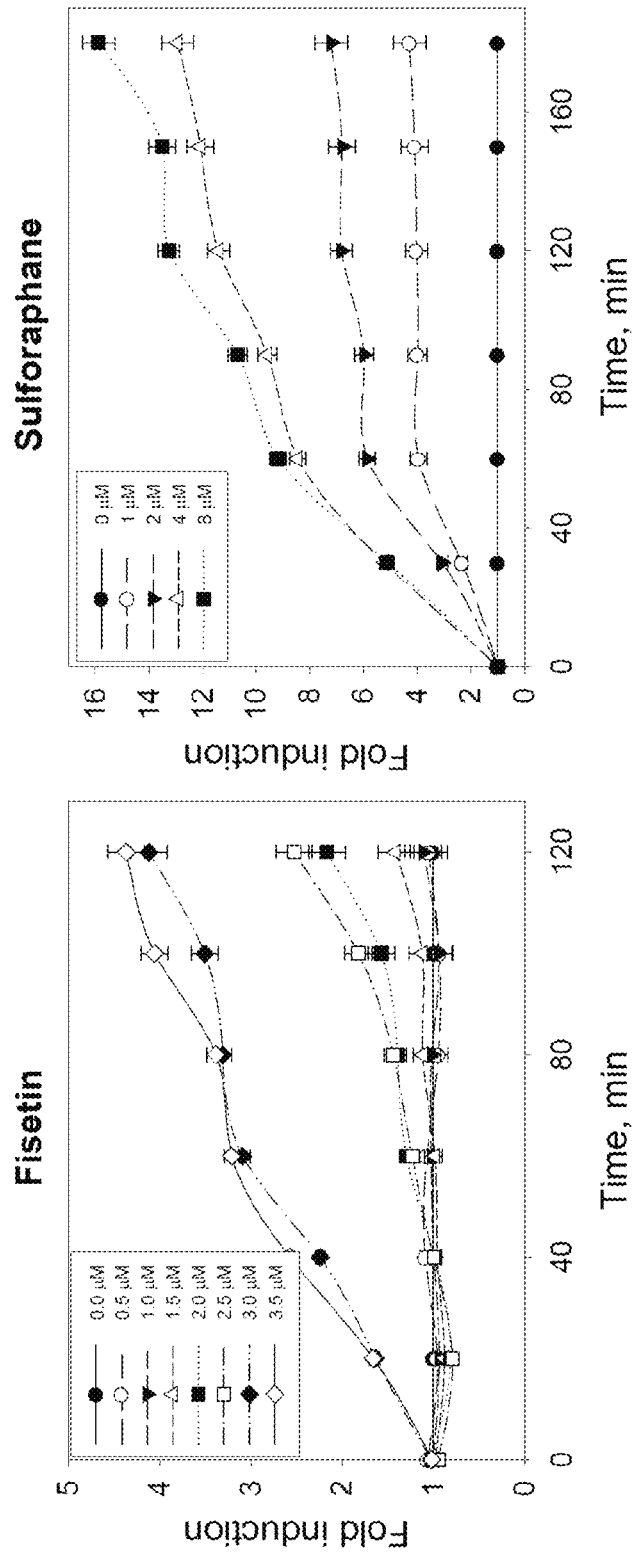
Figure 5:
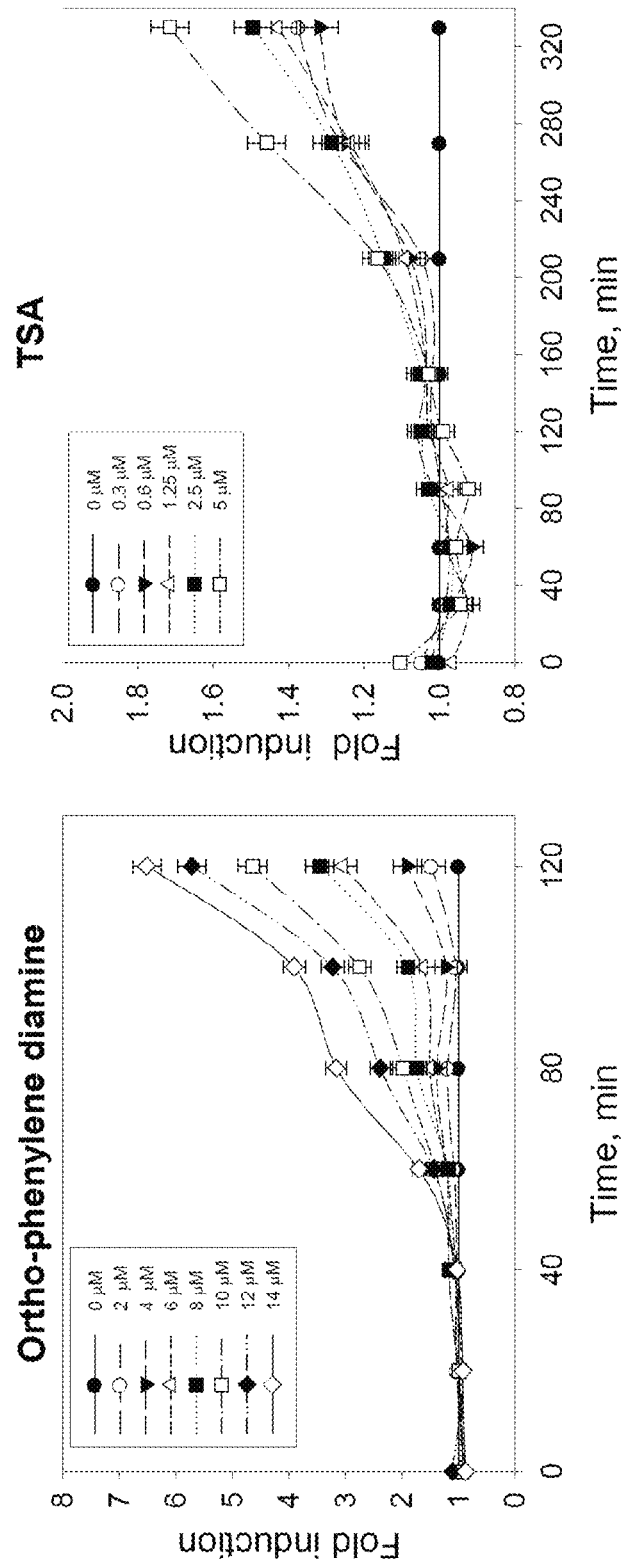
Figure 5:
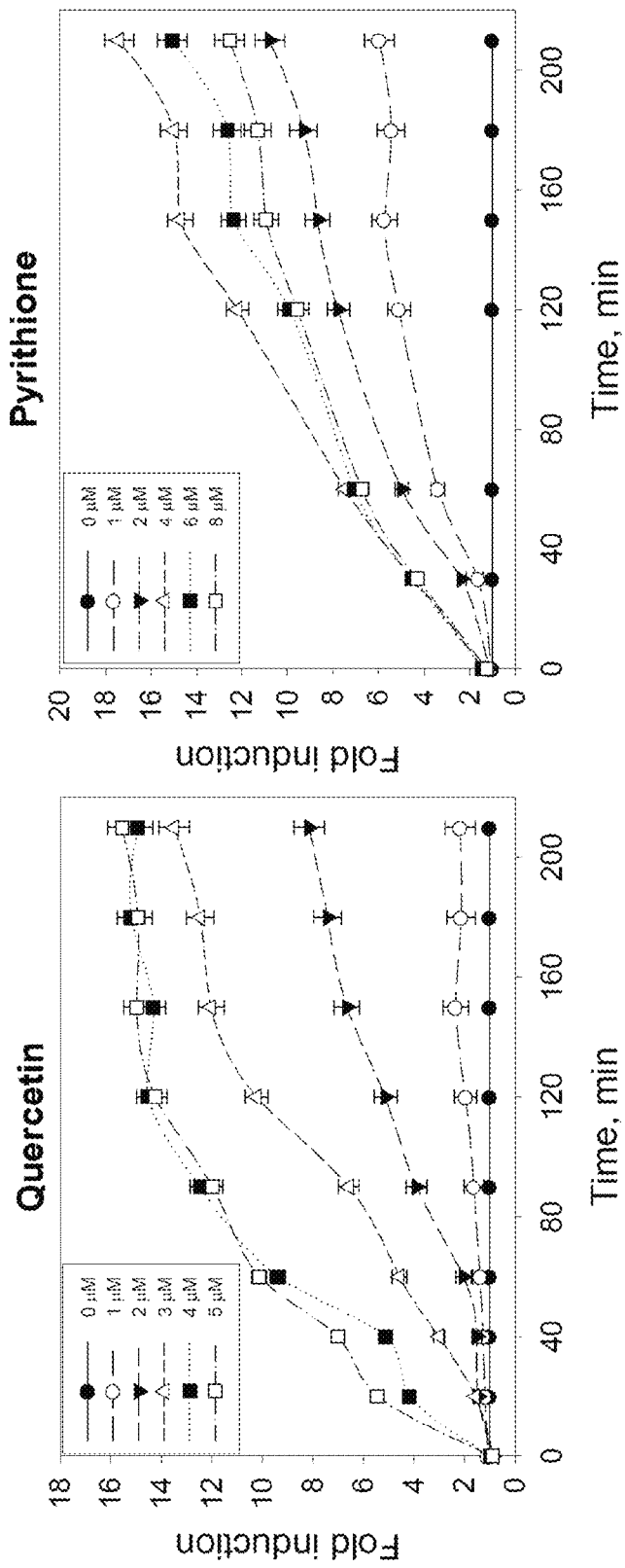
Figure 5:
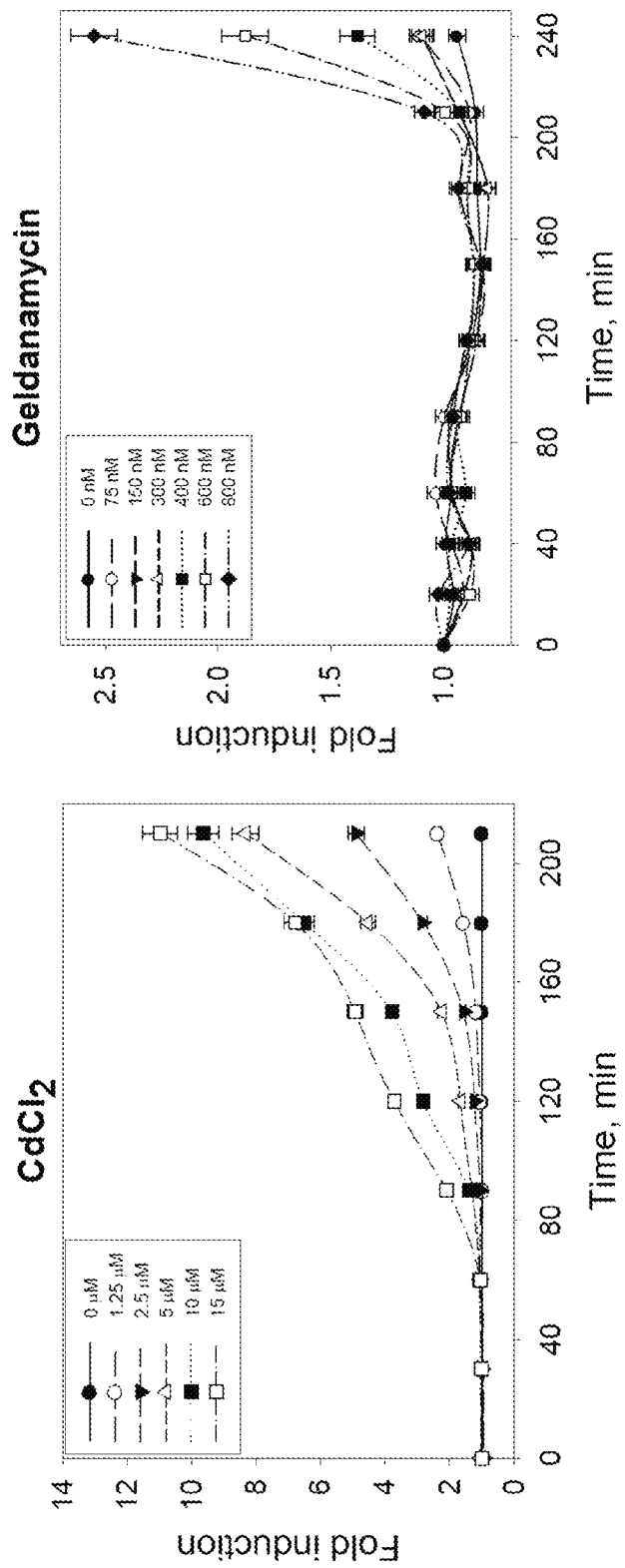

The activation effect observed with geldanamycin, a selective Hsp90 inhibitor was rather modest (2-3 fold in the range of 0.5-1.5 μM) with toxicity dominating at increased concentrations. A characteristic feature of geldanamycin induced Neh2-luciferase stabilization was an extremely prolonged (up to 3 h) lag-period, similar to that observed for the global histone deacetylase inhibitor, TSA (FIG. 5). Of TSA numerous effects, it is also known to lead to acetylation of Hsp90 and inhibition of its chaperone activity. The long lag period of geldanamycin and TSA-induced activation suggest Nrf2 activation as a downstream effect of Hsp90 inhibition. While gedunin has also been described as an Hsp90 inhibitor, the absence of a lag-period in gedunin-induced activation of Neh2-luciferase (FIG. 5) likely reflects direct disruption of Neh2-Keap1 association. The titration behavior is similar to the effect of alkylators of Cys151 in Keap1, except the magnitude of the effect was much lower and the activation plateau is clearly observed at low, non-saturated concentrations of gedunin.

Figure 12A:
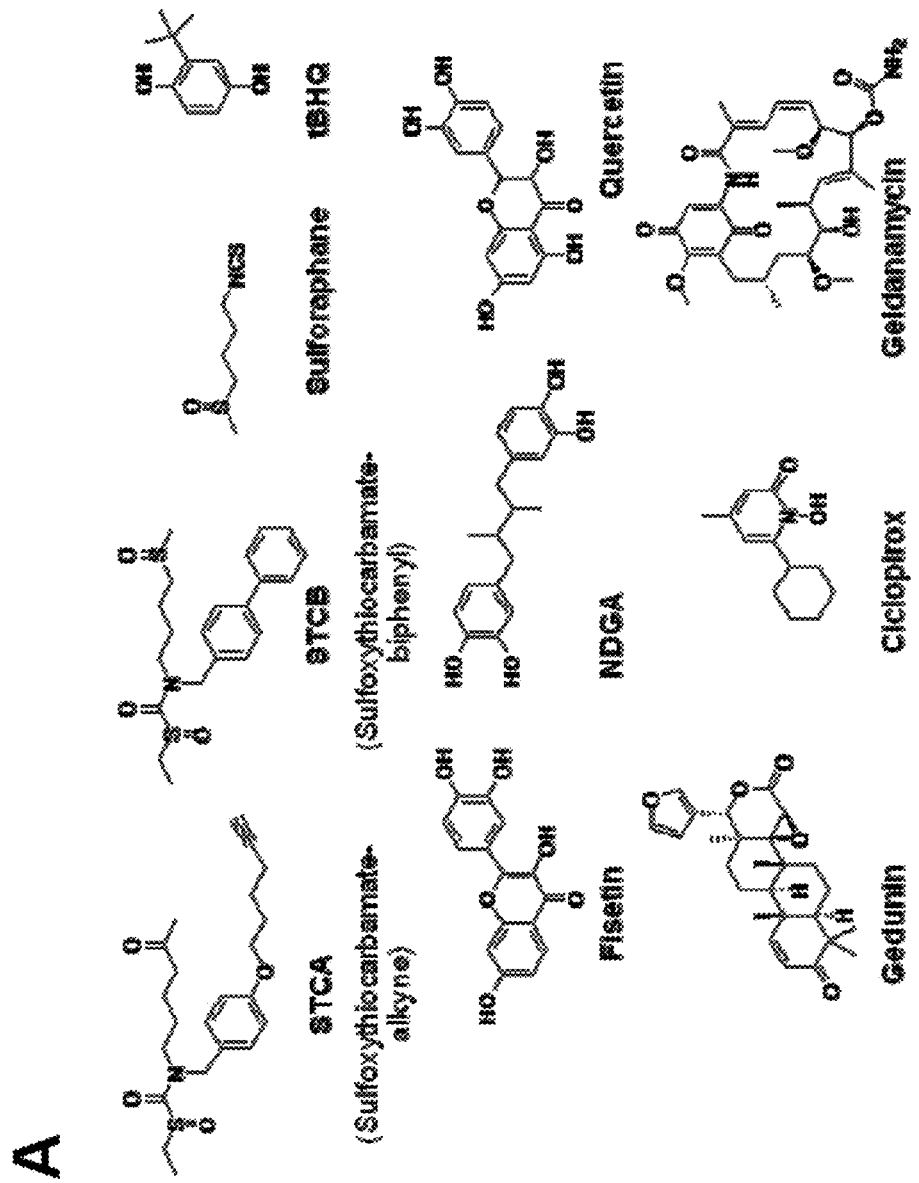
FIG. 12A-B shows the results of Keap1 labeling experiments in the presence of selected hits: only sulforaphane behaves as a potent alkyating agent.
Figure 12B:
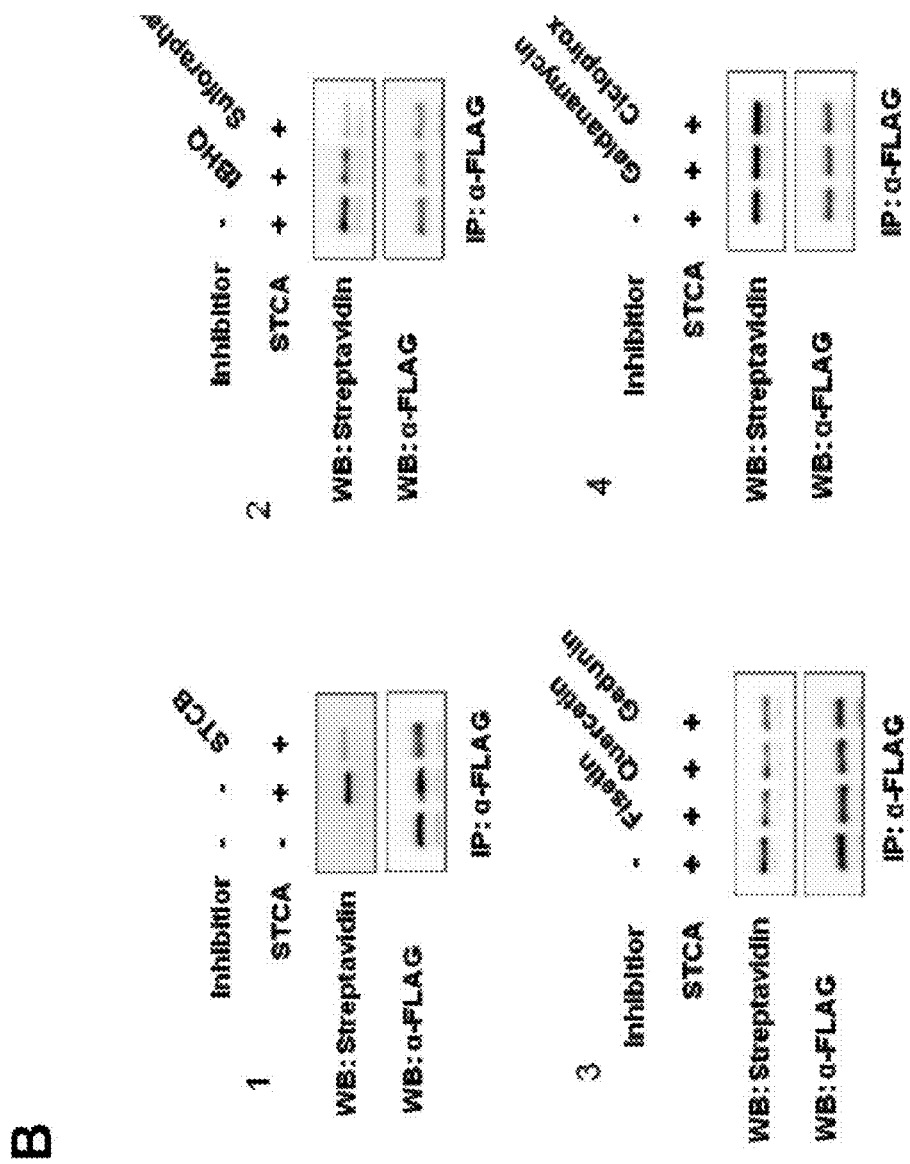
Figure 12C:
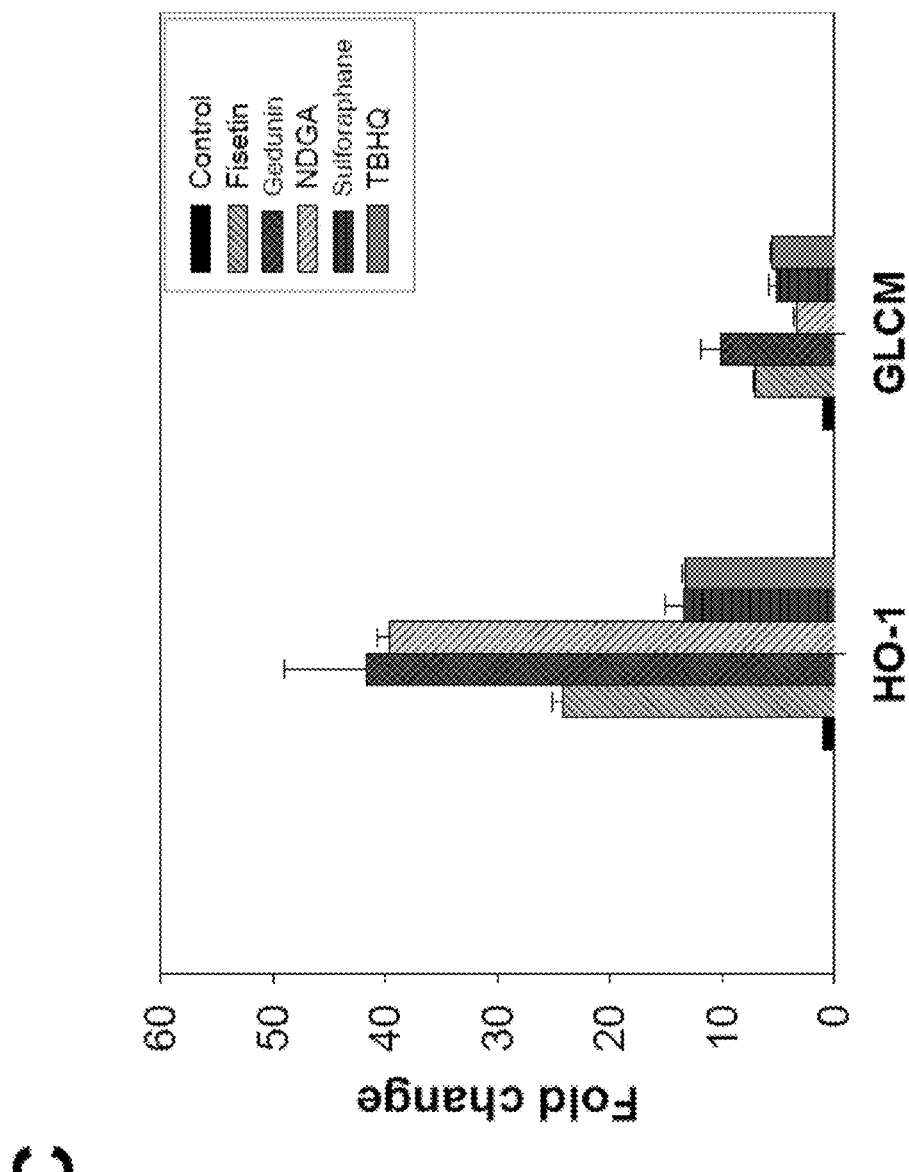
FIG. 12C shows activation of HO-1 and GLCM gene expression.

As an independent approach to test the mechanism of action of selected hits in comparison with the well-known controls we performed Keap1 labeling experiments (FIG. 12A-B) in the presence of sulforaphane (positive control, alkylating agent), TBHQ (positive control, redox cycling compound), fisetin (hit), quercetin (hit), gedunin (hit), geldanamycin (negative control, working via Hsp90) and ciclopirox (negative control, not a hit). All hits induce upregulation of Nrf2 target genes (FIG. 12C). As one may expect only sulforaphane being a potent alkylating agent shows a decent competition for the overexpressed Keap1, while TBHQ, fisetin, quercetin, and gedunin (redox cycling compounds) demonstrate very modest competition (FIG. 12B) indicative of either reversible modification of Keap1 cysteines or preference for particular cysteine residues in Keap1. The labeling approach does not allow one to discriminate between the mechanism of action of the hits, while the Neh2-luc reporter assay clearly shows that all hits exert immediate effects although the time-course patterns are different in shape and magnitude.

Neuroprotective Effects of the Best Hits

Figure 13I:
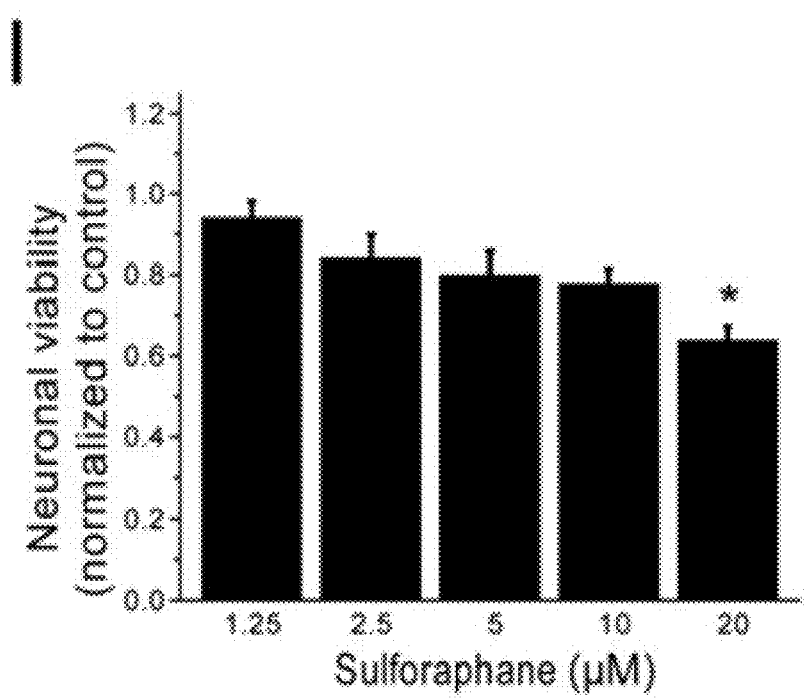
FIG. 13. Control experiments to FIG. 6. A: Intracellular GSH levels in astrocytes treated with Neh2-luc hits. Astrocytes were treated for 24 hr with 5 µM sulforaphane, 20 µM tBHQ, 10 µM NDGA, 24 µM gedunin, or 20 µM fisetin followed by the measurement of GSH in astrocytes. Statistical significance was determined by t-test using Bonferonni correction. *$p<0.05$ vs. control. (B-D) siRNA mediated knockdown of Nrf2. B: Astrocytes were treated with transfection reagent alone (tsx-Ctl), scrambled siRNA (siScrmbl), or siRNA targeted against Nrf2 siNrf2-1,-2, or 3, for 48 hours followed by RNA isolation and real-time PCR analysis. Data are the means±SEM of two independent experiments normalized to control (non-treated) astrocytes. C: Astrocytes were treated with adenoviral vectors containing cDNA for Nrf2 for 24 hours to enhance the detection of Nrf2 protein levels. Following the 24 hour adenoviral transduction, the astrocytes were treated with siRNA transfection reagent alone (tsx-ctl), scrambled siRNA (siScrmbl), or siRNA targeted against Nrf2, siNrf2-1,-2, or 3, for 48 hours followed by cell lysis. Data are representative of three separate experiments. D: Astrocytes were treated ±siRNA (transfection reagent alone (tsx-ctl), scrambled siRNA (siScrmbl), or siRNA targeted against Nrf2 siN-1,-2, or 3) for 24 hour followed by treatment with ±5 µM sulforaphane for 24 hour (total siRNA treatment 48 hour). Data are the means±SEM of three to four experiments per group. Statistical significance was determined by one-way ANOVA followed by post-hoc Dunnett's analysis. $p<0.01$ vs. HCA alone, *$p<0.001$ vs. HCA alone. (E-I) Effect of Neh2-luc activators and established Nrf2 activators on neuronal viability. Immature neurons, 1 DIV, were treated with the Neh2-luc inducers nordihydroguaiarectic acid (E), fisetin (F), gedunin (G), or the established Nrf2 activators tert-butylhydroquinone (TBHQ) (H) or sulforaphane (I) for 24 hours. Data are the means±SEM of three experiments per group. Statistical significance was determined by one-way ANOVA followed by post-hoc Dunnett's analysis. *$p<0.01$ vs. 5 µM TBHQ or 1.25 µM sulforaphane, **$p<0.001$ vs. 5 µM TBHQ.
Figure 14:
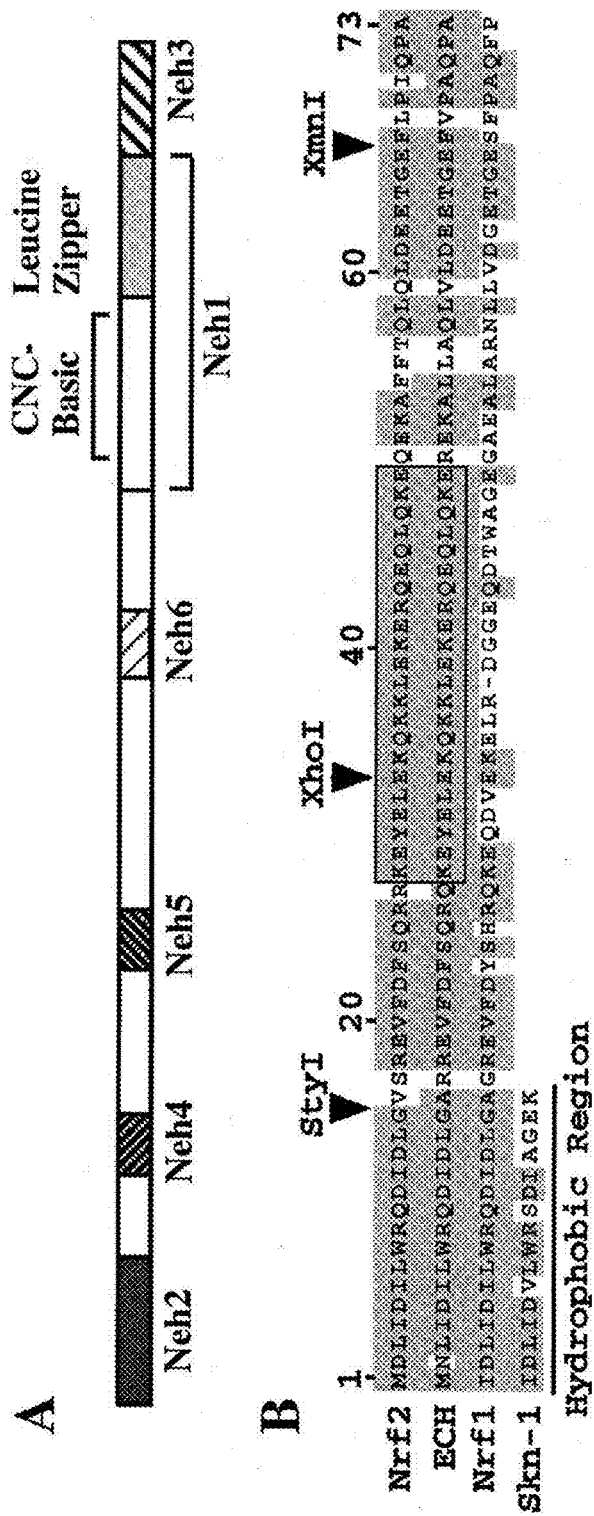
FIG. 14. NEH2 domain. Schematic representation of the regions conserved between chicken and human Nrf2 proteins. (A) Six conserved domains, designated Neh1-Neh6, are found between human and chicken Nrf2. Neh1 corresponds to the CNC region and bZip structure. (B) Sequence homology in Neh2 domains from human Nrf2 (SEQ ID NO: 7), chicken Nrf2 (ECH) (SEQ ID NO: 8), human Nrf1 (SEQ ID NO: 9) and Skn-1 (SEQ ID NO: 10). The amino acid residues conserved between at least two proteins are shaded. The 33 amino-terminal residues, including the hydrophobic region, are conserved among Nrf1, hNrf2, and cNrf2 (ECH); the next 40 residues of Neh2 are rich in hydrophilic residues and specifically conserved between cross-species Nrf2 molecules. The strikingly homologous region, containing hydrophilic residues, is boxed. (▼) Restriction enzyme sites. This entire figure and caption, are FIG. 1 from ITOH et al., *Genes Dev* 13: 76-86 (1999).
Figure 15:
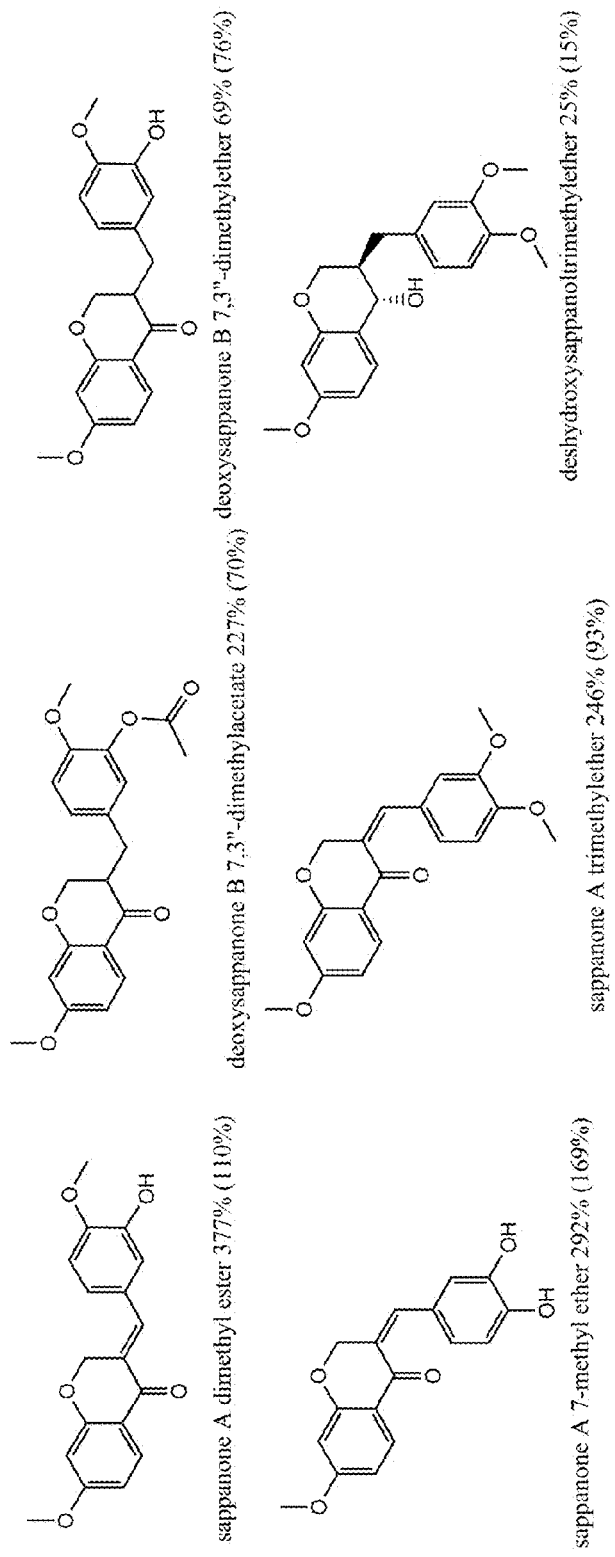
FIG. 15. Hits with sappanone-type scaffold. Activation effects are shown in %% for 16 µM (and 32 µM).
Figure 16:
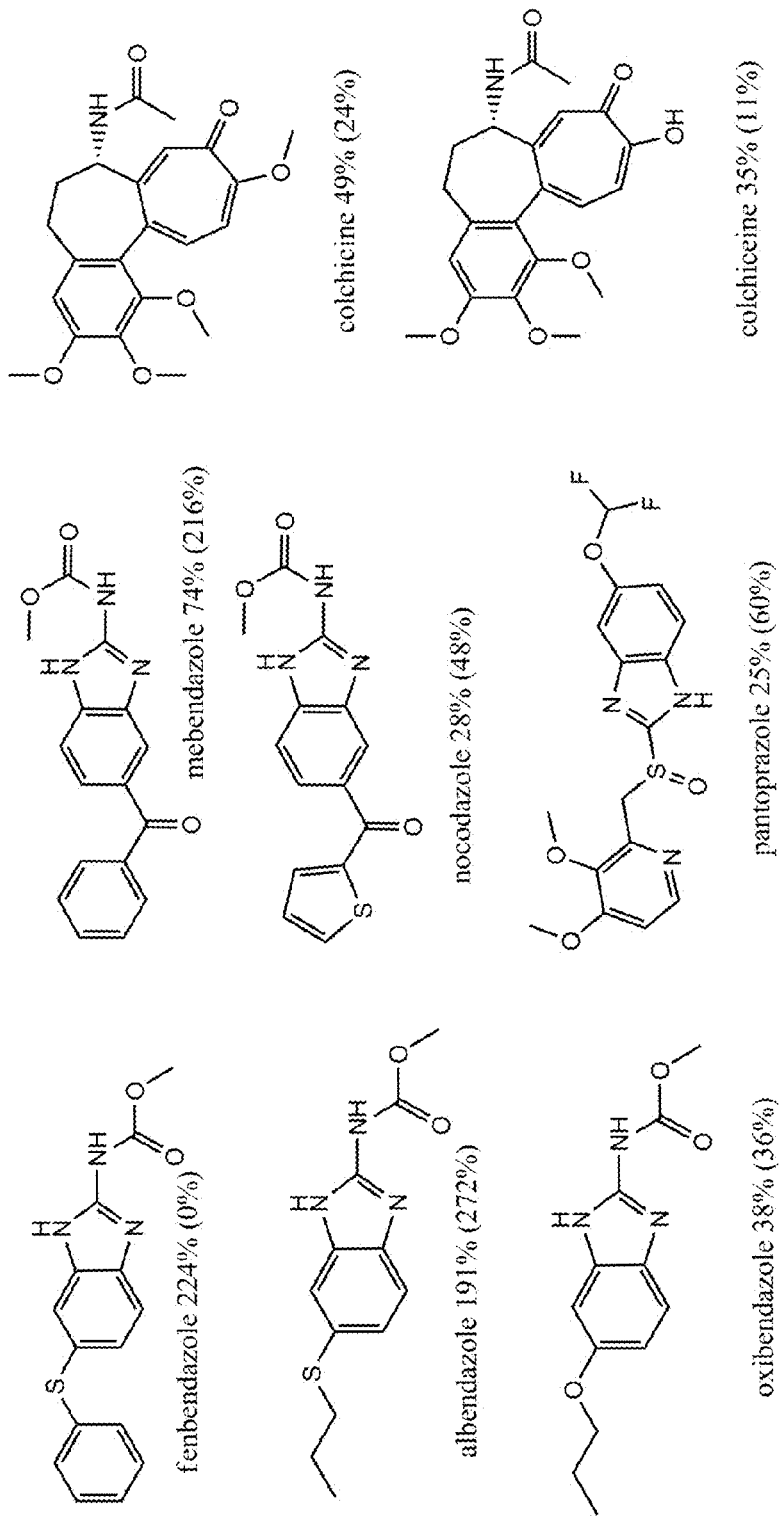
FIG. 16. Hits with benzimidazole-type scaffold. Activation effects are shown in %% for 16 µM (and 32 µM).
Figure 17:
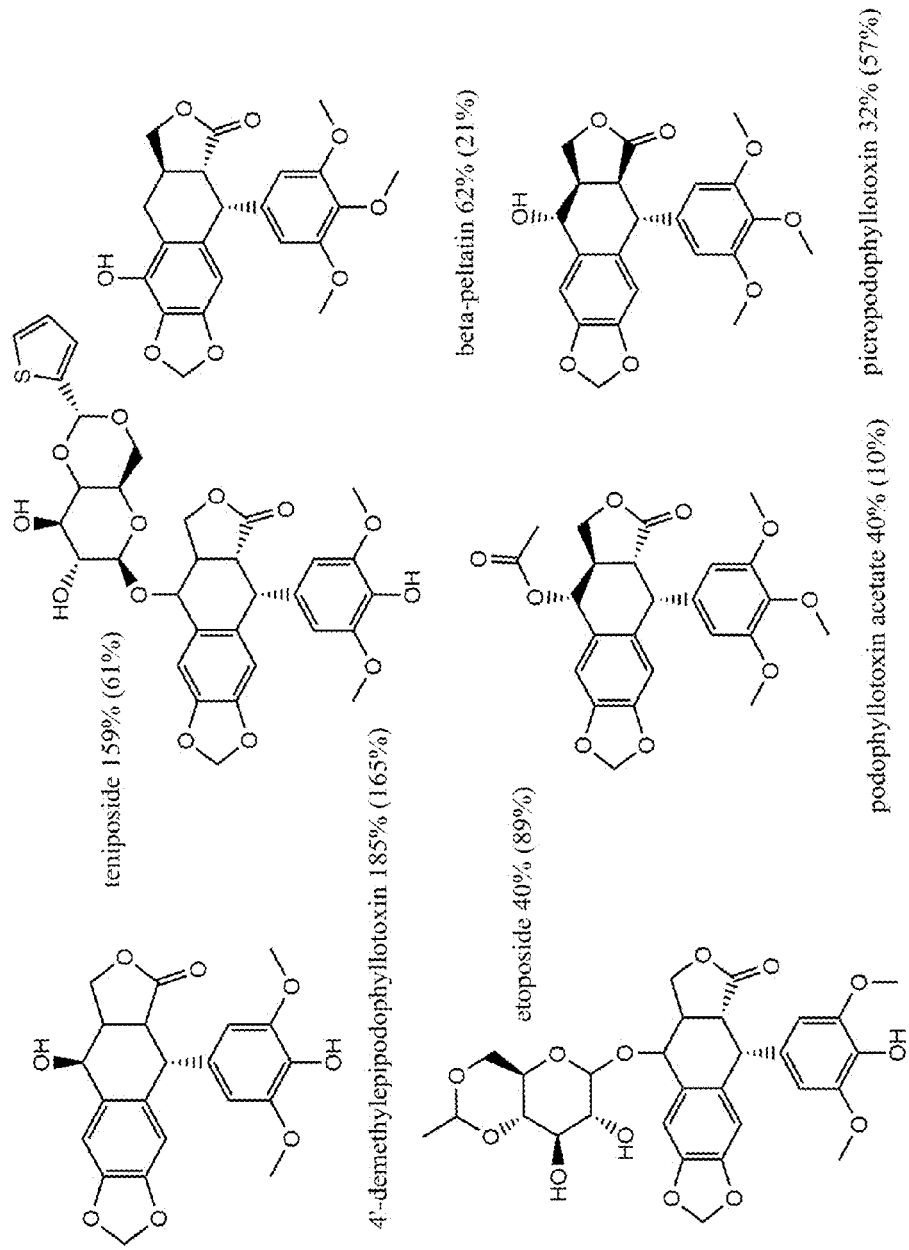
FIG. 17. Other hits with known anticancer properties. Activation effects are shown in %% for 16 µM (and 32 µM).

To confirm that the Neh2-luc activators newly identified from our screen induce a neuroprotective response, we examined the biological effects of these activators on astrocyte-dependent neuroprotection using an astrocyte-neuron coculture model of oxidative stress. Specifically, Nrf2 activation in astrocytes induces non cell autonomous neuroprotection via the transcriptional regulation of genes involved generally in the antioxidant response, including those involved in the biosynthesis, use and export of the major antioxidant glutathione (GSH) (SHIH et al., *J Neurosci* 23: 3394-3406 (2003)). Glutamate or homocysteic acid (HCA, glutamate analog) treatment of immature neurons leads to substantial glutathione depletion in neurons and astrocytes and subsequent oxidative stress-induced death of immature neurons; since astrocytes possess ten times as much glutathione as neurons, HCA treated astrocytes remain viable (HASKEW-LAYTON et al., *Proc Natl Acad Sci USA*, in press (2010)). Thus primary cultured astrocytes were pretreated with NDGA, fisetin or gedunin for 24 hr followed by the addition of adjacent neurons in the presence of the GSH-depleting compound, HCA. Pretreatment of the astrocytes with NDGA, fisetin or gedunin induced significant neuroprotection (FIG. 6 A-C). As expected, all hits induced overexpression of Nrf2-target genes (FIG. 6D-E) and a corresponding increase in HO-1 protein levels (FIG. 6F), the major Nrf2-regulated gene. The treatment of astrocytes with NDGA and gedunin clearly show a boost in GSH, actually higher than classic Nrf2 activators, while fisetin does not show the same level of enhancement and is comparable to what we find with the classical Nrf2 activator TBHQ (FIG. 13A). Fisetin is thought to have multiple targets such as LOX, estrogen receptor and kinases, and therefore its protective effect may be cumulative and off target effects may negatively effect on GSH levels. The absence of a significant effect of fisetin on GSH levels does not point to a Nrf2-independent mechanism, as the Nrf2-target gene HO-1 in astrocytes has also been found to be neuroprotective (VARGAS et al., *J Biol Chem,* 280: 25571-25579 (2005)).

Figure 6J:
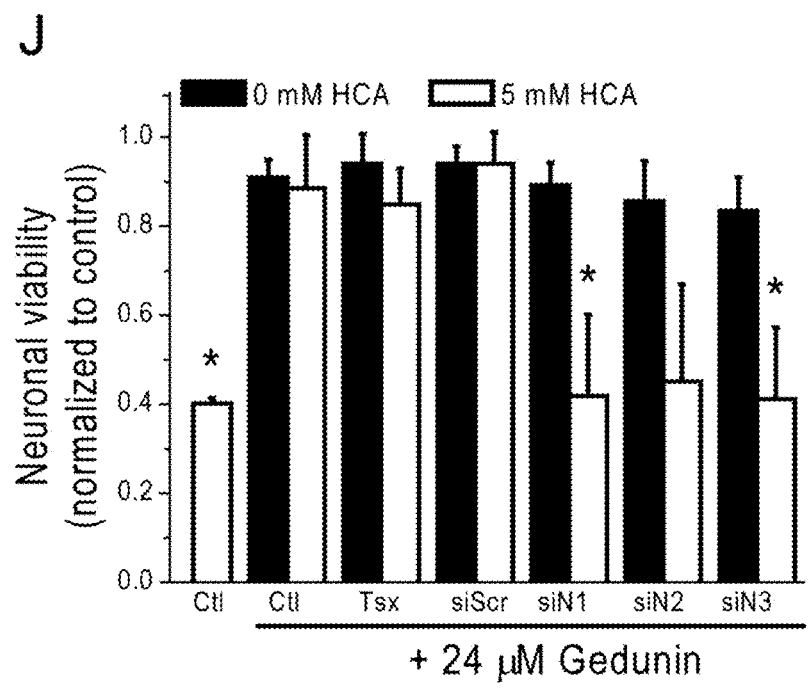
FIG. 6. Nrf2 mediates the astrocyte-dependent protective effect of the Neh2-Luc reporter activators. (A-C) Cultured primary astrocytes were treated for approximately 24 hr with nordihydroguaiaretic acid (A), fisetin (B), or gedunin (C). Immediately following complete wash-off of the treatments, primary immature neurons were plated in the presence or absence of HCA. 48 hr later neuronal viability was determined. (D-E) Astrocytes were treated for 24 hr with 5 µM sulforaphane, 20 µM tBHQ, 10 µM NDGA, 24 µM gedunin or 20 µM fisetin followed by RNA isolation. mRNA for NADPH quinone oxidoreducatase 1 (NQO1) (D) or heme oxygenase-1 (HO-1) (E) was quantified with real-time PCR. (F) Astrocytes were treated for 24 hr with 5 M sulforaphane, 20 µM fisetin, 24 µM gedunin, 5 µM NDGA (NDGA (5)), or 10 µM NDGA (NDGA (10)). Immunoblots show heme oxygenase-1 (HO-1) and β-actin, used as a loading control, immunoreactivity. The last lane is recombinant HO-1. (G) Astrocytes were transfected with transfection reagent alone (Tsx-Ctl), a scrambled siRNA sequence (siScrml), or siRNA targeted against Nrf2 (siNrf2-1, siNrf2-2, siNrf2-3) and treated with 5 µM sulforaphane (SF) for 24 hr (total siRNA treatment 48 hr). Immunoblots show heme oxygenase-1 (HO-1) and β-actin immunoreactivity. The last lane is recombinant HO-1 protein. (H-J) Astrocytes were treated with siRNAs for 24 hr (non-treated-Ctl, transfection reagent alone—Tsx, scrambled siRNA-siScr, or siRNA targeted against Nrf2, siN1, siN2, or siN3), for 24 hr followed by treatment with nordihydroguaiaretic acid (NDGA) (H), fisetin (I), or gedunin (J) for 24 hr (total siRNA=48 hr). Immediately following complete wash-off of the treatments, primary immature neurons were plated+HCA. Statistical significance was determined via one-way ANOVA followed by post-hoc Dunnett's (A-C, H-J) or t-test with Bonferroni correction (D-E). (A-C) *=p<0.05, comparisons are made within 5 mM HCA treatment groups and are vs. 5 mM HCA alone. (D-E)**p<0.01 all groups vs. control. (H-J)*p<0.05, vs Ctl NDGA+HCA, Ctl fisetin+HCA, or Ctl gedunin+HCA. (See FIG. 13 for control experiments: A: increase in glutathione levels; B: efficiency of Nrf2 mRNA knock-down; C: efficiency of Nrf2 protein knockdown; D: positive control for Nrf2 knockdown; E-I: neuronal viability in the presence of the studied compounds).

To confirm that the astrocyte-dependent neuroprotective effects were specific to the activation of Nrf2, astrocytes were pretreated with siRNAs targeted against Nrf2. Three separate Nrf2 siRNA sequences lead to reduced Nrf2 mRNA and protein levels (FIGS. 13B,C) and reduced levels of Nrf2-regulated HO-1 protein levels (FIG. 6G). Sulforaphane, a canonical Nrf2 activator, known to enhance astrocyte-dependent Nrf2-mediated neuroprotection was used as a positive control. Consistent with prior results, Nrf2-knockdown with the Nrf2 siRNAs completely abrogated the sulforaphane-induced astrocyte-specific neuroprotection (FIG. 13D). Additionally, the protective effects of NDGA, fisetin or gedunin were also abrogated with Nrf2 knockdown (FIG. 6H-J). We do not believe that this reversal reflects the manifestation of toxic properties of the compounds, as Nrf2 knockdown in the absence of oxidative stress did not lead to death in fisetin, NDGA, or gedunin treated cocultures.

As electrophiles, many of the canonical Nrf2 activators are potential neurotoxins. Even a low level of electrophilic stress would not be ideal for many neurological conditions where oxidative stress is a contributor to disease pathology. Thus the identification of non-electrophilic activators of Nrf2 is a high priority. Importantly, in contrast to the neurotoxic effects of the canonical Nrf2 activators such as TBHQ, the hits from our screen (NDGA, fisetin or gedunin) did not induce toxicity in isolated neurons using a sensitive assay of neuronal vulnerability (FIG. 13 E-I). It is worth noting that both NDGA and gedunin identified in this work as effective Nrf2 activators are key components of herbal medicines used for centuries by native Americans (chaparral) and Indians (neem tree), respectively. These results demonstrate that the Neh2-luc reporter system can be used to identify potent and safe neuroprotective activators of the Nrf2 adaptive response.

Previous reporters of Nrf2 activation have utilized the antioxidant response element (ARE) fused to coding regions of firefly luciferase or human alkaline phosphatase in vitro or in vivo. The ARE-GFP construct was used to screen Spectrum library and 45 hits were identified (SHAW et al., *UK Patent Application* #0918626.3, Priority Date (Oct. 24, 2008), Publ Date (May 5, 2010)). The Are-based reporters allow monitoring of 24 h and more delayed effects of antioxidant response induced by Nrf2 stabilization. We have constructed a new reporter system that allows immediate monitoring of drug-induced Nrf2 stabilization in the form of Neh2-luciferase fusion protein. The reporter appears to be a physiological surrogate for Nrf2 based on several observations:

1) Keap1 overexpression inhibits the reporter activity, while Keap1 depletion stabilizes the reporter (FIG. 2);

2) Canonical activators of Nrf2, which have been shown to act by alkylating Keap1, lead to expected increases in the Neh2-luciferase activity and protein (FIG. 8B and FIG. 4C);

3) Representatives of all previously known classes of Nrf2 activators as well as the majority of ARE-GFP screen hits (SHAW et al., *UK Patent Application* #0918626.3, Priority Date (Oct. 24, 2008), Publ Date (May 5, 2010)) were identified in the Spectrum library using the novel reporter, further validating the assay (FIG. 3);

4) Novel activators of Nrf2 defined in this screen protect neurons from oxidative death via an Nrf2-dependent mechanism in astrocytes (FIG. 6).

The power of the new reporter allowed us to discriminate between direct and indirect effects on reporter stabilization induced by compounds tested in HTS, and for the first time identify gedunin as a direct activator of Nrf2. Recent studies suggest that gedunins are potent Hsp90 inhibitors (BRANDT et al., *J Med Chem,* 51: 6495-6502 (2008)). Celastrol, a quinone methide triterpenoid, is known as Hsp90 inhibitor (ZHANG et al., *J Biol Chem,* 284: 35381-35389 (2009); ZHANG et al., *Mol Cancer Ther,* 7: 162-170 (2008)) as well, and its derivative, dihydrocelastrol, was also found as a modest hit in the screen. Based only on structural similarities between gedunin and celastrol, it is possible that gedunin utilizes a similar mechanism of action via disrupting the interaction between Hsp90 and Cdc37, the co-chaperone providing a bridge between Hsp90 and client tyrosine kinases (ZHANG et al., *J Biol Chem,* 284: 35381-35389 (2009); ZHANG et al., *Mol Cancer Ther,* 7: 162-170 (2008)), which being detached from the Hsp90 complex undergo fast inactivation (usually within 40-45 min). Of note, triterpenoids have been described as Nrf2 activators using ARE-reporter mice and NQO1 induction levels (YATES et al., *Mol Cancer Ther,* 6: 154-162 (2007)), and induce neuroprotection in a transgenic model of Huntington's disease (STACK et al., *Free Radic Biol Med.,* 49:147-158 (2010)). Withanolides, closer analogs of gedunins, have been long known as inducers of NQO1 (DINKOVA-KOSTOVA et al., *Methods Enzymol,* 382: 423-448 (2004)), and are also known to disrupt Hsp90-Cdc37 interaction (YU et al., *Biochem Pharmacol,* 79: 542-551 (2010)).

If gedunin works via the same mechanism as the above compounds, we should observe the delayed effect of Hsp90 down-regulation with all three compounds, e.g. gedunin, geldanamycin and TSA. However, the latter two show 3 h lag-period in reporter activation, in contrast to the immediate effect induced by gedunin (FIG. 5). We may speculate that the direct effect of gedunin originates from its competition with Nrf2 for Keap1 based on the comparatively modest activation amplitude and observed plateau in the time-course of reporter activation (FIG. 5). This is in contrast to alkylating agents which drive the system to the maximum activation linearly (see quercetin, catechol). The plateau is a characteristic of re-equilibration of the system with reversible binding, or in other words gedunins may bind Keap1 reversibly. It is tempting to speculate that gedunins compete with Nrf2 for Keap1 binding: the possibility to design mild peptide-type inhibitors displacing Nrf2 from Keap1 like p62 does in vivo (Komatsu et al.) has been discussed in the paper with the resolved crystal structure of Neh2-Keap1 DGR (TONG et al., *Mol Cell Biol.,* 27: 7511-7521 (2007)). This speculation is supported by computer modeling: gedunins fit perfectly into the same Keap1 binding pocket as Nrf2 (FIG. 7A) closely following the bending of the 83FEGTE79 portion of the Nrf2 peptide (FIG. 7B).

An important unanswered question is the mechanism of "switch" effect demonstrated for our best hits, fisetin and NDGA. The time-course of NDGA and fisetin clearly shows that they exert an immediate effect upon addition to the reporter cell line, therefore they act "as is", without prior chemical modification. Both NDGA and fisetin have adjacent hydroxy-groups on a freely rotating phenyl ring. We could suggest that these adjacent hydroxy groups lead to reduction of a critical disulfide bond. However, there is some doubt that fisetin and NDGA work via this mechanism since the flavones are strong reducing agents capable of immediate reduction of dithionitrobenzoate, a model disulfide, while NDGA is not. In addition, luteolin, a flavone with potent reducing properties, with 3',4'-dihydroxy-phenyl group present in fisetin, but hydroxyl group in position 5, not 3, is a very poor Nrf2 activator. Moreover, catechol, being a very potent reducing agent, does show a 20 min lag-period, which may reflect initial "priming", most likely oxidation that results in formation of its form capable of alkylating Keap1. The fact that luteolin and catechol do not behave the same way argues against this potential mechanism and points out to the special structural requirements for a "switch" mechanism of Nrf2 activation.

A common and intriguing feature of our most promising hits, fisetin and NDGA, is their steep concentration response, reminiscent of a ligand binding to a receptor. Of note, a common feature of these hits is that they all have been reported to act as inhibitors of protein tyrosine kinases, and NDGA in particular was reported to target IGF1-R kinase. We also identified genistein (100% reporter activation), which is well known for targeting this class of enzymes. Phosphorylation of Tyr141 in Keap1 is catalyzed by an unknown protein tyrosine kinase and is critical for Keap1 stability (JAIN et al., *J Biol Chem* 283: 17712-17720 (2008)). Protein tyrosine kinases are also known to be stabilized by Hsp90, inhibitors of which also came out in our screen as hits.

Figure 7:
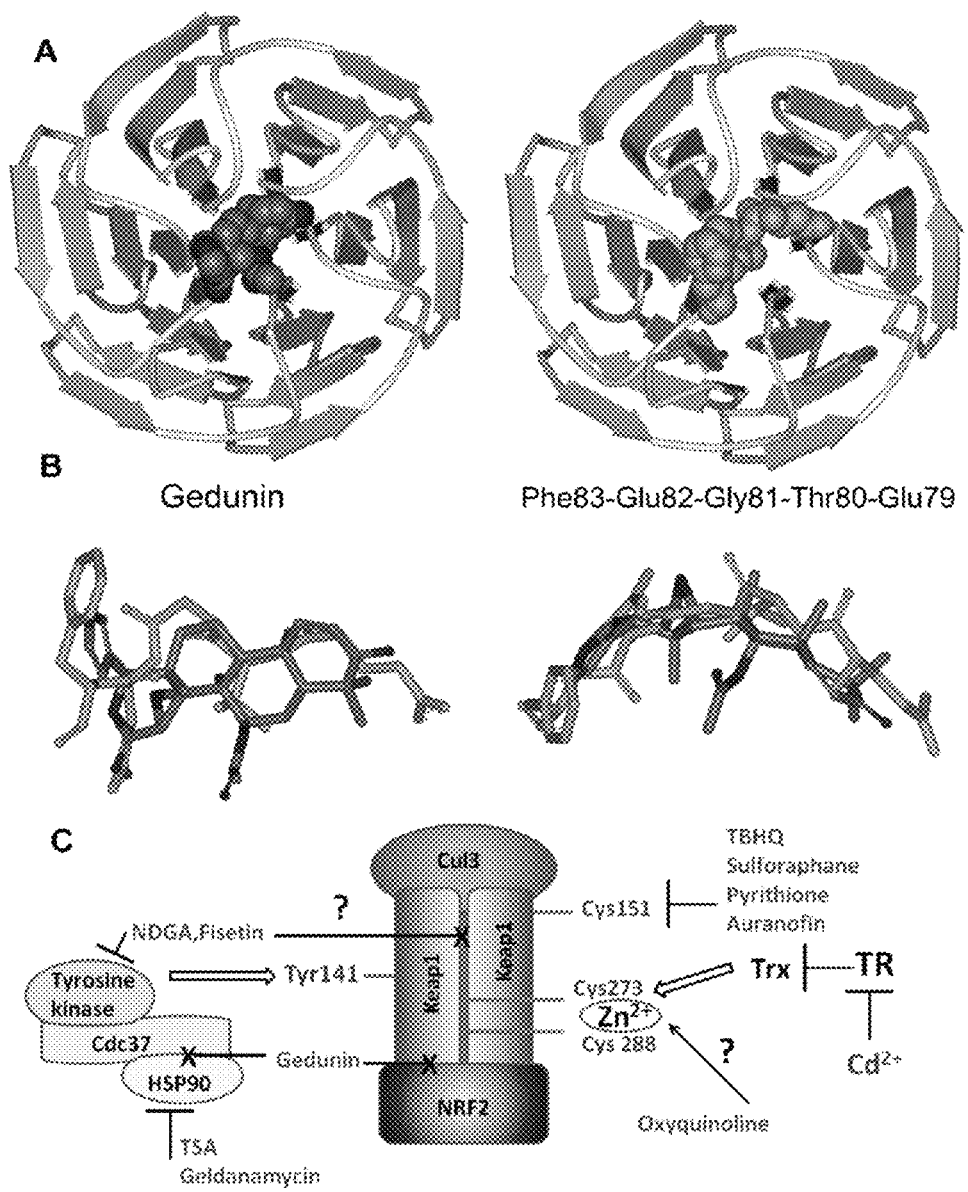
FIG. 7. Schematic representation of different mechanisms of Nrf2 level regulation and plausible mechanism of gedunin action. A: docking mode of gedunin in comparison with the binding mode of Neh2 portion into Keap1, and B: overlap between Neh2 peptide and gedunin, from perpendicular views. C: Hypothetic modes of Nrf2 level regulation (see text for details).

The analysis of kinetics of individual hits leads to the model scheme of Nrf2 regulation shown in FIG. 7C. A key role is played by Keap1 Cys151, 273, 288, which modification with alkylating agents causes a dramatic change in Keap1 conformation leading to Nrf2 stabilization. If Keap1 in vivo has a zinc atom in the structure, we may hypothesize that the small planar $Zn^{2+}$ chelators identified in HTS may target and destabilize the thiol pair in Keap1 as well. The delayed effect of cadmium may reflect the inhibition of thioredoxin reductase/thioredoxin system eventually compromising the redox status of key cysteines in Keap1. Regulation of Keap1 stability via Hsp90-Cdc37-tyrosine kinase interaction is upstream of immediate activation pathways. Hsp90 is a target for TSA and geldanamycin, while NDGA and fisetin inhibit tyrosine kinase activity. Gedunin, in addition to intercalation into the Hsp90-Cdc37 interface, exerts an immediate effect on Nrf2 stabilization, possibly by disrupting Nrf2-Keap1 interaction. With respect to fisetin and NDGA, we also cannot rule out a possibility of targeting an unknown site at the interface of Keap1 subunits (FIG. 7C) resulting in an immediate change in Keap1 conformation and stabilization of Nrf2, because the scaffold of fisetin closely resembles those of the hits generated by the virtual screen in (WU et al., *Chem Biol Drug Des*, 75: 475-480 (2010)) (FIG. 10).

Canonical activators of Nrf2 such as TBHQ, isothiocyanates, and the recently identified AL-I (HUR et al., *Chem Biol,* 17, 537-547 (2010)) appear to act by modifying key cysteines in Keap1, the negative regulator of Nrf2 stability. A major potential problem with electrophile activators of Nrf2 is their ability to induce toxicity, particularly in cells vulnerable to redox stress such as neurons afflicted by ischemia or neurodegeneration. The challenge is to find Nrf2 activators which do not add to the overall oxidative load, and the novel reporter provides a valuable resource for future developments towards such medications. Here we identify a number of novel Nrf2 activators that are non-toxic to neurons over the range of concentrations optimal for reporter activation (FIG. 13E-I).

Activation of Nrf2 by TBHQ, sulforaphane, or CDDO-triterpenoid plays a key role in the antioxidant defense of the central nervous system and has been shown to be important for neuroproteciton in several acute and chronic neuropathological conditions such as stroke, intracerebral hemorrhage, Parkinson's disease, Huntington's disease and amyotrophic lateral sclerosis, and yet Nrf2 activators are only now making their way into the clinic (SHIH et al., *J Neurosci,* 25: 10321-10335 (2005); CHEN et al., *Mol Cell,* 34: 663-673 (2009); VARGAS et al., *J Neurosci,* 28: 13574-13581 (2008)). These findings highlight the biological and clinical importance of a real-time assay for screening and design of Nrf2 activators. The newly developed Neh2-luciferase reporter is perfectly suitable for HTS purposes, for studying the mechanistic details of drug action, and by analogy with HIF ODD-luc system (SAFRAN et al., *Proc Natl Acad Sci USA,* 103: 105-110 (2006)), we are confident that the new reporter may be successfully used for in vivo imaging of Nrf2 activators in animals.

Genetic antioxidant responses activated by electrophiles are currently monitored via the use of reporters such as firefly luciferase, human alkaline phosphatase, or GFP driven by a canonical antioxidant response element (ARE). Activators of this pathway lead to the stabilization of Nrf2 and induction of dozens of genes that have been shown to prevent cancer, neurodegeneration, proinflammatory states, and combat atherosclerosis. There is a lack of compelling bioassay to ensure real-time monitoring of antioxidant response. We present a novel reporter based on a principle different than the widely used ARE-luciferase. The newly developed reporter constitutively expresses the Neh2 domain of Nrf2 fused to firefly luciferase. The steady-state concentration of Nrf2 (as represented by Neh2 luciferase) established in cells can be manipulated by the addition of compounds affecting the individual steps controlling the Nrf2 stability. The novel reporter allows monitoring the antioxidant response in real-time, right after drug administration, and is suitable both for high throughput screening and elucidation of the mechanism of drug action. The power of the new reporter is illustrated by its application for screening of Spectrum library followed by real-time monitoring of action of selected hits: in addition to the identification of new Nrf2 activators, we for the first time make an insight into the mechanistic details of their action and offer a strategy to discriminate between the action of direct activators such as alkylating agents and those requiring additional transformation steps such as prior oxidation (catechols and diamines) or manipulation of upstream regulatory pathways (via Hsp90 inhibition). Gedunins and their structural analogs were identified as a novel pharmacological class of Nrf2 activators. We also provide biological evidence for Nrf2-dependent neuroprotective roles played by newly identified Nrf2 activators—fisetin, nordihydroguaiaretic acid, and gedunin—in an established model of oxidative stress in neuron-astrocyte coculture.

The present invention also provides a method for the prevention or treatment of a disease characterized by insufficient or overabundance of NRF2 activity in a subject, by administering to the subject a composition comprising a therapeutically effective amount of a modulator of NRF2 and a pharmaceutically acceptable excipient.

In another aspect, the present invention provides pharmaceutically acceptable compositions which comprise a therapeutically-effective amount of one or more of the modulators of NRF2, as described above, formulated together with one or more pharmaceutically acceptable excipients. In another aspect, the present invention provides pharmaceutically acceptable compositions which comprise a therapeutically-effective amount of one or more of the modulators of NRF2, as described above, formulated together with one or more pharmaceutically acceptable excipients and other therapeutically effective medications known in the art allowing for but not limited to combination therapies to improve overall efficacy of each individual therapeutic or to limit the concentration of either therapeutic to avoid side effects and maintain efficacy. The active ingredient and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

A therapeutically effective amount of the pharmaceutical composition of the present invention is sufficient to treat or prevent a disease characterized by symptoms comprising insufficient or overabundance of NRF2 activity. The dosage of active ingredient(s) may vary, depending on the reason for use and the individual subject. The dosage may be adjusted based on the subject's weight, the age and health of the subject, and tolerance for the compound or composition.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subjects's stomach may be increased by the addition of a disintegrant to the composition. Disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

EXAMPLES

The present description is further illustrated by the following examples, which should not be construed as limiting in any way. The contents of all cited references (including literature references, issued patents, published patent applications as cited throughout this application) are hereby expressly incorporated by reference.

Cell Lines, Primary Neuronal and Astrocyte Cultures

Human neuroblastoma SH-SY5Y cells were transfected with 1 mg of pcDNA3-Neh2LUC10, pcDNA3-ODDLUC8, pcDNA3-LUC3, and ARE-LUC/pcDNA3 (5:1) by using Lipofectamine_2000 (Invitrogen). Transfected cells were grown in the presence of 500 mg/ml Geneticin (GIBCO-Invitrogen) on DMEM/F12+ GlitaMAX (Dulbecco's modified Eagle medium Nutrient Mixture F-12 (Ham)(1:1) 1×, GIBCO 10565) medium.

Primary neuronal and astrocyte cultures. All animal procedures were performed according to protocols approved by the Institutional Animal Care and Use Committee of the Weill Medical College of Cornell University. Primary astrocyte cultures were prepared from the cerebral cortices of Sprague-Dawley rat pups (P1-3). Primary neuronal cultures were prepared from the forebrains of Sprague-Dawley rat embryos (E17). Following removal of the meninges, the cultures were dissociated as described by Ratan et al. (RATAN et al., *Methods Enzymol*, 352: 183-90 (2002)). In brief, the brain tissue was dissociated using the protease Papain (Worthington Biochemical Corp). Astrocyte cultures were then seeded at a low density (15,000/mL) on Primaria™ plates (BD Falcon) and grown for ~2 weeks to confluency in minimal essential medium (MEM—Invitrogen) supplemented with 10% horse serum and 25 units/ml penicillin plus 25 g/ml streptomycin. Upon reaching confluency the astrocytes were treated with 8 µM cytosine-D-arabinofuranoside (Ara-C), a mitotic inhibitor, for ~3 days to kill off contaminating cells. The astrocytes were used for experiments at 2-3 weeks in culture. GFAP staining confirmed greater than ~95% purity of the astrocyte cultures. Neuronal enriched cultures were plated at a density of 500,000 cells/mL directly on top of a confluent monolayer of astrocytes in MEM supplemented with 10% horse serum, 2.5% fetal bovine serum and 25 units/ml penicillin plus 25 g/ml streptomycin. Under these conditions, the cultured immature neurons lack glutamate receptors and are therefore not susceptible to glutamate-mediated excitotoxicity. (RATAN et al., *Methods Enzymol*, 352: 183-90 (2002))

Reporter Plasmid Construction.

DNA fragment encoding 1-97 a.a. residues of Neh2 domain of NRF2 was the product of PCR with a cDNA template obtained from total RNA isolated from SH-SY5Y cells by using NucleoSpin RNAII kit (Macherey-Nagel) and used for cDNA synthesis by SuperScript III First-Strand Synthesis System for RT-PCR (Invitrogen). Neh2 fragment flanked with HindIII and NarI sites was amplified using Advantage 2 polymerase mix (Clontech) and the following primers

```
HINDNRF:
                                    (SEQ ID NO: 1)
CCCAAGCTTGGATCCGAATTCGCCACCATGATGGACTTGGAGCTGCCGC
CGCC,
and NARNRF:
                                    (SEQ ID NO: 2)
TAGAATGGCGCCGGGCCTTTCTTTATGTTTTTGGCGTCTTCACTGGTTT
CTGA.
```

Then it was inserted into HindIII and NarI sites of pGL3-control (Promega) to obtain pGL3NEH2LUC. The HindIII-XbaI DNA fragment of pGL3NEH2LUC encoding fusion protein Neh2-luciferase was cloned into corresponding sites of pcDNA3 (Invitrogen) to obtain pcDNA3-Neh2LUC10. The HIF ODDLUC encoding plasmid pcDNA3-ODDLUC8 was constructed as described previously (SMIRNOVA et al., Chem Biol, 17: 380-391 (2010)). pcDNA3-LUC3 encoding plain luciferase was made by insertion of HindIII-XbaI fragment of pGL3-control into HindIII-XbaI sites of pcDNA3. The ARE-luciferase construct contained an ARE promoter consensus sequence as derived from the human NADPH quinone oxidoreductase gene (5'CTCAGCCTTC-CAAATCGCAGTCACAGTGACTCAGCAGAATC-3', SEQ ID NO: 3), upstream of a luciferase reporter (MOEHLENKAMP et al., Arch Biochem Biophys, 363: 98-106 (1999)).

HTS Optimization and SAR Analysis

The assay was optimized for HTS format to provide Z values above 0.7. SH-SY5Y-Neh2-luc cells were plated into 384 well, white, flat-bottom plates at 7000 cell/well in 30 µl serum and incubated overnight at 37° C., 5% CO2. The next day compounds were added to two final concentrations of 16 µM and 32 µM, plates were incubated for 3 hr at 37° C., and luciferase activity was measured using SteadyGlo™ reagent (Promega). Each plate had two internal standards, TBHQ (100%) and DMSO (0%). The reporter activation (%) was calculated as a ratio (L-LDMSO)/(LTBHQ-LDMSO). Hits were defined as those greater than 25%. HTS of 2,000 compounds was performed at Rockefeller University HTS Resource Center. A total of 224 hits from the initial screen have been tested in duplicate, and 210 were confirmed. Classification into structural clusters has been done manually. The line expressing wild-type luciferase under the same promoter was used to evaluate the effect of all compounds from Spectrum library on luciferase activity. None were found to inhibit or enhance the luciferase activity under the experimental conditions, while 46 compounds were found to be toxic at 3 h incubation and were excluded from consideration. The previously described HIF1 ODD-luc reporter line (SMIRNOVA et al., Chem Biol, 17: 380-391 (2010)) was used as a control for specificity.

Summary information on the assay is found in the following table:

Small Molecule Screening Data.

| Category | Parameter | Description |
|---|---|---|
| Assay | Type of assay | Reporter gene, luciferase |
| | Target | Nrf2-Keap1 complex |
| | Primary measurement | Luminescence |
| | Key reagents | SH-SY5Y neuroblastoma cell line, luciferin, ATP, lysis reagent (SteadyGlo, Promega) |
| | Assay protocol | See materials and Methods |
| | Additional comments | |
| Library | Library size | 2,000 |
| | Library composition | Biologically active compounds, including diverse set of pure natural products |
| | Source | Microsource Spectrum |
| | Additional comments | |
| Screen | Format | 384-well microtiter plate |
| | Concentration(s) tested | 16 and 32 µM |
| | Plate controls | TBHQ (100% activation), DMSO (0%) |
| | Reagent/compound dispensing system | Matrix-Wellmate for Cells/ Perkin-Elmer Minitrak for compounds |
| | Detection instrument and software | Perkin-Elmer EnVision/Wallac EnVsion Manager version 1.0 |
| | Assay validation/QC | Z' > 0.7 |
| | Correction factors | None |
| | Normalization | % activation = (Smaple counts-DMSO counts/TBHQ counts-DMSO counts) |
| | Additional comments | |
| Post-HTS analysis | Hit criteria | 25% activation |
| | Hit rate | 11%, 93% of these re-confirmed by re-test in duplicate |
| | Additional assay(s) | luciferase immunoblot |
| | Confirmation of hit purity and structure | HPLC-MS tested |
| | Additional comments | |

Extended SAR Analysis

Selected hits were tested in 96-format white, flat-bottom plates with varied concentrations of an inhibitor (0.05-25 µM). Cells were plated at the density of 25,000 cell per well using a WellMate multichannel dispenser from Matrix (Thermo Fisher Scientific) and grown overnight on DMEM/F12+GlutaMAX (100 µl per well). Then the inhibitor was added, and the plates were incubated for a fixed time interval; the medium was removed, cells lysed in 20 µL (out of which 4 µL were taken for protein measurement), then BrightGlo™ reagent (Promega) was added to the wells and luciferase activity measured on a luminometer Lmax11384 (Molecular Devices). The reporter activation was normalized to the background luminescence divided by protein concentration. Kinetics of reporter activation were measured by adding varied fixed concentrations of an inhibitor at different time points followed by simultaneous cell lysis, protein determination, and luciferase activity measurement in the whole 96-well plate; this assay format minimizes experimental error originating from the well-known instability of luciferase reagent.

Computer Modeling

Docking experiments were performed using the CDOCKER algorithm, followed by force field minimization and binding energy calculations using the molecular mechanics algorithm CHARMm (as implemented in Discovery Studio 2.5, Accelrys, San Diego, Calif.). The crystal structure of human Keap1 kelch domain with the bound 16-mer peptide of human Neh2 (2FLU.pdb) with hydrogen atoms added was used as the starting template structure.

Si RNA Keap1 Knockdown

SiRNA against human Keap1 and control non-specific siRNA were purchased from Thermo Scientific Dharmacon. Neroblastoma SH-SYSY cells carried pcDNA3-Neh2LUC10 or pcDNA3-LUC3 were plated at 3×105 cells per well in 6 well plate. Next day cells were transfected with On-Targetplus Smartpool siRNA Keap1 and ON-TARGETplus Non-Targeting Pool using Lipofectomine 2000 (Invitrogen) according protocol. Transfected cells were probed in luciferase assays and quantitative real-time PCR analysis 24, 48, 72 h after transfection with siRNA.

Real-Time Polymerase Chain Reaction

Total RNA was isolated from SH-SY5Y cells by using NucleoSpin RNAII kit (Macherey-Nagel) and used for cDNA synthesis by SuperScript III First-Strand Synthesis System for RT-PCR (Invitrogen). Quantitative real-time PCR analyses of human KEAP1, GCLC, GCLM, HO-1 and NQO1 were performed by using the corresponding primers and probe set from Applied Biosystems on the ABI 7500 Fast Real Time PCR TaqMan system (Applied Biosystems). GAPDH was used for normalization.

MTT assay

Cell death was monitored simultaneously with luciferase assays by plating cells, in parallel, in the transparent bottom plates and performing two independent assays of cell viability along with luciferase: MTT reduction and phase contrast observation. In all cases, MTT agreed with our morphological assay. The range of concentrations used was chosen to minimize the possibility of cell death in the time interval and concentration range shown. The use of robotics for cell plating results in uniform concentration of cells along the plate, and we have found after validation no need to continue normalization to the cell protein. Additional manipulations in the same well result in increasing the errors in following activity measurements as we established during the HTS optimization.

Redox active glutathione measurements. (PINTO et al., *J Chromatogr B Analyt Technol Biomed Life Sci.*, 877(28): 3434-3441 (2009))

Concentrations of the redox-active glutathione were measured without prior derivatization by high performance liquid chromatography (HPLC) coupled with a coulometric detector. The HPLC system consisted of an ESA Liquid Chromatograph equipped with an 8-channel coulometric array (CoulArray) detector (ESA, Inc., Chelmsford, Mass.). Following rinsing of cell media from cultured cells with PBS, astrocytes were harvested from culture plates by scraping and collected into Eppendoff tubes. Cells were spun at 900×g for 5 minutes, the PBS rinse removed and cell pellets frozen in dry ice. Prior to HPLC analysis, cells were lyzed by addition of 50 µL of ice-cold, de-ionized water followed by addition of 12.5 µL of 25% (w/v) metaphosphoric acid (MPA) with vortexing. Samples were held in an ice bath for 15 minutes and then centrifuged at 50 C. for 10 minutes at 13,000 g in a microfuge to sediment coagulated protein. Protein precipitates were dissolved in 70 µL of 0.1 N NaOH and protein was quantitated by a spectrophotometric method using bicinchoninic acid (BCA) reagent (Pierce Chemical Co., Rockford, Ill.). In many cases, supernatant fractions were analyzed immediately after removal of denatured protein for GSH determination using HPLC separation (see below). The supernatant fractions from 5% MPA homogenates were injected directly onto a Bio-Sil ODS-5S, 5-µm particle size, 4.0×250 mm, C18 column (Bio-Rad, Life Science Research Group, Hercules, Calif.) and eluted with a mobile phase consisting of 50 mM $NaH_2PO_4$, 0.05 mM octane sulfonic acid, and 3% (v/v) acetonitrile (pH 2.62) at a flow rate of 1 ml/min. PEEKTM (polyetheretherketone) tubing was used throughout the HPLC system, and 0.2µ PEEKTM filters were placed pre- and post-column to protect both column and flow cells, respectively, from any potential particulate matter. A Rheodyne injection valve with a 5-µl sample loop was used to manually introduce samples. The 8-channel CoulArray detectors were set at 175, 250, 325, 400, 475, 550, 650, and 750 mV, respectively. Peak areas were analyzed using ESA, Inc. software. Concentration of glutathione was obtained from appropriate standard curves, and was normalized as nmol/mg protein.

Western Blotting

Cell cultures were rinsed in PBS then lysed and scraped in RIPA buffer (Boston BioProducts) with 1% Protease Inhibitor Cocktail (Sigma). Lysates were vortexed, incubated on ice for 15 min, sonicated, and stored at −80° C. Protein concentration was determined using BCA Protein Assay Kit (Pierce/Thermo Scientific, Rockford, Ill.). Samples were diluted in water to equalize protein concentration, mixed with Laemmli SDS sample buffer (reducing, 4×), boiled at 100° C. for 5 min, cooled on ice, and centrifuged at 13,000 g for 1 minute immediately before gel loading. Samples were resolved by SDS-PAGE using 10% gels run at 120V for 2 h and transferred onto nitrocellulose membranes at 100V for 1 h. Quantitative Western blots were performed according to the Western Blot Analysis protocol supplied by L1-COR Biosciences (Doc#988-09288). Primary antibodies used were mouse monoclonal antibody for luciferase sc-74548 diluted 1:1000 (Santa Cruz), rabbit polyclonal antibody for beta-actin A2066 diluted 1:10,000 (Sigma), and a rabbit polyclonal antibody for heme oxygenase-1 (Stressgen, 1:1,000). Secondary antibodies used were goat anti-Rabbit IR dye 680 and goat anti-mouse IRDye 800CW (L1-COR Biosciences).

Western Blot for Nrf2.

Whole cell lysates of astrocytes overexpressing Nrf2 (50 µg) were loaded in a precast NuPAGE gel with 4-12% gradient (Invitrogen), run and transferred to nitrocellulose membrane with 100V for 1 hour at 4° C. The membrane was incubated with L1-COR Odissey blocking buffer, L1-COR Biosciences, overnight at 4° C. and for 2 hours at room temperature with the Nrf2 antibody (Abcam, dilution 1:500) and beta-actin antibody (Sigma, dilution 1:5000). The membranes were developed with the L1-COR system (L1-COR Biosciences).

Keap1 Labeling by sulfoxythiocarbate-alkyne (STCA) in Cells

Keap1 labeling experiments were performed as described previously (AHN et al., *Proc. Natl. Acad. Soc. USA.*, 107: 9590-9595 (2010)) with following modifications. HEK293 cells transiently expressing FLAG-Keap1 were incubated with 200 µM competing compounds (sulforaphane, fisetin, quercetin, gedunin, TBHQ, ciclopirox, geldanamycin) in serum-free DMEM for 1 h. After washing with PBS, cells were further incubated with 10 µM sulfoxythiocarbate-alkyne (STCA) for 30 min at 37° C. FLAG-Keap1 was immunoprecipitated from cell lysates, subjected to click reaction with biotin azide on beads, and eluted with SDS-loading buffer. Eluted samples were immunoblotted with Streptavidin-HRP (Pierce) and anti-FLAG antibodies (Sigma).

Adenoviral Transduction

Adenoviral vectors containing cDNA for Nrf2 or Keap1 were obtained from the laboratory of Timothy H. Murphy. Nrf2 was driven by a CMV promoter and a separate CMV promoter also drove the expression of GFP. Keap1 was driven by a CMV promoter and contained a FLAG tag. Cells were treated with the adenoviral plasmids at a multiplicity of infection (MOI)=25 for 4 hr in serum free Opti-MEM media and used ~24-48 hr following transduction.

Neuronal Viability

Neuronal viability was quantified using a modified protocol (Carrier et al. 2006). Astrocyte-neuron cocultures were 4% paraformaldehyde fixed for 0.5 h at 37° C., then incubated with anitibodies against the neuronal specific marker microtubule associated protein 2 (polyclonal anti-MAP2, 1:500, in 4% normal goat serum and 0.3% triton-x 100) overnight at 4° C. Then the cells were incubated with rabbit secondary antibodies conjugated with horseradish peroxidase (anti-rabbit-HRP, 1:1250, in 4% normal goat serum and 0.3% triton-x 100) for 0.5 h at RT. The fixed cells were incubated with a reaction buffer containing 150 μM Amplex Red and 800 μM $H_2O_2$ made up in basal media (135 mM NaCl, 3.8 mM KCl, 1.2 mM $MgSO_4$, 1.3 $CaCl2$, 1.2 mM $KH_2PO_4$, 10 mM D-glucose, 10 mM HEPES, pH=7.4) for approximately 0.5 h at RT; the formation of resorufin was measured on a Spectramax Plus 384 (Molecular Devices) at 560 nm at RT. To account for the non-specific binding of MAP2 to astrocytes, values determined for astrocytes alone were subtracted from coculture values.

TABLE 1A

Compounds with previously unknown NRF2 activation activity. See Table 1B for further identifying information.

| | | TBHQ > 25% Activation | | | |
|---|---|---|---|---|---|
| Compound name | Compound ID | 100 nL | 200 nL | Activation 100 nL | Activation 200 nL |
| TRIAMTERENE | hts_ru033777 | 3914 | 872 | 405 | 23 |
| AMSACRINEHYDROCHLORIDE | hts_ru033647 | 3384 | 1264 | 345 | 40 |
| FENBENDAZOLE | hts_ru032282 | 4908 | 92 | 224 | −24 |
| ZOXAZOLAMINE | hts_ru032617 | 4336 | 4092 | 198 | 205 |
| ALBENDAZOLE | hts_ru032696 | 4200 | 5292 | 191 | 272 |
| 4′-DEMETHYLEPIPODOPHYLLOTOXIN | hts_ru032912 | 3188 | 2844 | 185 | 165 |
| SENNOSIDEA | hts_ru032514 | 3204 | 4 | 141 | −24 |
| SOLIDAGENONE | hts_ru033209 | 1976 | 2220 | 121 | 77 |
| SULINDAC | hts_ru032207 | 2692 | 2710 | 114 | 188 |
| CEPHARANTHINE | hts_ru032635 | 2348 | 584 | 98 | 9 |
| PRAZOSINHYDROCHLORIDE | hts_ru032670 | 2132 | 1140 | 87 | 40 |
| TETRANDRINE | hts_ru032938 | 1660 | 596 | 85 | 18 |
| MEBENDAZOLE | hts_ru032283 | 1872 | 3056 | 74 | 216 |
| MAACKIAIN | hts_ru033103 | 1492 | 1772 | 74 | 95 |
| KETOCONAZOLE | hts_ru032061 | 1144 | 1026 | 64 | 33 |
| beta-PELTATIN | hts_ru033717 | 910 | 836 | 62 | 21 |
| ADENOSINE | hts_ru031917 | 1100 | 760 | 61 | 20 |
| ACETYLSEROTONIN | hts_ru033768 | 900 | 1056 | 61 | 31 |
| CHLOROACETOXYQUINOLINE | hts_ru032845 | 1266 | 892 | 60 | 37 |
| THIOSTREPTON | hts_ru033784 | 876 | 1504 | 58 | 50 |
| RHODOMYRTOXINB | hts_ru033305 | 1120 | 1276 | 56 | 36 |
| RHETSININE | hts_ru033347 | 1076 | 532 | 53 | 4 |
| AZATHIOPRINE | hts_ru031900 | 948 | 1804 | 49 | 70 |
| 5beta-12-METHOXY-4,4-BISNOR-8,11,13-PODOCARPATRIEN-3-ONE | hts_ru033469 | 768 | 636 | 46 | 13 |
| NYLIDRINHYDROCHLORIDE | hts_ru032167 | 864 | 800 | 42 | 22 |
| CLOMIPRAMINEHYDROCHLORIDE | hts_ru033468 | 708 | 328 | 39 | 0 |
| OXIBENDAZOLE | hts_ru032769 | 1164 | 1064 | 38 | 36 |
| DEOXYADENOSINE | hts_ru033302 | 788 | 390 | 32 | −3 |
| NADIDE | hts_ru033781 | 640 | 712 | 31 | 16 |
| 3-BROMO-7-NITROINDAZOLE | hts_ru033731 | 632 | 512 | 30 | 8 |
| NOCODAZOLE | hts_ru032446 | 940 | 980 | 28 | 48 |
| ADENOSINEPHOSPHATE | hts_ru032235 | 924 | 556 | 27 | 14 |
| 6-AMINONICOTINAMIDE | hts_ru032971 | 756 | 344 | 26 | 1 |
| PANTOPRAZOLE | hts_ru032718 | 904 | 1504 | 25 | 60 |

TABLE 1B

Further identifying information on previously unknown hits for which data is provided in Table 1A

| Compound name | Compound ID | MW | Formula | Structure |
|---|---|---|---|---|
| TRIAMTERENE | hts_ru033777 | 253.2626 | C12H11N7 | 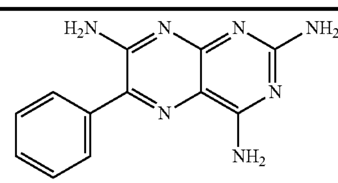 |

TABLE 1B-continued

Further identifying information on previously unknown hits for which data is provided in Table 1A

| Compound name | Compound ID | MW | Formula | Structure |
| --- | --- | --- | --- | --- |
| AMSACRINEHYDROCHLORIDE | hts_ru033647 | 428.9317 | $C_{22}H_{21}ClN_2O_3S$ | 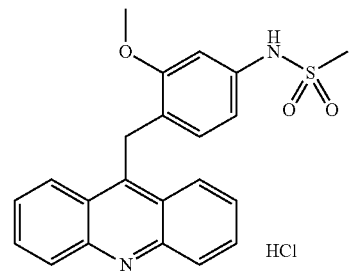 [SMILES: COc1cc(NS(C)(=O)=O)ccc1Cc1c2ccccc2nc2ccccc12 ; Cl] |
| FENBFNDAZOLE | hts_ru032282 | 299.3476 | $C_{15}H_{13}N_3O_2S$ | 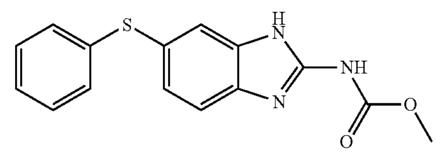 [SMILES: COC(=O)Nc1nc2ccc(Sc3ccccc3)cc2[nH]1] |
| ZOXAZOLAMINE | hts_ru032617 | 168.5804 | $C_7H_5ClN_2O$ | 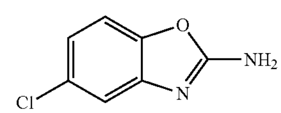 [SMILES: Nc1nc2cc(Cl)ccc2o1] |
| ALBENDAZOLE | hts_ru032696 | 265.3314 | $C_{12}H_{15}N_3O_2S$ | 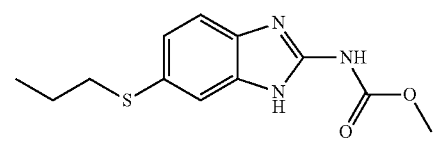 [SMILES: CCCSc1ccc2nc(NC(=O)OC)[nH]c2c1] |
| 4'-DEMETHYLEPIPODO-PHYLLOTOXIN | hts_ru032912 | 400.3787 | $C_{21}H_{20}O_8$ | 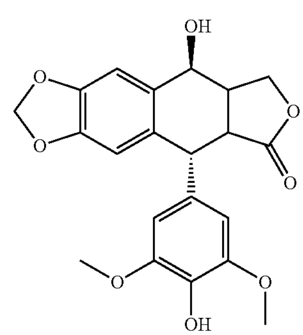 [SMILES: COc1cc([C@@H]2c3cc4c(cc3[C@@H](O)C3COC(=O)C32)OCO4)cc(OC)c1O] |

TABLE 1B-continued

Further identifying information on previously unknown hits for which data is provided in Table 1A

| Compound name | Compound ID | MW | Formula | Structure |
|---|---|---|---|---|
| SENNOSIDEA | hts_ru032514 | 862.7391 | $C_{42}H_{38}O_{20}$ | 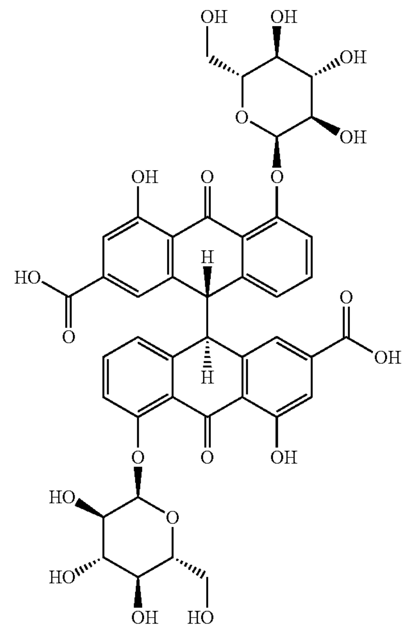 |
| SOLIDAGENONE | hts_ru033209 | 316.4345 | $C_{20}H_{28}O_3$ | 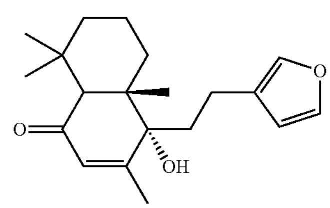 [SMILES: CC1=CC(=O)C2C(C)(C)CCC[C@]2(C)[C@@]1(O)CCc1ccoc1] |
| SULINDAC | hts_ru032207 | 356.4106 | $C_{20}H_{17}FO_3S$ | 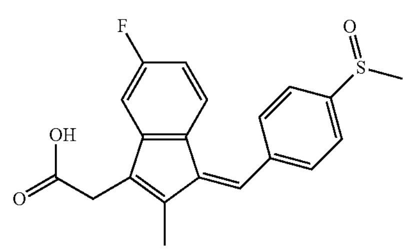 [SMILES: CC1=C(CC(=O)O)c2cc(F)ccc2/C1=C\c1ccc(S(C)=O)cc1] |
| CEPHARANTHINE | hts_ru032635 | 606.7074 | $C_{37}H_{38}N_2O_6$ | 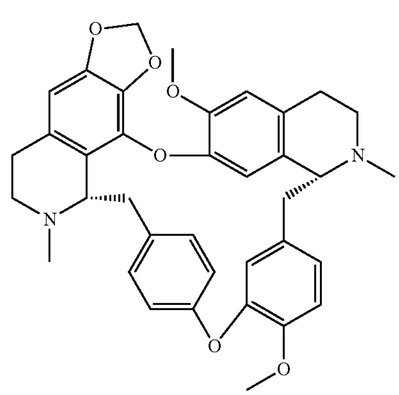 [SMILES: COc1ccc2cc1Oc1ccc(cc1)C[C@H]1c3c(cc4c(c3Oc3cc5c(cc3OC)CCN(C)[C@@H]5C2)OCO4)CCN1C] |

TABLE 1B-continued
Further identifying information on previously unknown hits for which data is provided in Table 1A
| Compound name | Compound ID | MW | Formula | Structure |
|---|---|---|---|---|
| PRAZOSINHYDROCHLORIDE | hts_ru032670 | 419.8621 | $C_{19}H_{22}ClN_5O_4$ | 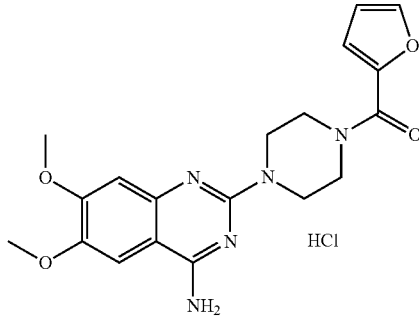 [SMILES: COc1cc2nc(N3CCN(C(=O)c4ccco4)CC3)nc(N)c2cc1OC ; Cl] |
| TETRANDRINE | hts_ru032938 | 622.7499 | $C_{38}H_{42}N_2O_6$ | 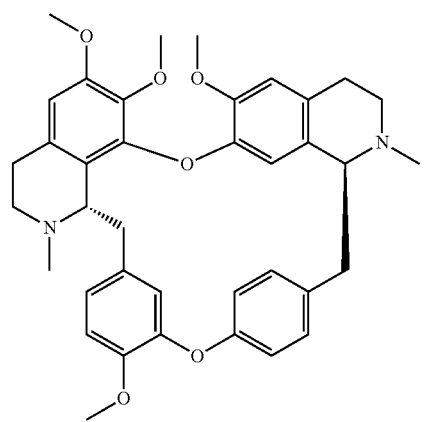 [SMILES: COc1ccc2cc1Oc1ccc(cc1)C[C@H]1c3cc(c(OC)cc3CCN1C)Oc1c(OC)c(OC)cc3c1[C@H](C2)N(C)CC3] |
| MEBENDAZOLE | hts_ru032283 | 295.2927 | $C_{16}H_{13}N_3O_3$ | 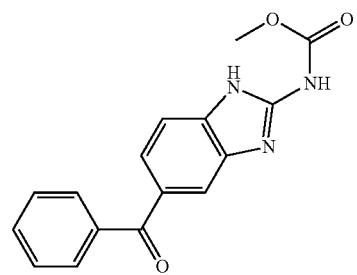 [SMILES: COC(=O)Nc1nc2cc(C(=O)c3ccccc3)ccc2[nH]1] |
| MAACKIAIN | hts_ru033103 | 284.2635 | $C_{16}H_{12}O_5$ | 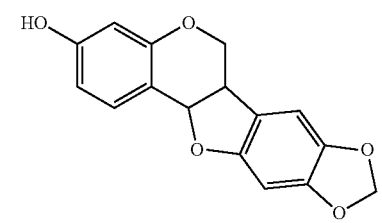 [SMILES: Oc1ccc2c(c1)OCC1c3cc4c(cc3OC21)OCO4] |
| KETOCONAZOLE | hts_ru032061 | 531.4309 | $C_{26}H_{28}Cl_2N_4O_4$ | 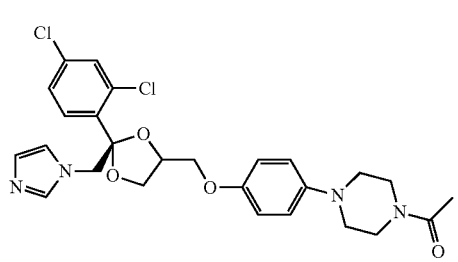 [SMILES: CC(=O)N1CCN(c2ccc(OCC3CO[C@](Cn4ccnc4)(c4ccc(Cl)cc4Cl)O3)cc2)CC1] |

TABLE 1B-continued

Further identifying information on previously unknown hits for which data is provided in Table 1A

| Compound name | Compound ID | MW | Formula | Structure |
|---|---|---|---|---|
| beta-PELTATIN | hts_ru033717 | 414.4053 | $C_{22}H_{22}O_8$ | 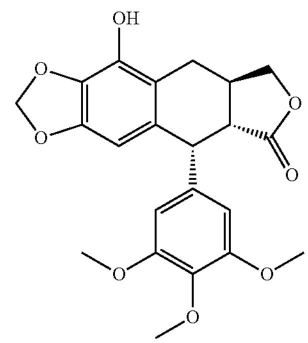 [SMILES: COc1cc([C@@H]2c3cc4c(c(O)c3C[C@H]3COC(=O)[C@@H]32)OCO4)cc(OC)c1OC] |
| ADENOSINE | hts_ru031917 | 267.2413 | $C_{10}H_{13}N_5O_4$ | 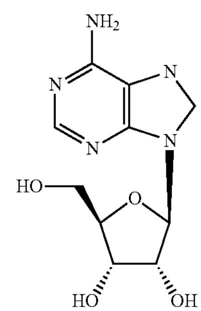 [SMILES: Nc1ncnc2c1NCN2[C@@H]1O[C@H](CO)[C@@H](O)[C@H]1O] |
| ACETYLSEROTONIN | hts_ru033768 | 218.2518 | $C_{12}H_{14}N_2O_2$ | 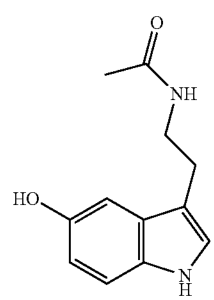 [SMILES: CC(=O)NCCc1c[nH]c2ccc(O)cc12] |
| CHLOROACETOXYQUINOLINE | hts_ru032845 | 221.6397 | $C_{11}H_8ClNO_2$ | 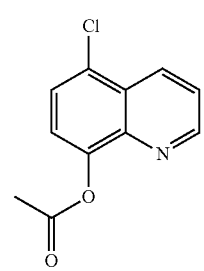 |

TABLE 1B-continued

Further identifying information on previously unknown hits for which data is provided in Table 1A

| Compound name | Compound ID | MW | Formula | Structure |
|---|---|---|---|---|
| THIOSTREPTON | hts_ru033784 | 1664.8868 | $C_{72}H_{85}N_{19}O_{18}S_5$ | 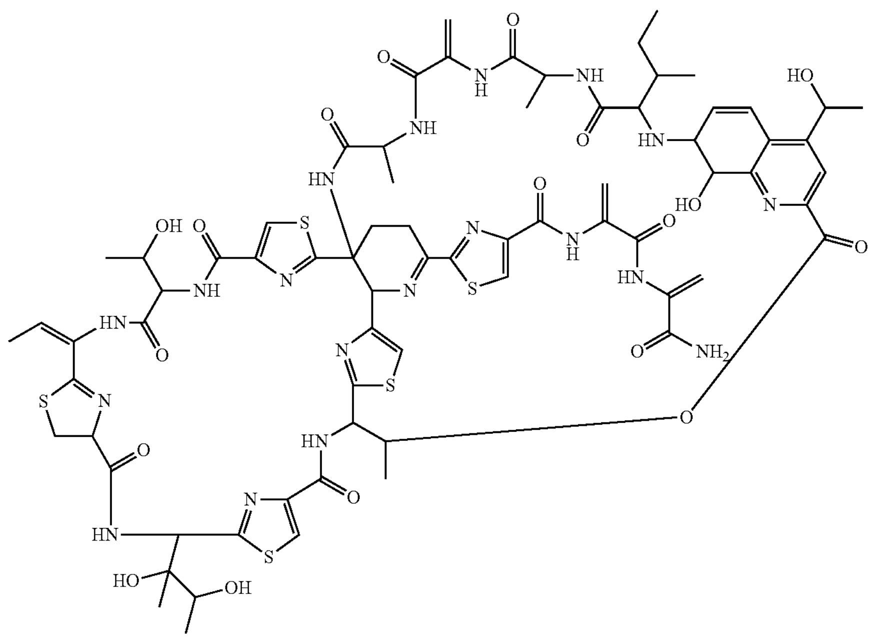 [SMILES: C=C(NC(=O)C(=C)NC(=O)c1csc(C2=NC3c4csc(n4)C4NC(=O)c5csc(n5)C(C(C)(O)C(C)O)NC(=O)C5CSC(=N5)/C(=C\C)NC(=O)C(C(C)O)NC(=O)c5csc(n5)C3(CC2)NC(=O)C(C)NC(=O)C(=C)NC(=O)C(C)NC(=O)C(C(C)CC)NC2C=Cc3c(C(C)O)cc(nc3C2O)C(=O)OC4C)n1)C(N)=O] |
| RHODOMYRTOXINB | hts_ru033305 | 428.4749 | C24H28O7 | 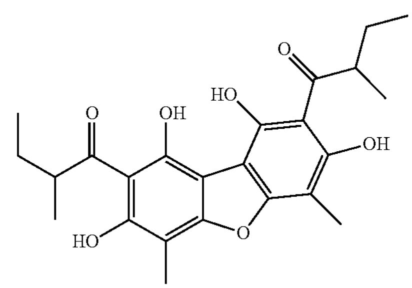 [SMILES: CCC(C)C(=O)c1c(O)c(C)c2oc3c(C)c(O)c(C(=O)C(C)CC)c(O)c3c2c1O] |
| RHETSININE | hts_ru033347 | 319.3572 | C19H17N3O2 | 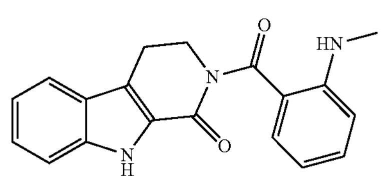 [SMILES: CNc1ccccc1C(=O)N1CCc2c([nH]c3ccccc23)C1=O] |
| AZATHIOPRINE | hts_ru031900 | 277.2626 | C9H7N7O2S | 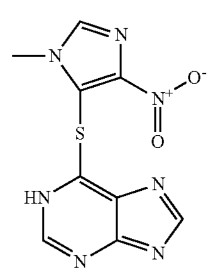 [SMILES: Cn1cnc([N+](=O)[O-])c1Sc1[nH]cnc2ncnc1-2] |

TABLE 1B-continued

Further identifying information on previously unknown hits for which data is provided in Table 1A

| Compound name | Compound ID | MW | Formula | Structure |
| --- | --- | --- | --- | --- |
| 5beta-12-METHOXY-4,4-BISNOR-8,11,13-PODOCARPATRIEN-3-ONE | hts_ru033469 | 244.3288 | $C_{16}H_{20}O_2$ | 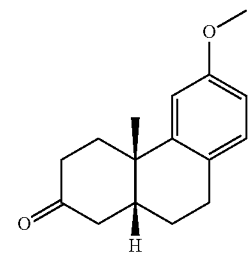 [SMILES: COc1ccc2c(c1)[C@@]1(C)CCC(=O)C[C@H]1CC2] |
| NYLIDRIN-HYDROCHLORIDE | hts_ru032167 | 335.8682 | $C_{19}H_{26}ClNO_2$ | 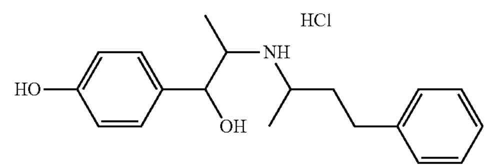 [SMILES: CC(CCc1ccccc1)NC(C)C(O)c1ccc(O)cc1 ; Cl] |
| CLOMIPRAMINE-HYDROCHLORIDE | hts_ru033468 | 351.3133 | $C_{19}H_{24}Cl_2N_2$ | 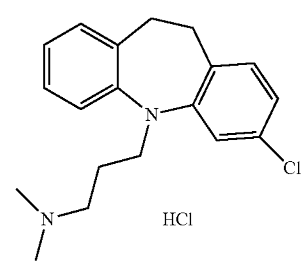 [SMILES: CN(C)CCCN1c2ccccc2CCc2ccc(Cl)cc21 ; Cl] |
| OXIBENDAZOLE | hts_ru032769 | 249.2658 | $C_{12}H_{15}N_3O_3$ | 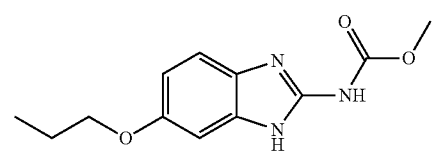 [SMILES: CCCOc1ccc2nc(NC(=O)OC)[nH]c2c1] |
| DEOXYADENOSINE | hts_ru033302 | 251.2419 | $C_{10}H_{13}N_5O_3$ | 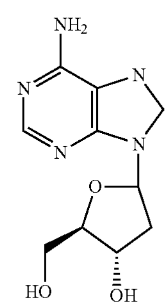 [SMILES: Nc1ncnc2c1NCN2C1C[C@H](O)[C@@H](CO)O1] |

TABLE 1B-continued
Further identifying information on previously unknown hits for which data is provided in Table 1A
| Compound name | Compound ID | MW | Formula | Structure |
| --- | --- | --- | --- | --- |
| NADIDE | hts_ru033781 | 663.4251 | $C_{21}H_{27}N_7O_{14}P_2$ | 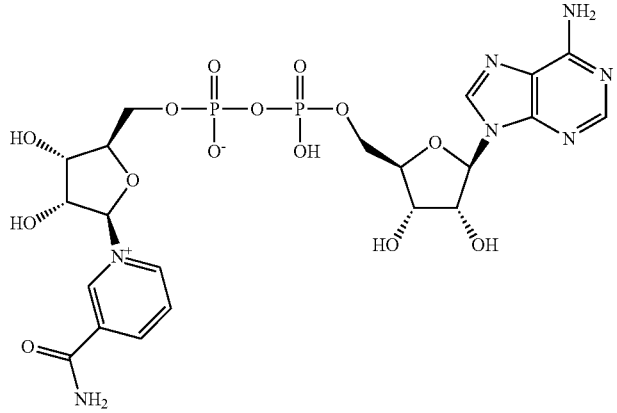 [SMILES: NC(=O)c1ccc[n+]([C@@H]2O[C@H](COP(=O)([O-])OP(=O)(O)OC[C@H]3O[C@@H](n4cnc5c(N)ncnc54)[C@H](O)[C@@H]3O)[C@@H](O)[C@H]2O)c1] |
| 3-BROMO-7-NITROINDAZOLE | hts_ru033731 | 242.0296 | $C_7H_4BrN_3O_2$ | 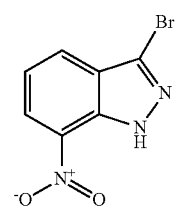 |
| NOCODAZOLE | hts_ru032446 | 301.3204 | $C_{14}H_{11}N_3O_3S$ | 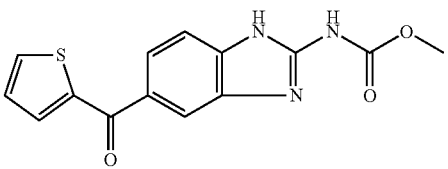 [SMILES: COC(=O)Nc1nc2cc(C(=O)c3cccs3)ccc2[nH]1] |
| ADENOSINE PHOSPHATE | hts_ru032235 | 347.2212 | $C_{10}H_{14}N_5O_7P$ | 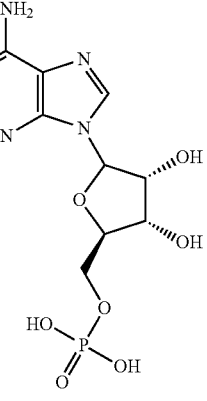 |
| 6-AMINONICOTINAMIDE | hts_ru032971 | 137.1393 | $C_6H_7N_3O$ | 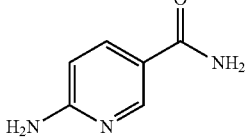 |

TABLE 1B-continued

Further identifying information on previously unknown hits for which data is provided in Table 1A

| Compound name | Compound ID | MW | Formula | Structure |
|---|---|---|---|---|
| PANTOPRAZOLE | hts_ru032718 | 383.3698 | $C_{16}H_{15}F_2N_3O_4S$ | 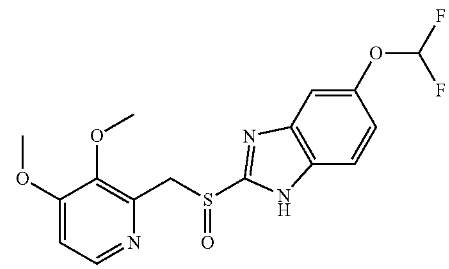 [SMILES: COc1ccnc(CS(=O)c2nc3cc(OC(F)F)ccc3[nH]2)c1OC] |

TABLE 2

Hits in NRF-luc screen that were already known Nrf2 activators.

| | | | | TBHQ > 25% Activation | |
|---|---|---|---|---|---|
| Compound name | Compound ID | 100 nL | 200 nL | Activation 100 nL | Activation 200 nL |
| 2',4-DIHYDROXY-3,4',6'-TRIMETHOXYCHALCONE | hts_ru033766 | 6104 | 7512 | 655 | 305 |
| METHYL7-DESOXYPURPUROGALLIN-7-CARBOXYLATETRIMETHYLETHER | hts_ru033104 | 8248 | 1932 | 516 | 105 |
| METHYL7-DESHYDROXYPYROGALLIN-4-CARBOXYLATE | hts_ru033640 | 4444 | 3792 | 466 | 147 |
| TOXAPHENE | hts_ru033403 | 5648 | 5632 | 395 | 226 |
| 2',4-DIHYDROXYCHALCONE | hts_ru033716 | 3784 | 120 | 390 | −9 |
| STROBANE | hts_ru033443 | 5556 | 5836 | 388 | 235 |
| TETRAHYDROGAMBOGICACID | hts_ru033167 | 5480 | 2748 | 383 | 100 |
| SAPPANONEADIMETHYLETHER | hts_ru033101 | 6124 | 2008 | 377 | 110 |
| CARNOSICACID | hts_ru033740 | 3620 | 4604 | 372 | 182 |
| TANSHINONEIIA | hts_ru033329 | 5092 | 2452 | 354 | 87 |
| BISSALICYLFUMARATE | hts_ru033658 | 3328 | 3992 | 338 | 156 |
| MINOCYCLINEHYDROCHLORIDE | hts_ru033744 | 3224 | 4304 | 326 | 169 |
| 2',5'-DIHYDROXY-4-METHOXYCHALCONE | hts_ru033785 | 3188 | 800 | 322 | 20 |
| 2',4-DIHYDROXY-3,4-DIMETHOXYCHALCONE | hts_ru033850 | 5876 | 3964 | 321 | 185 |
| 2',3-DIHYDROXY-4,4',6'-TRIMETHOXYCHALCONE | hts_ru033809 | 5436 | 544 | 296 | 10 |
| 3H-1,2-DITHIOLE-3-THIONE | hts_ru033864 | 5416 | 2832 | 295 | 127 |
| SAPPANONEA7-METHYLETHER | hts_ru033099 | 4822 | 2904 | 292 | 169 |
| ISOLIQUIRITIGENIN | hts_ru032948 | 4452 | 2364 | 268 | 134 |
| SERICETIN | hts_ru033544 | 2672 | 800 | 263 | 20 |
| ALACHLOR | hts_ru033420 | 3852 | 4892 | 261 | 194 |
| EXEMESTANE | hts_ru033805 | 4836 | 4668 | 261 | 220 |
| CURCUMIN | hts_ru032967 | 4208 | 264 | 252 | −4 |
| SAPPANONEATRIMETHYLETHER | hts_ru033376 | 3652 | 2586 | 246 | 93 |
| 2',4'-DIHYDROXY-4-METHOXYCHALCONE | hts_ru033789 | 4576 | 2720 | 246 | 121 |
| PHENETHYLCAFFEATE(CAPE) | hts_ru033561 | 2508 | 16 | 245 | −14 |
| 2,3-DIMERCAPTOSUCCINICACID | hts_ru033862 | 4452 | 2760 | 238 | 123 |
| EPOXY(4,5alpha)-4,5-DIHYDROSANTONIN | hts_ru033115 | 3828 | 3164 | 227 | 186 |
| 2',4'-DIHYDROXYCHALCONE | hts_ru033786 | 2352 | 1388 | 227 | 45 |
| FISETIN | hts_ru033233 | 3360 | 1320 | 224 | 38 |
| KOPARIN | hts_ru033098 | 3768 | 492 | 223 | 11 |
| GEDUNIN | hts_ru032820 | 4812 | 3708 | 222 | 184 |
| DEOXYSAPPANONEB7,3'-DIMETHYLETHERACETATE | hts_ru033102 | 3740 | 1388 | 221 | 70 |
| CITRININ | hts_ru032775 | 4752 | 4300 | 219 | 217 |
| 4'-HYDROXYCHALCONE | hts_ru033088 | 3674 | 1488 | 217 | 76 |
| CARBIDOPA | hts_ru033639 | 2262 | 1900 | 217 | 67 |
| beta-DIHYDROGEDUNOL | hts_ru033685 | 2270 | 3252 | 217 | 124 |
| 3-ACETOXYPREGN-16-EN-12,20-DIONE | hts_ru033482 | 2236 | 1040 | 214 | 30 |
| DEACETOXY-7-OXISOGEDUNIN | hts_ru033040 | 2960 | 3040 | 170 | 178 |
| 7-DEACETOXY-7-OXOKHIVORIN | hts_ru032934 | 2924 | 2284 | 168 | 128 |
| HIERACIN | hts_ru033285 | 2502 | 1832 | 160 | 60 |
| TENIPOSIDE | hts_ru032544 | 3572 | 1520 | 159 | 61 |
| DIHYDROTANSHINONEI | hts_ru033339 | 2480 | 572 | 158 | 5 |
| 4'-HYDROXYFLAVANONE | hts_ru033585 | 1752 | 2088 | 158 | 75 |
| TIOXOLONE | hts_ru032439 | 3542 | 768 | 156 | 31 |
| PURPUROGALLIN | hts_ru032795 | 3508 | 2420 | 156 | 112 |
| ISOGEDUNIN | hts_ru033047 | 2724 | 3188 | 155 | 188 |
| CHLORHEXIDINE | hts_ru031904 | 2188 | 1750 | 147 | 67 |
| FLAVOKAWAINB | hts_ru033083 | 2564 | 8 | 144 | −21 |
| ETHACRYNICACID | hts_ru032014 | 2088 | 3604 | 139 | 156 |
| RHAMNETIN | hts_ru033287 | 2216 | 1536 | 138 | 47 |

TABLE 2-continued

Hits in NRF-luc screen that were already known Nrf2 activators.

| | | | | TBHQ > 25% Activation | |
|---|---|---|---|---|---|
| Compound name | Compound ID | 100 nL | 200 nL | Activation 100 nL | Activation 200 nL |
| EUPHOL | hts_ru033540 | 1572 | 2064 | 138 | 74 |
| 4'-METHOXYCHALCONE | hts_ru033086 | 2400 | 102 | 134 | −15 |
| VIOLASTYRENE | hts_ru033081 | 2388 | 1096 | 133 | 50 |
| NORETHYNODREL | hts_ru032107 | 1948 | 3920 | 128 | 171 |
| 4-AMINOETHYLBENZENESULFONYLFLUORIDEHYDROCHLORIDE | hts_ru032932 | 2288 | 124 | 126 | −13 |
| CONIFERYLALCOHOL | hts_ru033335 | 2032 | 2264 | 125 | 79 |
| 4-METHYLDAPHNETIN | hts_ru033698 | 1428 | 2102 | 121 | 75 |
| 2,3-DIHYDROXY-4-METHOXY-4'-ETHOXYBENZOPHENONE | hts_ru033108 | 2142 | 1324 | 117 | 65 |
| OXYPHENBUTAZONE | hts_ru032148 | 1760 | 3084 | 113 | 131 |
| BIXIN | hts_ru033345 | 1880 | 3036 | 113 | 113 |
| 2',beta-DIHYDROXYCHALCONE | hts_ru033137 | 2064 | 44 | 112 | −18 |
| DIHYDROGEDUNIN | hts_ru033371 | 1866 | 3068 | 112 | 114 |
| OXIDOPAMINEHYDROCHLORIDE | hts_ru032128 | 1676 | 2936 | 107 | 124 |
| CHLORDANE | hts_ru033413 | 1796 | 3540 | 107 | 135 |
| GENISTEIN | hts_ru033084 | 1980 | 1748 | 106 | 93 |
| ALEXIDINEHYDROCHLORIDE | hts_ru032835 | 1900 | 52 | 101 | −18 |
| DIHYDRO-7-DESACETYLDEOXYGEDUNIN | hts_ru033021 | 1852 | 1796 | 98 | 96 |
| DEOXYANDIROBIN | hts_ru032983 | 1816 | 1944 | 95 | 106 |
| 3-DEACETYLKHIVORIN | hts_ru033445 | 1628 | 2102 | 94 | 72 |
| COLFORSIN | hts_ru032520 | 2208 | 2568 | 91 | 120 |
| KHAYASIN | hts_ru032954 | 1736 | 1928 | 90 | 105 |
| CHLORPYRIFOS | hts_ru033461 | 1572 | 1704 | 90 | 55 |
| EUPHOLACETATE | hts_ru033063 | 1710 | 2020 | 89 | 111 |
| BENDIOCARB | hts_ru033412 | 1532 | 2760 | 87 | 101 |
| DEHYDROVARIABILIN | hts_ru033134 | 1672 | 916 | 86 | 39 |
| ERGOSTEROL | hts_ru033139 | 1676 | 1640 | 86 | 86 |
| 7-DESACETOXY-6,7-DEHYDROGEDUNIN | hts_ru032997 | 1660 | 188 | 85 | −9 |
| 3-HYDROXY-3',4'-DIMETHOXYFLAVONE | hts_ru033368 | 1504 | 316 | 85 | −6 |
| SECURININE | hts_ru032606 | 2068 | 176 | 84 | −14 |
| MECYSTEINEHYDROCHLORIDE | hts_ru032213 | 2028 | 3064 | 82 | 216 |
| ANDROSTA-1,4-DIEN-3,17-DIONE | hts_ru033316 | 1444 | 2048 | 81 | 70 |
| CAFESTOLACETATE | hts_ru033384 | 1452 | 1976 | 81 | 67 |
| PIPOBROMAN | hts_ru032507 | 1976 | 3732 | 79 | 185 |
| ANDROGRAPHOLIDE | hts_ru033223 | 1404 | 708 | 78 | 11 |
| LEVULINICACID,3-BENZYLIDENYL- | hts_ru033574 | 1048 | 1348 | 78 | 43 |
| ERIODYCTOL | hts_ru033756 | 1028 | 768 | 76 | 18 |
| ENDECAPHYLLINX | hts_ru033501 | 1020 | 1268 | 75 | 40 |
| ANTIAROL | hts_ru033688 | 1016 | 2248 | 74 | 81 |
| 2-BENZOYL-5-METHOXYBENZOQUINONE | hts_ru033490 | 994 | 2280 | 72 | 83 |
| SPERMIDINETRIHYDROCHLORIDE | hts_ru033526 | 1000 | 860 | 72 | 22 |
| TRETINON | hts_ru032410 | 1816 | 3192 | 71 | 227 |
| ACETOCHLOR | hts_ru033404 | 1320 | 3024 | 71 | 112 |
| SWIETENOLIDE-3-ACETATE | hts_ru032916 | 1430 | 2088 | 70 | 115 |
| DEACETYLGEDUNIN | hts_ru032963 | 1412 | 220 | 69 | −7 |
| DEOXYSAPPANONEB7,3'-DIMETHYLETHER | hts_ru033109 | 1416 | 1484 | 69 | 76 |
| ABIETICACID | hts_ru033372 | 1256 | 1748 | 67 | 57 |
| PROMETRYN | hts_ru033439 | 1264 | 542 | 67 | 4 |
| DIBENZOYLMETHANE | hts_ru032961 | 1368 | 204 | 66 | −8 |
| DEHYDROABIETAMIDE | hts_ru033559 | 940 | 3506 | 66 | 135 |
| 3,5-DIHYDROXYFLAVONE | hts_ru033800 | 1484 | 24 | 66 | −17 |
| IRIGINOLHEXAACEATATE | hts_ru033105 | 1350 | 1208 | 65 | 58 |
| p-HYDROXYCINNAMALDEHYDE | hts_ru033381 | 1208 | 3256 | 63 | 122 |
| DIHYDROCELASTROL | hts_ru033275 | 1196 | 88 | 62 | −16 |
| 3-DEOXO-3beta-ACETOXYDEOXYDIHYDROGEDUNIN | hts_ru032988 | 1256 | 1252 | 59 | 61 |
| DIMETHOATE | hts_ru033447 | 1148 | 3772 | 59 | 145 |
| AVOCADANOFURAN | hts_ru033474 | 880 | 1088 | 59 | 32 |
| JUGLONE | hts_ru032786 | 1548 | 2116 | 58 | 95 |
| OSTHOL | hts_ru033317 | 1136 | 1634 | 58 | 52 |
| MOMETASONEFUROATE | hts_ru032687 | 1508 | 2936 | 56 | 140 |
| STICTICACID | hts_ru033150 | 1114 | 1952 | 56 | 65 |
| THIOTHIXENE | hts_ru032238 | 1500 | 68 | 55 | −26 |
| 3-alpha-HYDROXYDEOXYGEDININ | hts_ru033027 | 1196 | 1764 | 55 | 94 |
| 3-BROMO-3,4,4-TRIMETHYL-3,4-DIHYDRODIAZETE-1,2-DIOXIDE | hts_ru033846 | 1308 | 1976 | 55 | 83 |
| BETULINICACID | hts_ru032917 | 1176 | 1622 | 54 | 85 |
| PURPURIN | hts_ru032941 | 1176 | 952 | 54 | 41 |
| DECAHYDROGAMBOGICACID | hts_ru033132 | 1184 | 936 | 54 | 40 |
| LAWSONE | hts_ru033475 | 840 | 1140 | 54 | 34 |
| ACETAMINOPHEN | hts_ru031867 | 996 | 1012 | 53 | 32 |
| CEAROIN | hts_ru033189 | 1076 | 2988 | 53 | 111 |
| CEFOTAXIMESODIUM | hts_ru031913 | 968 | 488 | 50 | 7 |

TABLE 2-continued

Hits in NRF-luc screen that were already known Nrf2 activators.

| | | | | TBHQ > 25% Activation | |
|---|---|---|---|---|---|
| Compound name | Compound ID | 100 nL | 200 nL | Activation 100 nL | Activation 200 nL |
| HAEMATOXYLINPENTAACETATE | hts_ru033198 | 1040 | 1304 | 50 | 37 |
| CAFFEICACID | hts_ru033315 | 1040 | 1840 | 50 | 61 |
| COLCHICINE | hts_ru031947 | 944 | 840 | 49 | 24 |
| LAPACHOL | hts_ru032872 | 1076 | 696 | 47 | 24 |
| CADMIUMACETATE | hts_ru033424 | 992 | 312 | 47 | −6 |
| 3-DESMETHYL-5-DESHYDROXYSCLEROIN | hts_ru033493 | 780 | 1212 | 47 | 37 |
| PHORBOLMYRISTATEACETATE | hts_ru033773 | 776 | 712 | 47 | 16 |
| 2,3-DIHYDROXY-6,7-DICHLOROQUINOXALINE | hts_ru032969 | 1056 | 1992 | 46 | 109 |
| SNAP(S-NITROSO-N-ACETYLPENICILLAMINE) | hts_ru032882 | 1044 | 1120 | 45 | 52 |
| DEACETOXY-7-OXOGEDUNIN | hts_ru032924 | 1048 | 448 | 45 | 8 |
| 5,7-DIHYDROXYISOFLAVONE | hts_ru033197 | 964 | 1776 | 45 | 58 |
| NORCANTHARIDIN | hts_ru033577 | 756 | 572 | 45 | 10 |
| APOMORPHINEHYDROCHLORIDE | hts_ru031870 | 880 | 266 | 44 | −3 |
| FURAZOLIDONE | hts_ru031986 | 876 | 1288 | 43 | 45 |
| PREDNISOLONE | hts_ru032131 | 864 | 1452 | 42 | 53 |
| TRICHLORMETHINE | hts_ru033627 | 736 | 2008 | 42 | 71 |
| GRISEOFULVIN | hts_ru032671 | 1208 | 3684 | 41 | 182 |
| ERYTHROMYCINETHYLSUCCINATE | hts_ru032720 | 1220 | 66 | 41 | −20 |
| CENTAUREIN | hts_ru033283 | 916 | 876 | 41 | 19 |
| alpha-DIHYDROGEDUNOL | hts_ru033631 | 720 | 1008 | 41 | 29 |
| ETOPOSIDE | hts_ru032329 | 1180 | 1484 | 40 | 89 |
| DEOXYANDIROBINLACTONE | hts_ru033037 | 964 | 1124 | 40 | 52 |
| PODOPHYLLOTOXINACETATE | hts_ru033377 | 900 | 668 | 40 | 10 |
| DIMETHYL4,4-o-PHENYLENE-BIS(3-THIOPHANATE) | hts_ru033505 | 712 | 836 | 40 | 21 |
| SEMUSTINE | hts_ru032537 | 1172 | 3000 | 39 | 144 |
| FLUMEQUINE | hts_ru032290 | 1156 | 368 | 38 | −2 |
| CARYLOPHYLLENEOXIDE | hts_ru033259 | 874 | 488 | 38 | 2 |
| N-AMINOHEXYL-5-CHLORO-1-NAPTHALENESULFONAMIDEHYDROCHLORIDE | hts_ru033617 | 700 | 372 | 38 | 2 |
| 3beta-ACETOXYDEOXODIHYDROGEDUNIN | hts_ru033051 | 924 | 972 | 37 | 42 |
| 3-HYDROXYTYRAMINE | hts_ru033801 | 990 | 1704 | 37 | 69 |
| CISPLATIN | hts_ru032413 | 1100 | 1496 | 36 | 90 |
| RESERPINE | hts_ru032690 | 1120 | 572 | 36 | 8 |
| CHOLICACID, METHYLESTER | hts_ru033251 | 848 | 804 | 36 | 15 |
| NIFEDIPINE | hts_ru032066 | 776 | 120 | 35 | −10 |
| TRIPTOPHENOLIDE | hts_ru033293 | 832 | 390 | 35 | −3 |
| COLCHICEINE | hts_ru033634 | 672 | 584 | 35 | 11 |
| ISOTRETINON | hts_ru032380 | 1068 | 1456 | 34 | 86 |
| 2',4'-DIHYDROXYCHALCONE4'-GLUCOSIDE | hts_ru032812 | 1056 | 2592 | 33 | 121 |
| EPIGALLOCATECHIN | hts_ru033146 | 864 | 28 | 33 | −20 |
| ISOBUTYLMETHYLXANTHINE | hts_ru033416 | 808 | 640 | 33 | 8 |
| PICROPODOPHYLLOTOXIN | hts_ru032886 | 848 | 1196 | 32 | 57 |
| LUFENURON | hts_ru033718 | 644 | 1022 | 32 | 29 |
| ERYTHROMYCINESTOLATE | hts_ru032397 | 1008 | 1266 | 31 | 71 |
| PERILLYLALCOHOL | hts_ru032921 | 824 | 736 | 31 | 27 |
| ROTENONE | hts_ru033387 | 776 | 1136 | 31 | 30 |
| METHYLORSELLINATE | hts_ru033470 | 640 | 368 | 31 | 1 |
| DEOXYSAPPANONEB7,3'-DIMETHYLETHER | hts_ru033827 | 900 | 622 | 31 | 14 |
| NITROFURANTOIN | hts_ru032076 | 704 | 1316 | 30 | 47 |
| GARCINOLICACID | hts_ru033122 | 800 | 832 | 29 | 33 |
| QUERCETINTETRAMETHYL(5,7,3',4')ETHER | hts_ru033154 | 760 | 644 | 29 | 8 |
| 1(2)alpha-EPDXYDEOXYDIHYDROGEDUNIN | hts_ru033365 | 752 | 1028 | 29 | 25 |
| DANTRON | hts_ru033509 | 616 | 1020 | 29 | 29 |
| HINOKITIOL | hts_ru033839 | 860 | 372 | 29 | 1 |
| MESNA | hts_ru032390 | 952 | 612 | 28 | 18 |
| EPOXYGEDUNIN | hts_ru033017 | 784 | 988 | 28 | 43 |
| alpha-MANGOSTIN | hts_ru033312 | 736 | 16 | 28 | −19 |
| 3-METHOXYCATECHOL | hts_ru033356 | 736 | 116 | 28 | −15 |
| URIDINETRIPHOSPHATETRISODIUM | hts_ru033568 | 612 | 708 | 28 | 16 |
| HETEROPEUCENIN, METHYLETHER | hts_ru033022 | 772 | 1020 | 27 | 45 |
| CLOVANEDIOLDIACETATE | hts_ru033163 | 728 | 1356 | 27 | 40 |
| EPI(13)TORULOSOL | hts_ru033201 | 724 | 448 | 27 | 0 |
| AUROTHIOGLUCOSE | hts_ru033775 | 604 | 360 | 27 | 1 |
| MYCOPHENOLICACID | hts_ru032196 | 904 | 1428 | 26 | 84 |
| TETROQUINONE | hts_ru032486 | 908 | 720 | 26 | 27 |
| 12-HYDROXY-4,4-BISNOR-4,8,11,13-PODOCARPATETRAEN-3-ONE | hts_ru033473 | 592 | 768 | 26 | 18 |
| KUHLMANNIN | hts_ru033670 | 596 | 1104 | 26 | 33 |
| CHLOROCRESOL | hts_ru031914 | 648 | 240 | 25 | −5 |
| CANRENONE | hts_ru032622 | 900 | 832 | 25 | 23 |
| 3-DESHYDROXYSAPPANOLTRIMETHYLETHER | hts_ru033274 | 706 | 784 | 25 | 15 |
| AVOCADYNOFURAN | hts_ru033484 | 582 | 1008 | 25 | 29 |

Additional HTS Hits Identified:
Plate #2
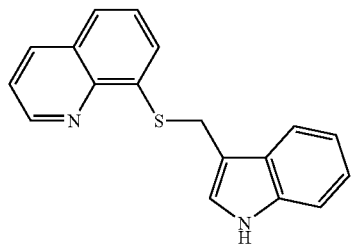
New_ASDI_ID
650,008,080
Nrf2 20-fold
ODD 2 fold
Must be a very good Zn chelator
Plate 1
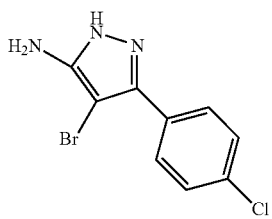
New_ASDI_ID
150,014,605
Nrf 1.7
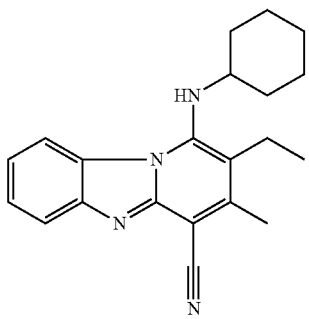
New_ASDI_ID
600,008,016
ODD 1.5 fold
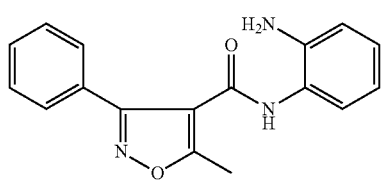
New_ASDI_ID
650,005,014
Nrf 1.7
-continued
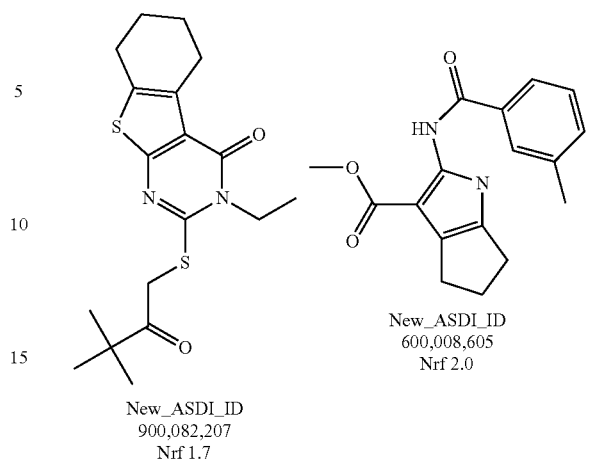
New_ASDI_ID
900,082,207
Nrf 1.7
New_ASDI_ID
600,008,605
Nrf 2.0
Plate 2 Nrf2 2-fold activation
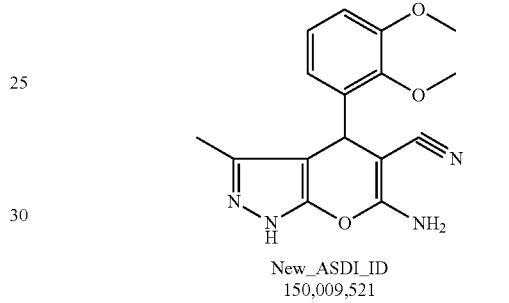
New_ASDI_ID
150,009,521
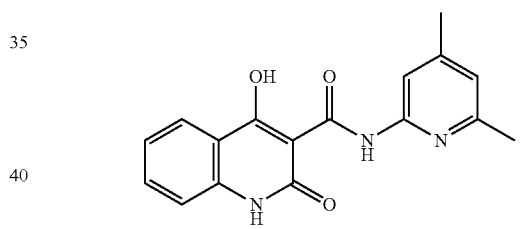
New_ASDI_ID
600,006,918
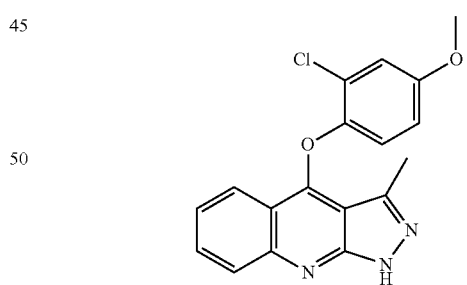
New_ASDI_ID
100,074,285
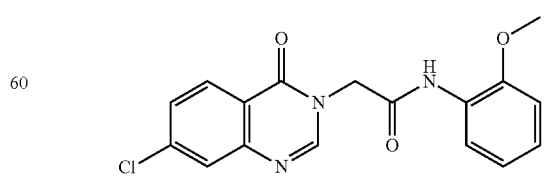
New_ASDI_ID
150,006,829

-continued
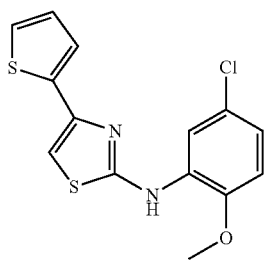
New_ASDI_ID
100,076,910
Plate 2 ODD
1.2 fold
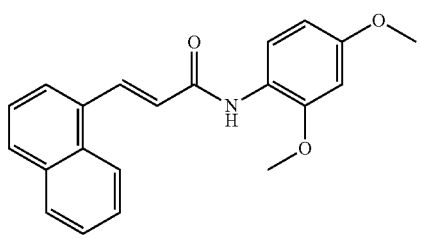
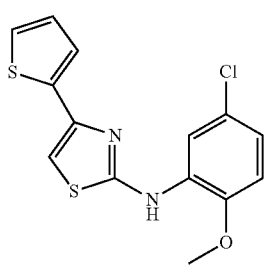
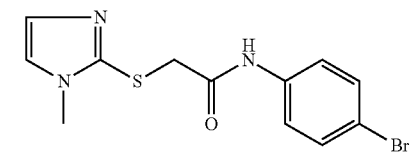
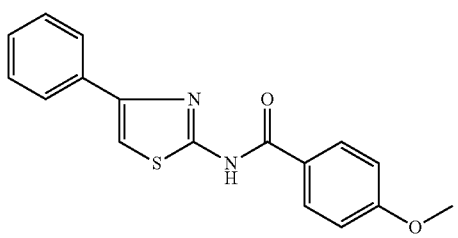
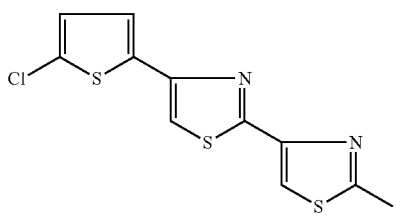
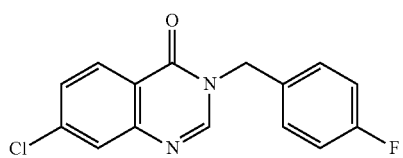
-continued
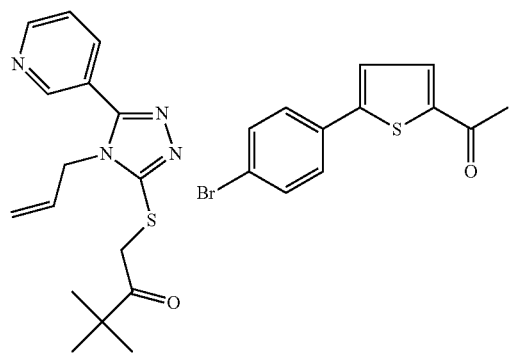
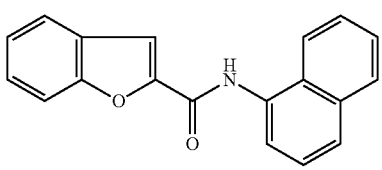
133
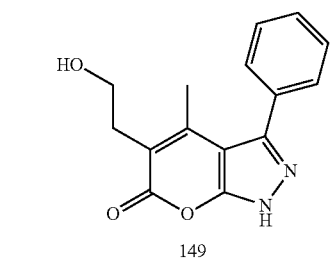
149
Plate 3 ODD
1.5-fold
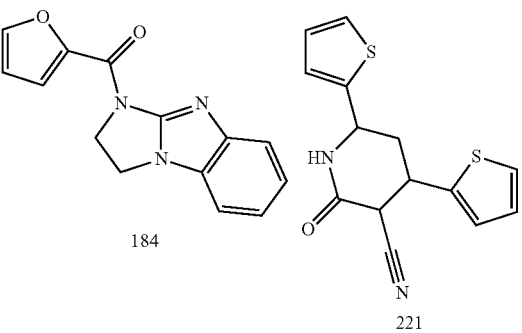
184  221
Plate 3 Nrf ca. 2-fold
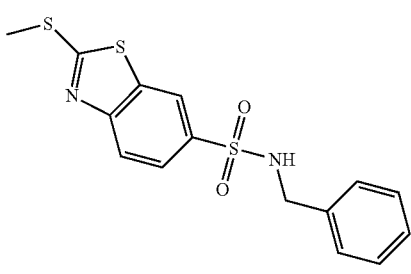
182

-continued

197

221

Plate 4 Nrf ca. 1.5-fold

328

298

314

288

-continued

296

304

Plate 4 ODD 1.2 fold

305

Plate 5 Nrf 429 1.5 fold 357 2-fold 422 3-fold

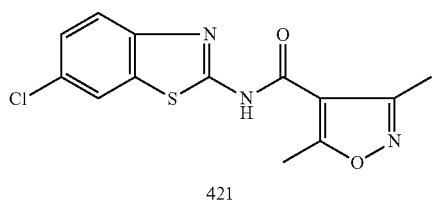
421
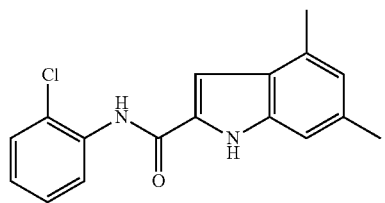
365
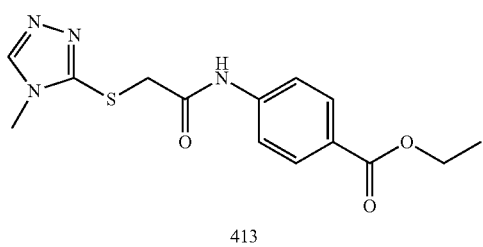
413
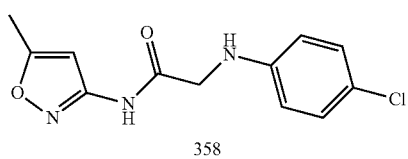
358
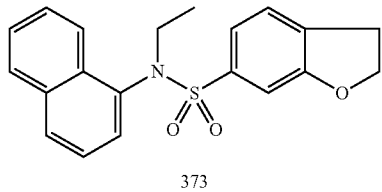
373
Plate 5,6,8 no hits for ODD
Plate 6 no hits for Nrf
Plate 7 Nrf:
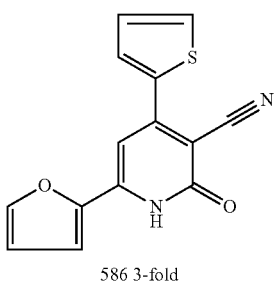
586 3-fold
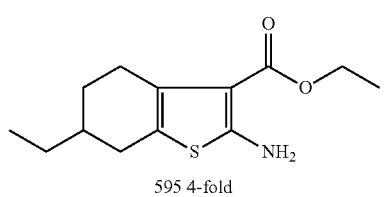
595 4-fold
Plate 7 ODD hits 1.3-1.5 fold
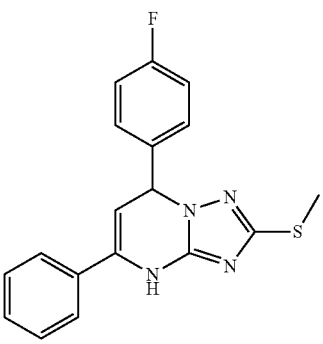
615
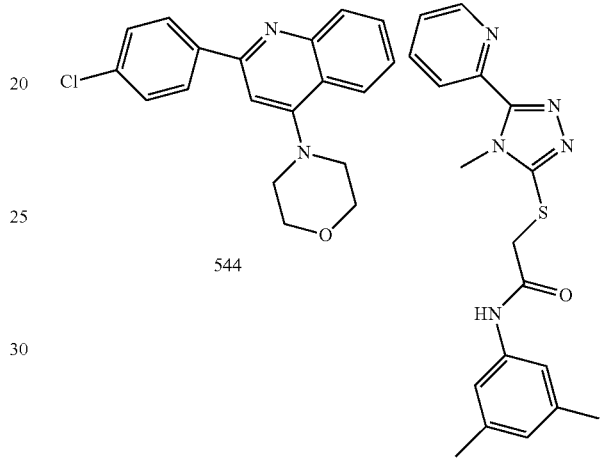
544
540
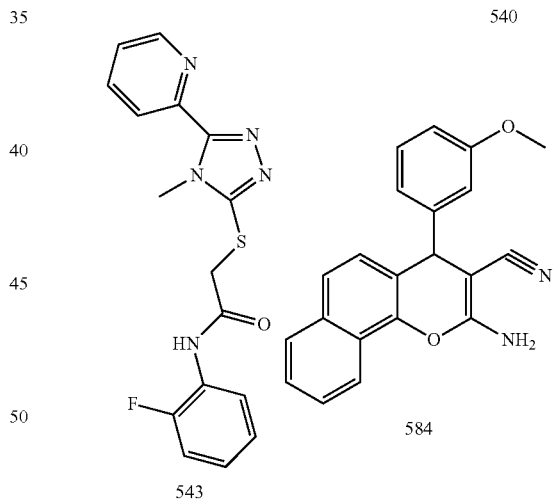
543
584
Plate 8 Nrf2
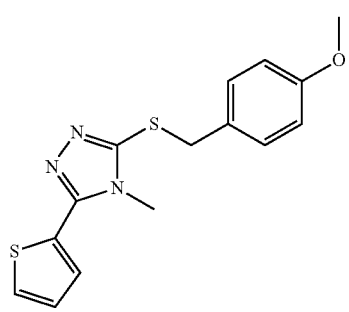
636 2.5 fold -continued
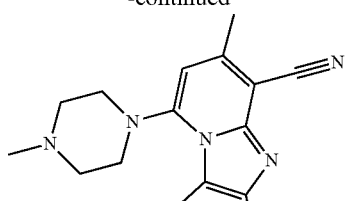
692 3-fold
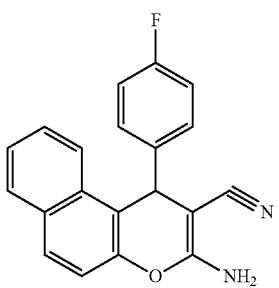
666 4-fold
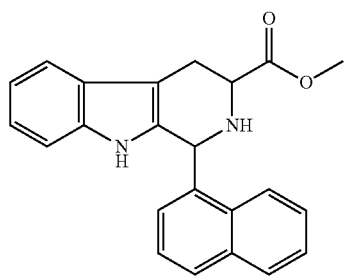
667 1.5 fold
Plate 9 ODD 1.3-1.5 fold
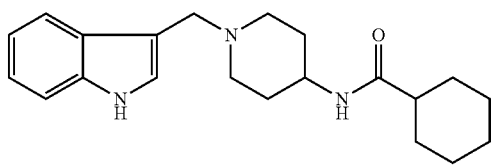
705
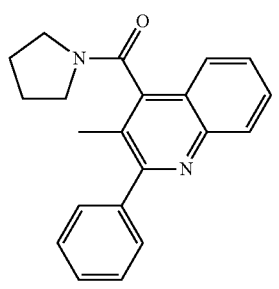
771
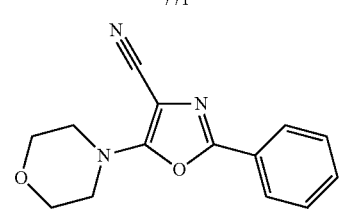
746
-continued
No hits for Nrf2
Plates 11, 12 no hits for both reporters
Plate 10
ODD hits 1.2-fold & Nrf2 >3 fold
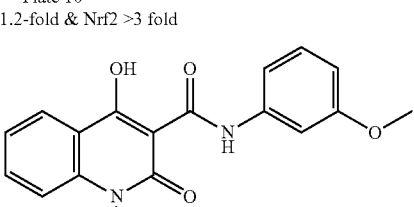
842
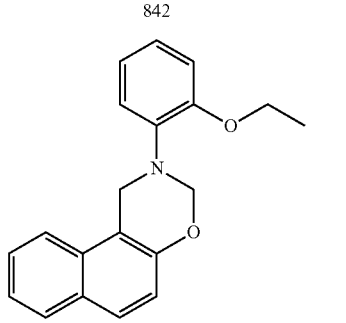
799
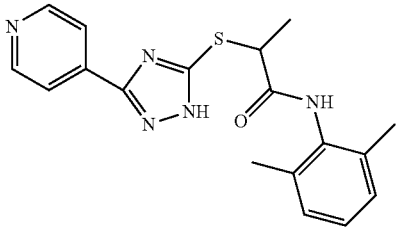
861
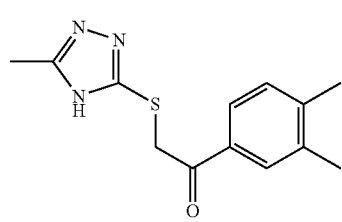
864
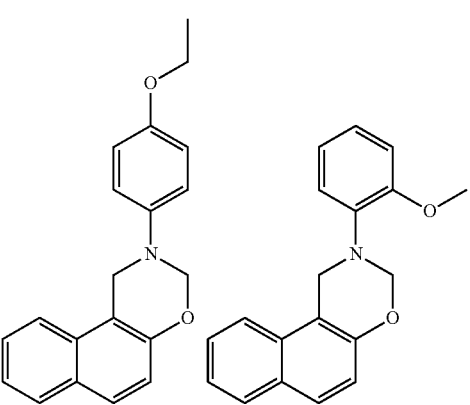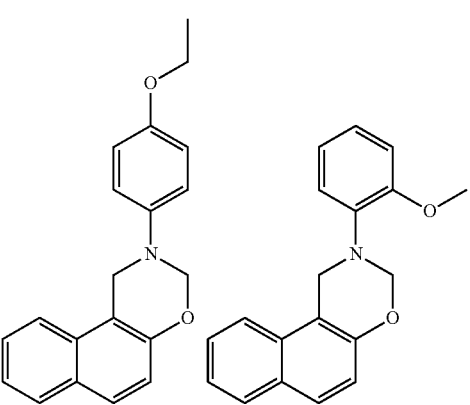
809 1.5-fold    815

-continued
Plate 13 Nrf2 2 hits, no hits for ODD
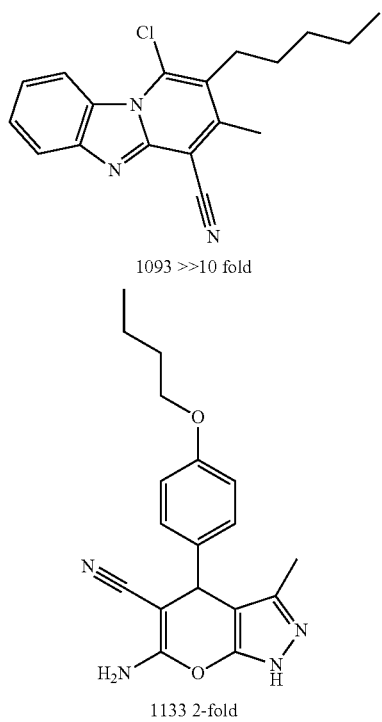
1093 >>10 fold
1133 2-fold
Plate 14 no hits
Plate 15
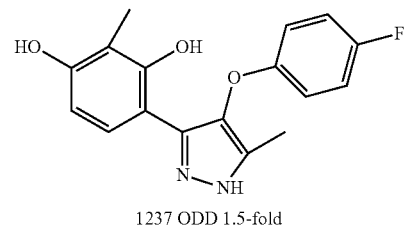
1237 ODD 1.5-fold
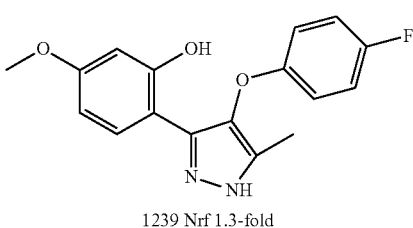
1239 Nrf 1.3-fold
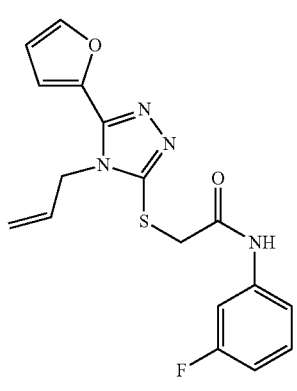
1301 ODD 1.4-fold
-continued
Plate 16 ODD hits 1.5-fold
(no Nrf2 hits)
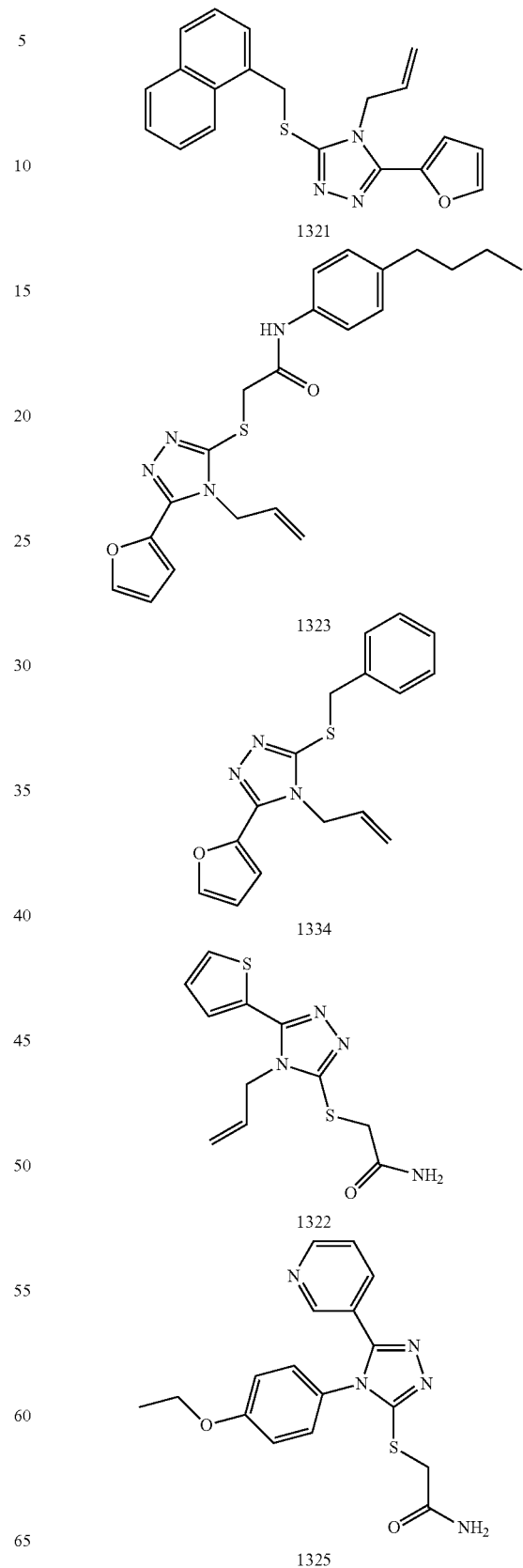
1321
1323
1334
1322
1325

65
-continued
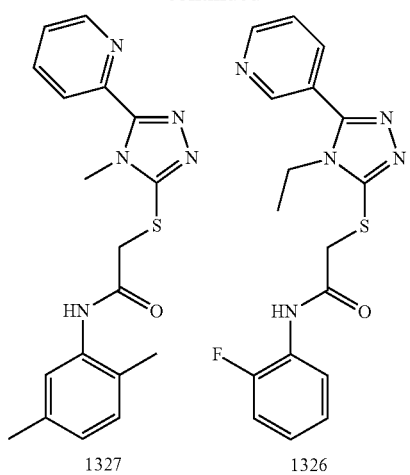
1327    1326
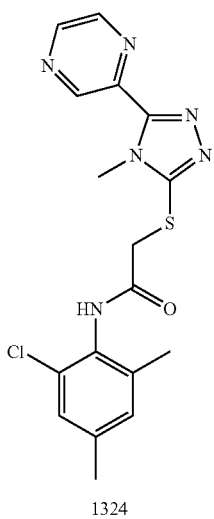
1324
pyrazolo[1,5-a]pyrimidines:
library contains >20 compounds
All others barely active, SAR in progress
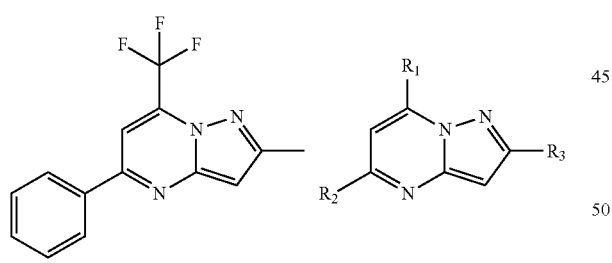
203 1.6-fold
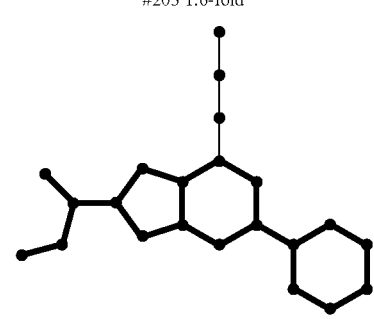
197
66
-continued
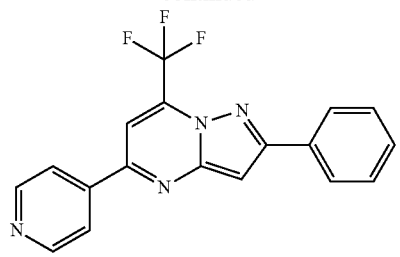
9A2: 2473 4.2-fold
>10-fold cherry pick
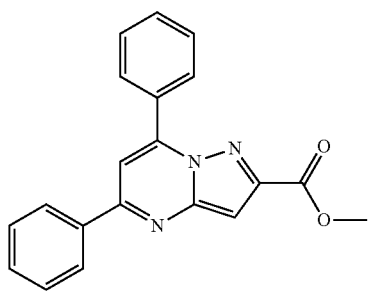
3E#: 197 2-fold
>3.5-fold cherry pick
Active Pyrroles not toxic
up to 40 uM
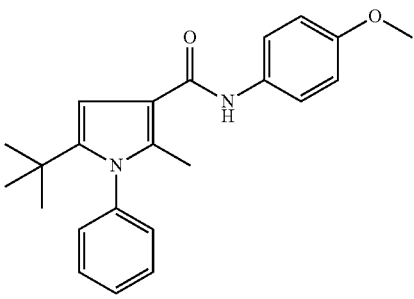
14F1: 2910 7-fold
>30-fold cherry pick
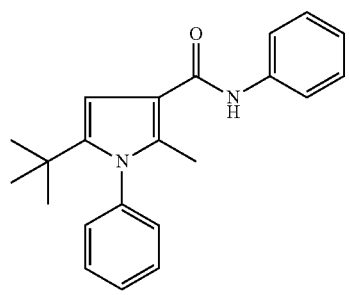
7B4: 2314 12.3-fold
30-fold cherry pick

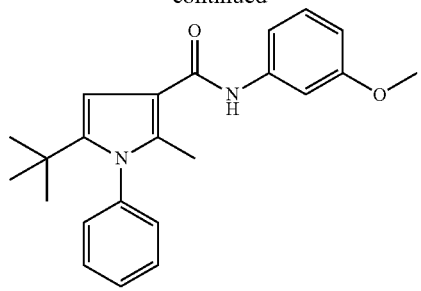
7D4: 2316 12-fold
34-fold cherry pick
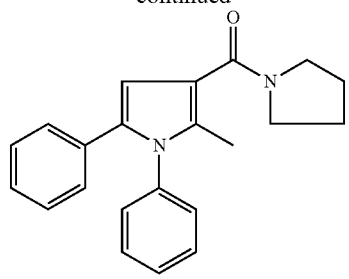
2300
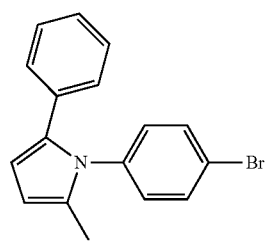
1413 17H1 5.2-fold
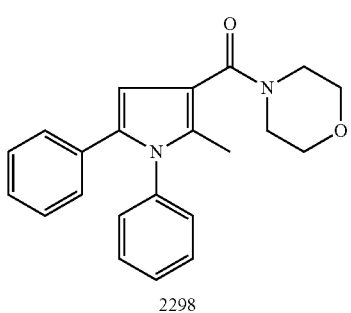
2298
Thienopyrimidines:
The library contains >20,
others barely work
SAR in progress
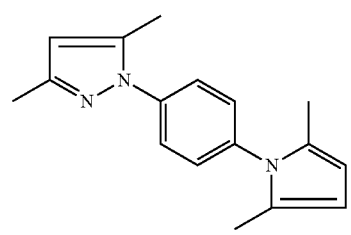
422 2.5-fold
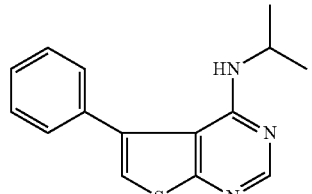
3966 2.4-fold
10-fold cherry pick
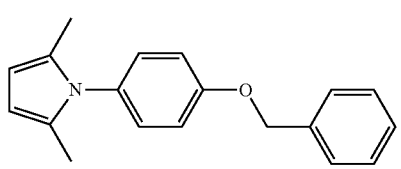
1634 2.1-fold
3-fold cherry pick
Not active pyrroles, SAR in progress
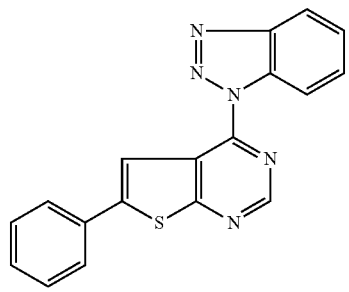
4476 2-fold
<2-fold cherry pick
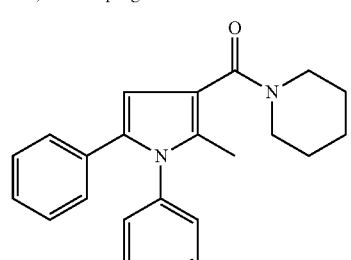
2303
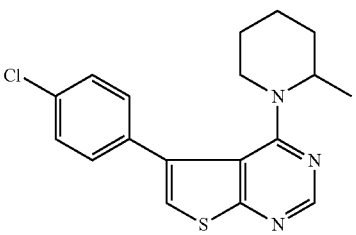
4477 2.1-fold
confirmed Interesting singletones
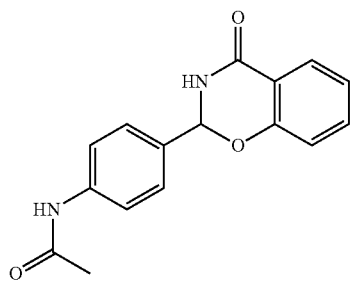
4746 3.5-fold
16-fold cherry pick
Benzopyrazoloxazines
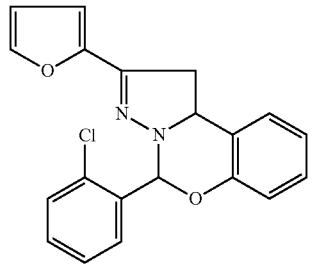
4589 2.1-fold
1.5-fold cherry pick
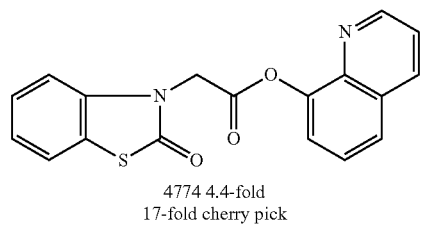
4774 4.4-fold
17-fold cherry pick
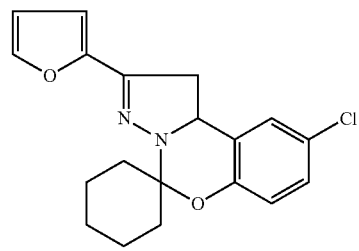
4602 2.2-f
2.4-fold cherry pick
2,3-dihydro-1H-naphtho[1,2-e][1,3]oxazine
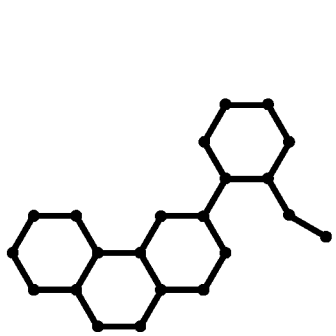
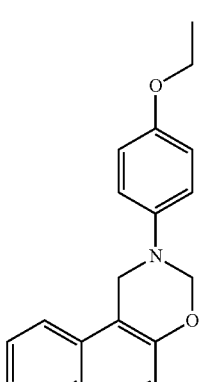
10A3: #809 1.5-fold
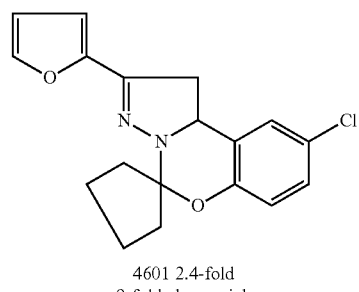
4601 2.4-fold
9-fold cherry pick
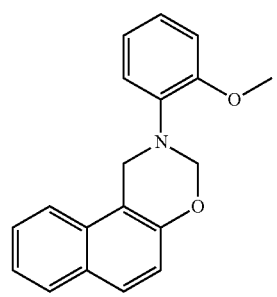
10G3: #815 2.5-fold
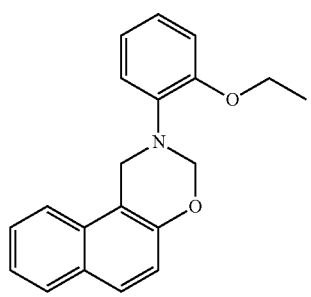
10G1: #799 2.1-fold
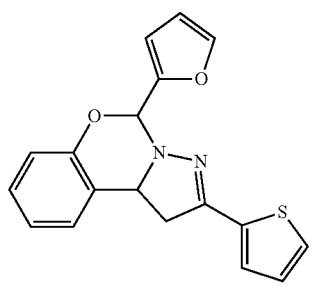
3627 4.3-fold
7-fold cherry pick, toxic
1,10b-dihydrospiro[benzo[e]pyrazolo[1,5-c][1,3]oxazine-5,1'-cyclohexane]

8-Thioquinolines
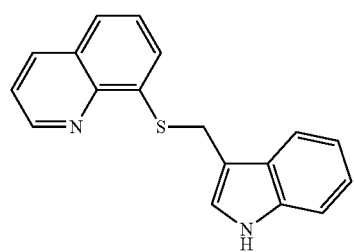
New_ASDI_ID
650,008,080
164
Nrf2 >20-fold
ODD 2 fold
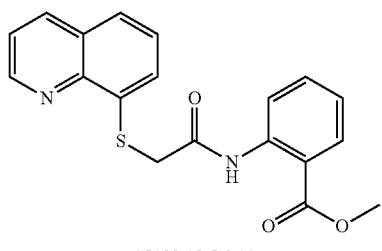
5133 13.5 fold
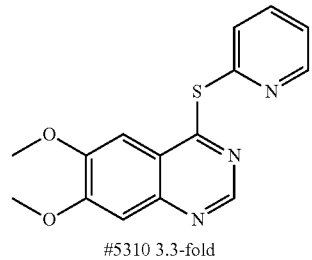
5310 3.3-fold
Zn chelators
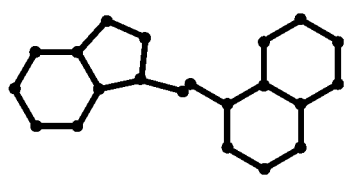
Quinolines
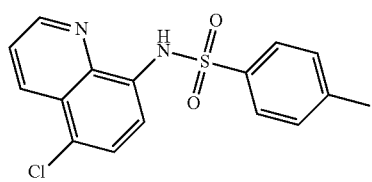
4C2: 2035 26.4-fold
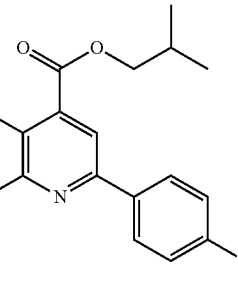
548 3-fold
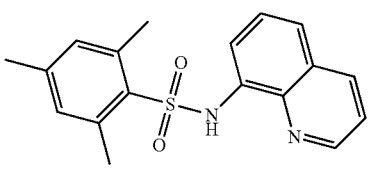
4215 7.9-fold
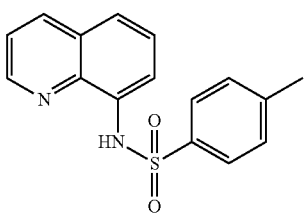
3893 2.1-fold
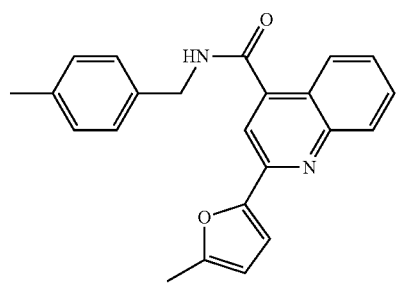
8C3: 2395 2-fold
Arylsulfoxides
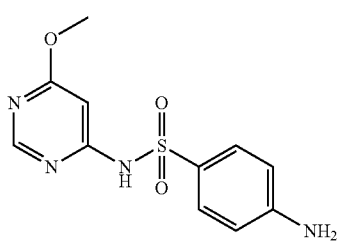
3A1 #1937 3.2-fold
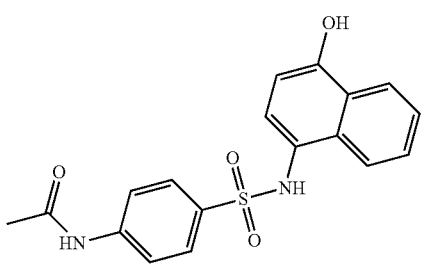
20B9: 3498 4.13-fold -continued
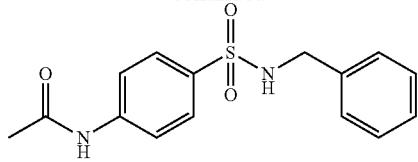
3442 2-fold
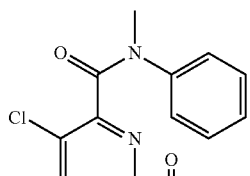
4434 10.2-f
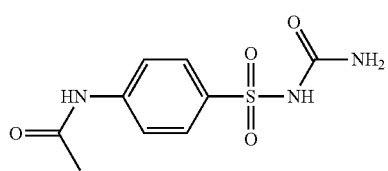
618 2.1-fold
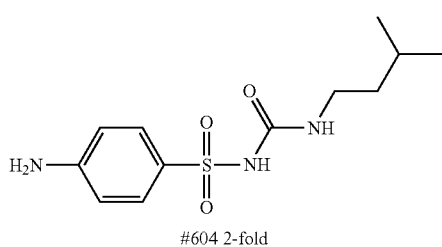
604 2-fold
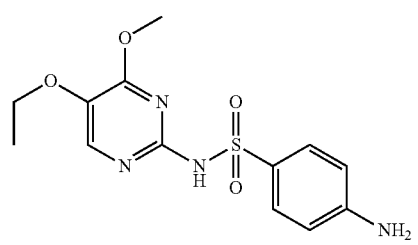
2435
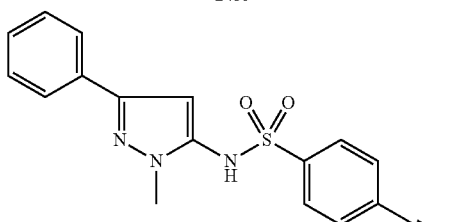
3937 3.5-fold
-continued
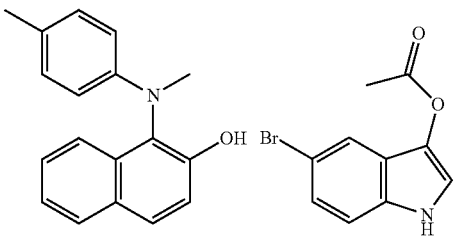
1666 19B11 3-fold
20-fold cherry pick
Does not pass Baell filter
4229 10.5-fold
Michael acceptor motifs
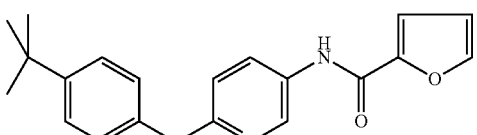
5284 4.1-fold
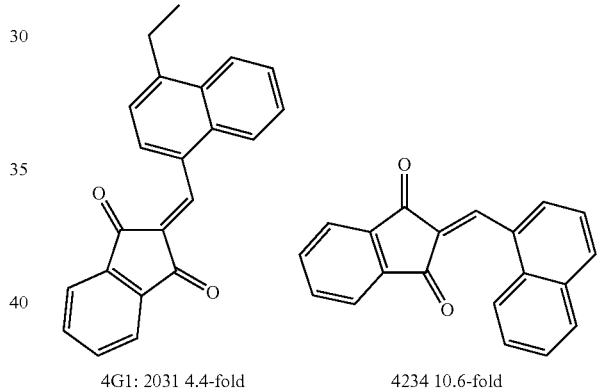
4G1: 2031 4.4-fold              4234 10.6-fold
4,7-dihydro-[1,2,4]triazolo[1,5-a]pyrimidine
Library contains >10 analogs, others almost inactive
Group ArCF3 likely activates double bond: toxic > 20 uM
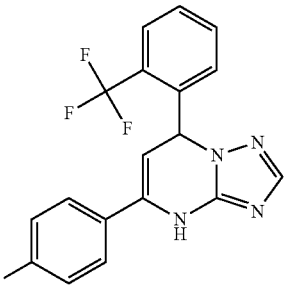
4417 19.8-fold
28-fold cherry pick

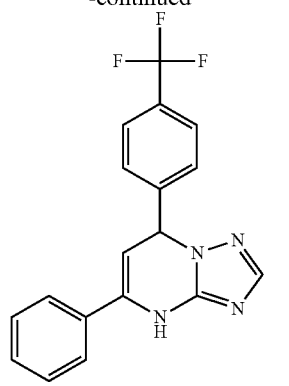
4412 10-fold
13-fold cherry pick
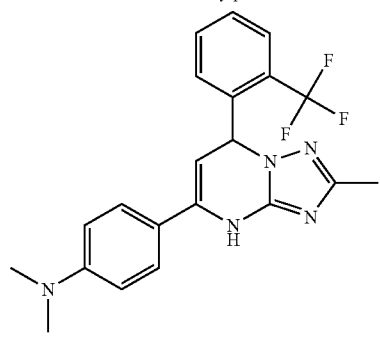
4414 4.3-fold
confirmed
4-hydroxyquinolin-2(1H)-ones
contain Michael motif plus OH-group
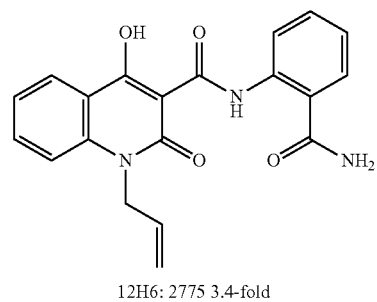
12H6: 2775 3.4-fold
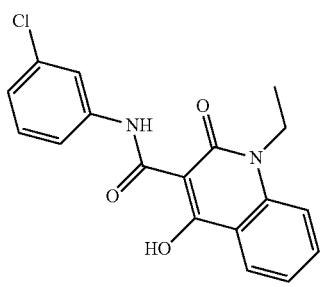
20D10: 3508 2-fold
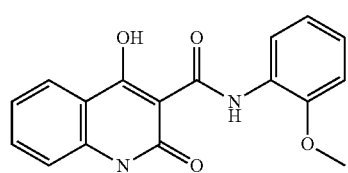
19B4: 3370 2.84-fold
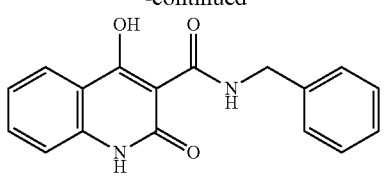
19G3: 3367 2.3-fold
Thiofenes
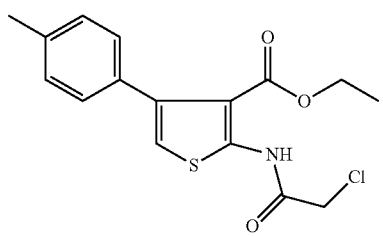
20A7: 3481 6.4-fold
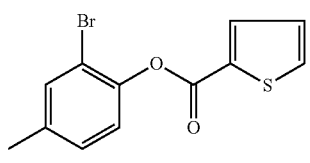
5451 6.3-fold
2-cyclic Thiofenes
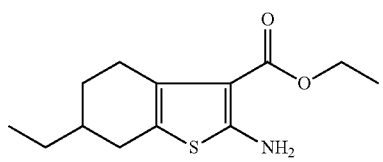
595 5.3-fold
Tricyclic thiophenes
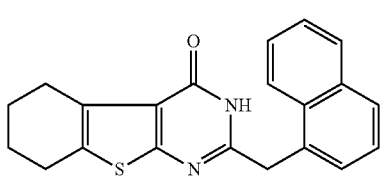
3698 3-fold
Thienopyrimidinones:
Contain Michael motif
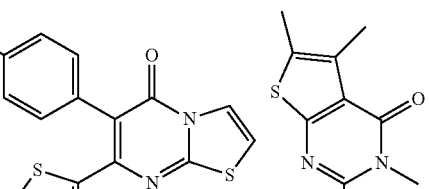
4426 13.5-f
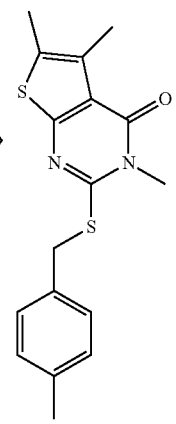
18H4: 3288 3.6-fold

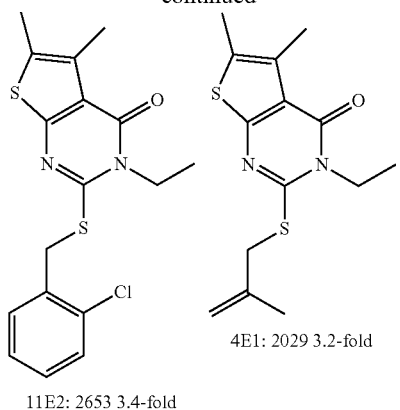
11E2: 2653 3.4-fold     4E1: 2029 3.2-fold
Thiazoles, weak
hits except for:
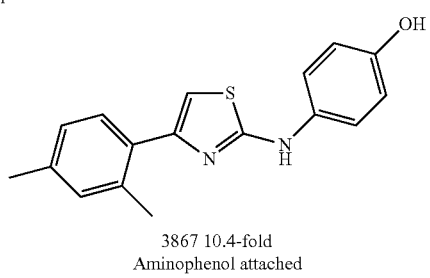
3867 10.4-fold
Aminophenol attached
Isoxazoles: poor hits
except for
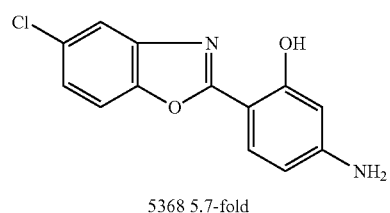
5368 5.7-fold
Benzothiazoles: poor hits
except for
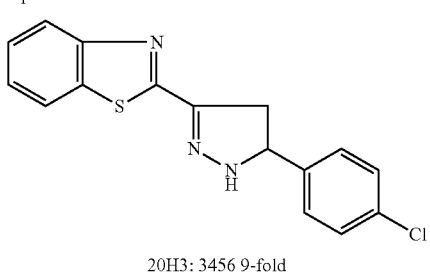
20H3: 3456 9-fold
Triazole sulfides:
>20 hits at 2-3 fold activation,
no SAR observed, non-specific
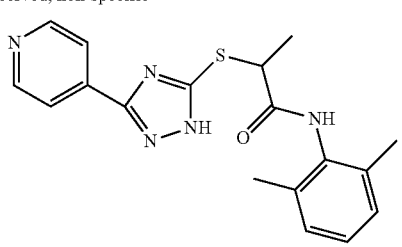
1H-1,2,4-triazole
861 2-fold
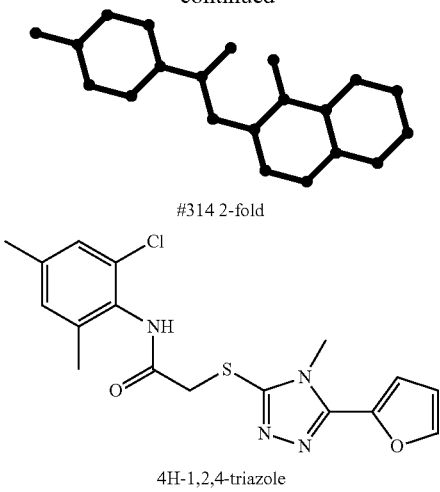
314 2-fold
4H-1,2,4-triazole
636 2-fold
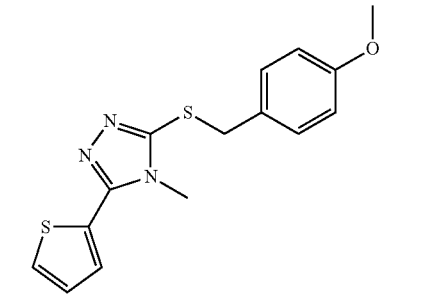
8H1: 2384 2.6-fold
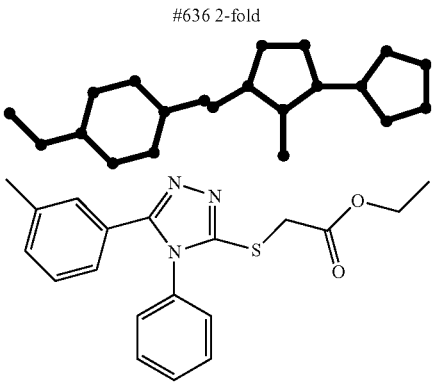
586 4.5-fold
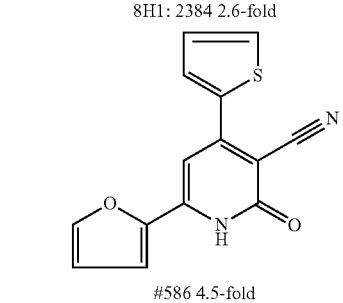
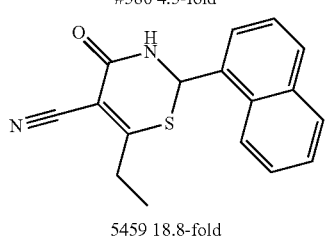
5459 18.8-fold -continued
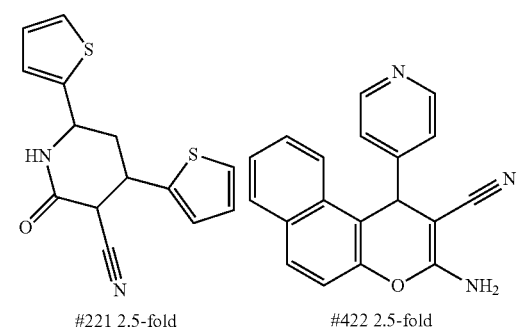
221 2.5-fold   #422 2.5-fold
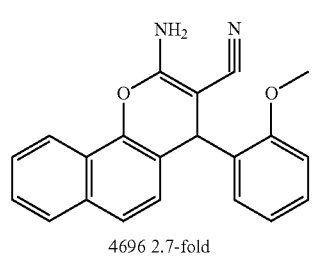
4696 2.7-fold
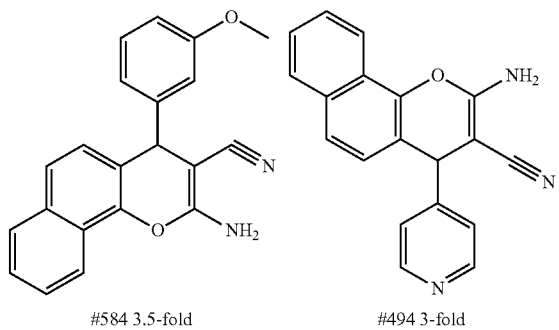
584 3.5-fold   #494 3-fold
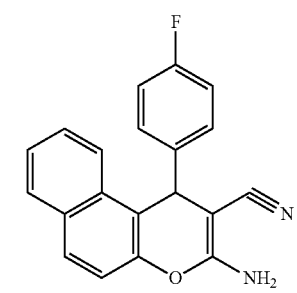
666 3.8-fold
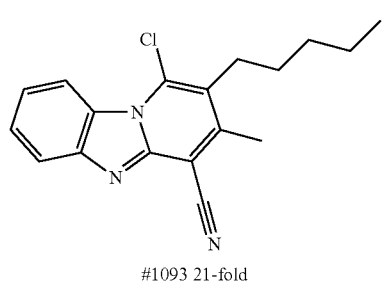
1093 21-fold
-continued
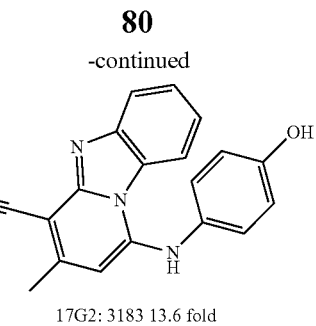
17G2: 3183 13.6 fold
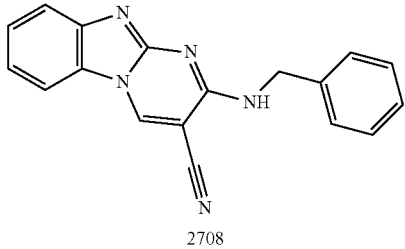
2708
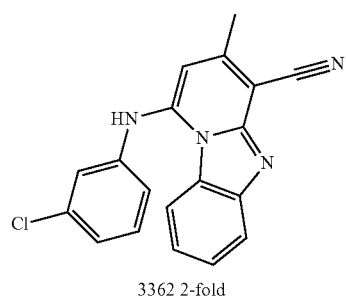
3362 2-fold
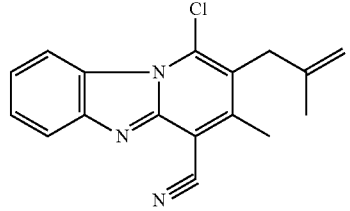
5383 9.1-fold
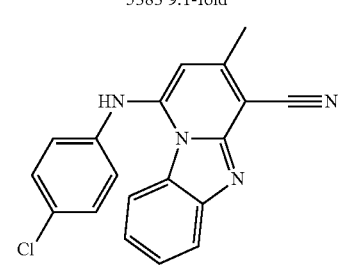
2259 2.1-fold
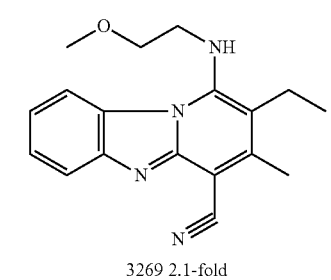
3269 2.1-fold

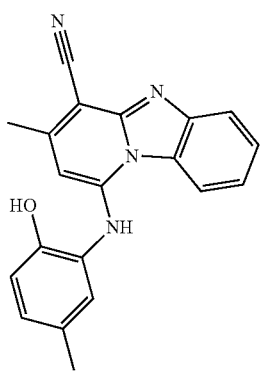
3382 3.1-fold
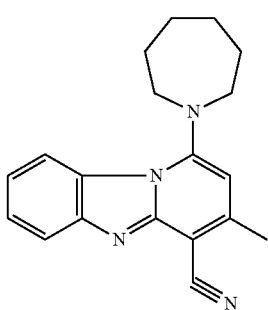
1649 19A9 2.8-fold
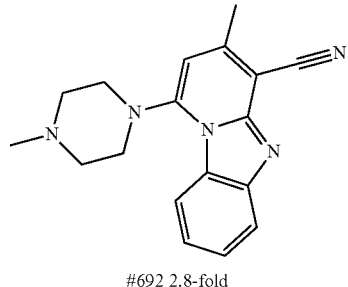
692 2.8-fold
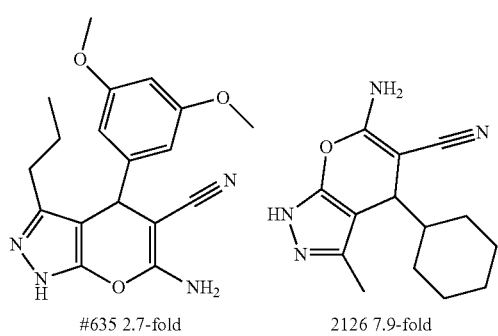
635 2.7-fold     2126 7.9-fold
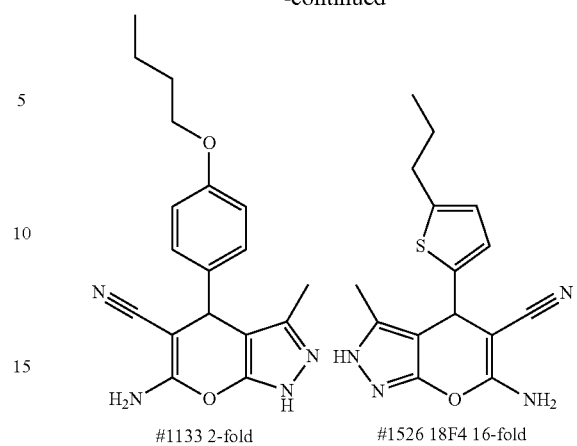
1133 2-fold     #1526 18F4 16-fold
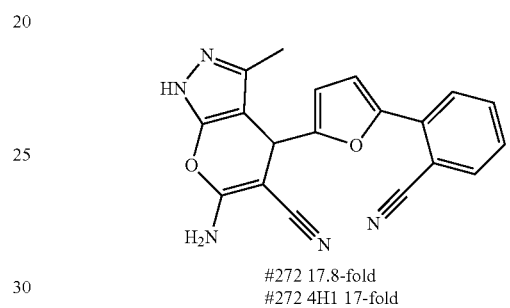
272 17.8-fold
272 4H1 17-fold
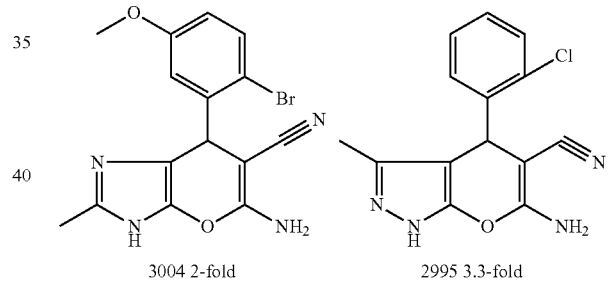
3004 2-fold     2995 3.3-fold
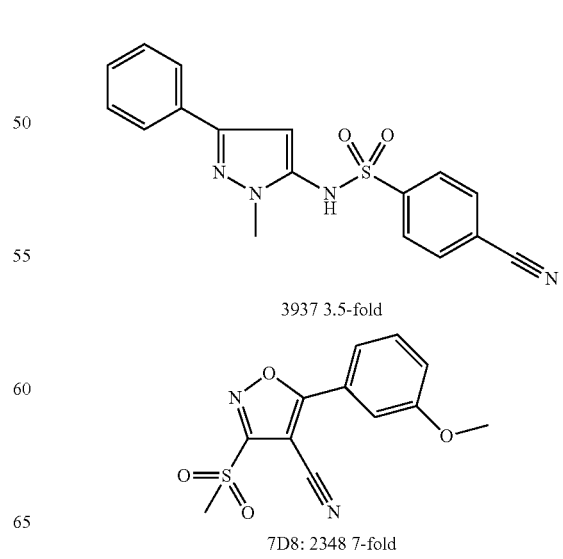
3937 3.5-fold
7D8: 2348 7-fold -continued
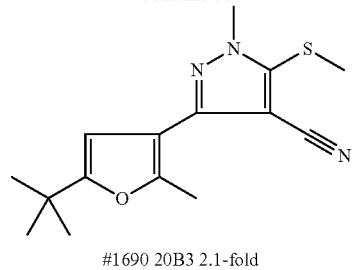
1690 20B3 2.1-fold
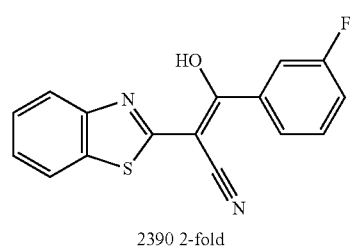
2390 2-fold
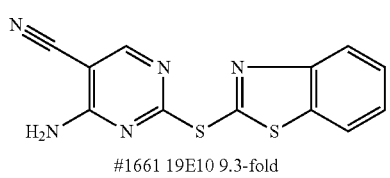
1661 19E10 9.3-fold
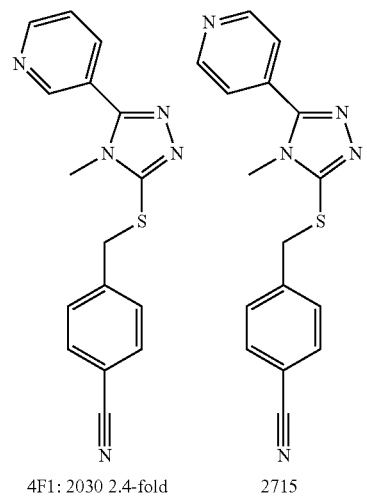
4F1: 2030 2.4-fold        2715
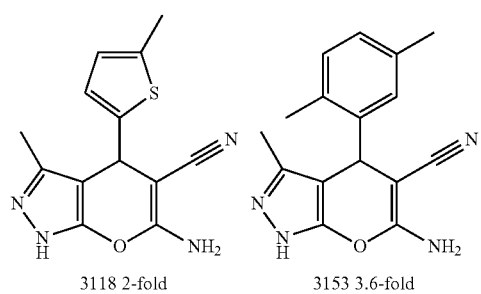
3118 2-fold          3153 3.6-fold
-continued
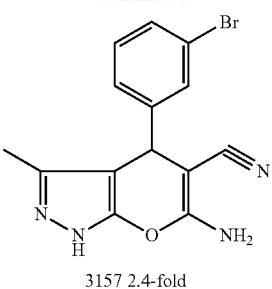
3157 2.4-fold
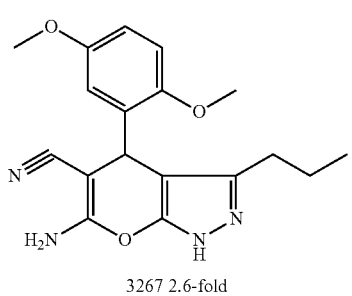
3267 2.6-fold
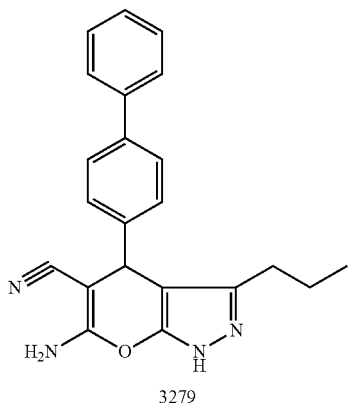
3279
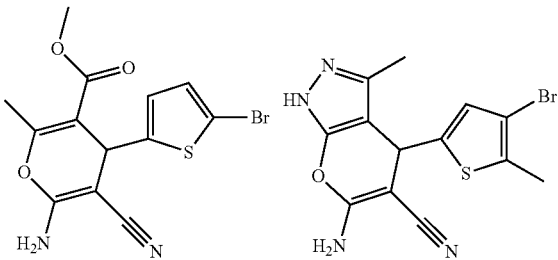
3150 3.1-fold          3793 5.8-fold
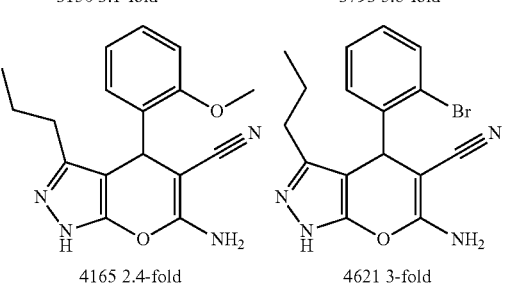
4165 2.4-fold          4621 3-fold

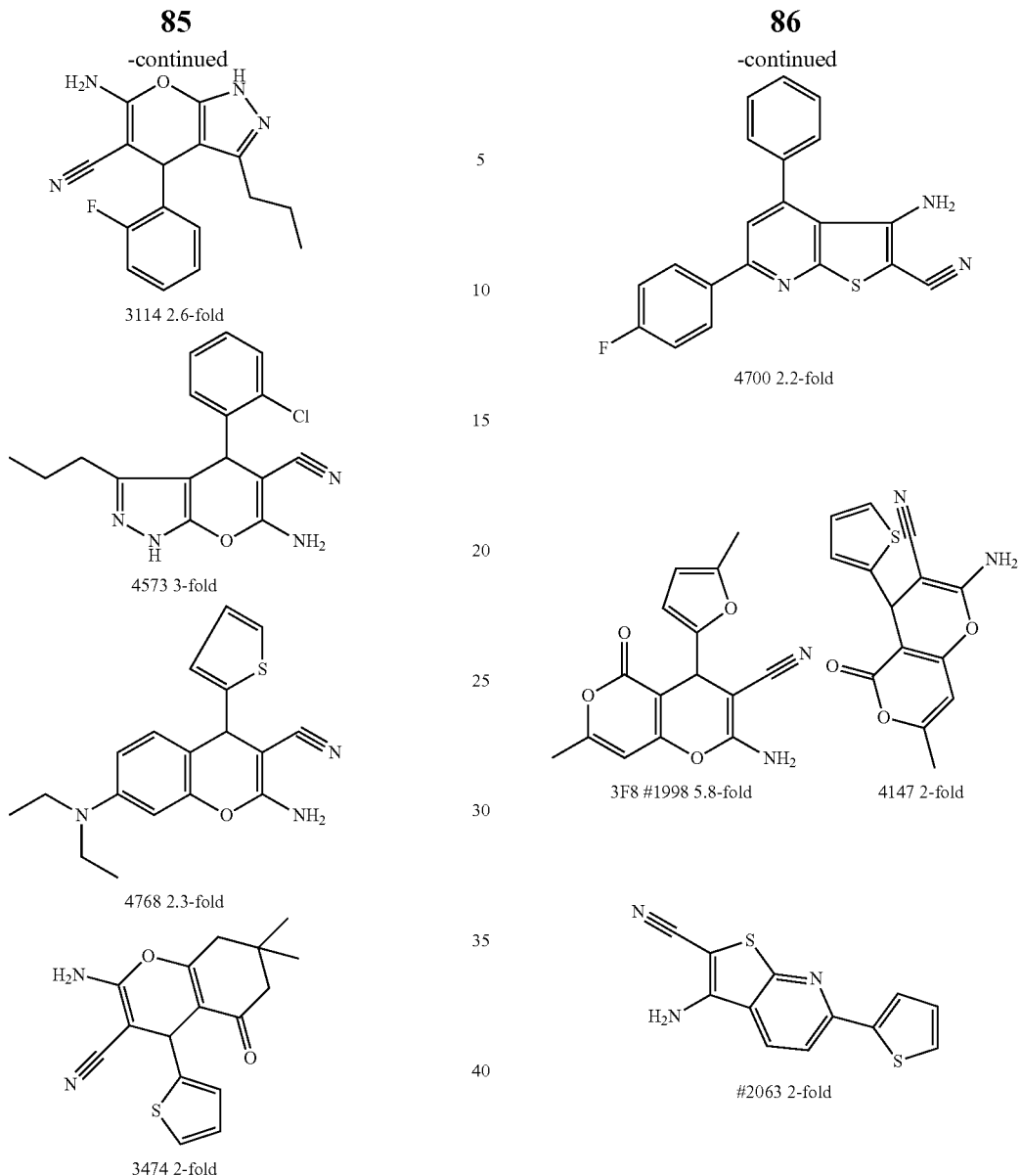

Sequence Information

Human NRF2 Nucleotide and amino acid sequences (SEQ ID NOS: 4-5)
(DNA and corresponding amino acids shown in bold and underline
were used to make the NEH2 construct)
```
DNA: CAGGGCCGCCGTCGGGGAGCCCCAACACACGGTCCACAGCTCATCATGATG
+1:  Q  G  R  R  R  G  A  P  T  H  G  P  Q  L  I  M  M DNA: GACTTGGAGCTGCCGCCGCCGGGACTCCCGTCCCAGCAGGACATGGATTTG
+1:  D  L  E  L  P  P  P  G  L  P  S  Q  Q  D  M  D  L DNA: ATTGACATACTTTGGAGGCAAGATATAGATCTTGGAGTAAGTCGAGAAGTA
+1:  I  D  I  L  W  R  Q  D  I  D  L  G  V  S  R  E  V DNA: TTTGACTTCAGTCAGCGACGGAAAGAGTATGAGCTGGAAAAACAGAAAAAA
+1:  F  D  F  S  Q  R  R  K  E  Y  E  L  E  K  Q  K  K DNA: CTTGAAAAGGAAAGACAAGAACAACTCCAAAAGGAGCAAGAGAAAGCCTTT
+1:  L  E  K  R  Q  E  Q  L  Q  K  E  Q  E  K  A  F DNA: TTCGCTCAGTTACAACTAGATGAAGAGACAGGTGAATTTCTCCCAATTCAG
+1:  F  A  Q  L  Q  L  D  E  E  T  G  E  F  L  P  I  Q DNA: CCAGCCCAGCACATCCAGTCAGAAACCAGTGGATCTGCCAACTACTCCCAG
+1:  P  A  Q  H  I  Q  S  E  T  S  G  S  A  N  Y  S  Q
```

-continued

```
DNA: GTTGCCCACATTCCCAAATCAGATGCTTTGTACTTTGATGACTGCATGCAG
 +1: V   A   H   I   P   K   S   D   A   L   Y   F   D   D   C   M   Q

DNA: CTTTTGGCGCAGACATTCCCGTTTGTAGATGACAATGAGGTTTCTTCGGCT
 +1: L   L   A   Q   T   F   P   F   V   D   D   N   E   V   S   S   A

DNA: ACGTTTCAGTCACTTGTTCCTGATATTCCCGGTCACATCGAGAGCCCAGTC
 +1: T   F   Q   S   L   V   P   D   I   P   G   H   I   E   S   P   V

DNA: TTCATTGCTACTAATCAGGCTCAGTCACCTGAAACTTCTGTTGCTCAGGTA
 +1: F   I   A   T   N   Q   A   Q   S   P   E   T   S   V   A   Q   V

DNA: GCCCCTGTTGATTTAGACGGTATGCAACAGGACATTGAGCAAGTTTGGGAG
 +1: A   P   V   D   L   D   G   M   Q   Q   D   I   E   Q   V   W   E

DNA: GAGCTATTATCCATTCCTGAGTTACAGTGTCTTAATATTGAAATGACAAG
 +1: E   L   L   S   I   P   E   L   Q   C   L   N   I   E   N   D   K

DNA: CTGGTTGAGACTACCATGGTTCCAAGTCCAGAAGCCAAACTGACAGAAGTT
 +1: L   V   E   T   T   M   V   P   S   P   E   A   K   L   T   E   V

DNA: GACAATTATCATTTTTACTCATCTATACCCTCAATGGAAAAAGAAGTAGGT
 +1: D   N   Y   H   F   Y   S   S   I   P   S   M   E   K   E   V   G

DNA: AACTGTAGTCCACATTTTCTTAATGCTTTTGAGGATTCCTTCAGCAGCATC
 +1: N   C   S   P   H   F   L   N   A   F   E   D   S   F   S   S   I

DNA: CTCTCCACAGAAGACCCCAACCAGTTGACAGTGAACTCATTAAATTCAGAT
 +1: L   S   T   E   D   P   N   Q   L   T   V   N   S   L   N   S   D

DNA: GCCACAGTCAACACAGATTTTGGTGATGAATTTTATTCTGCTTTCATAGCT
 +1: A   T   V   N   T   D   E   G   D   E   F   Y   S   A   F   I   A

DNA: GAGCCCAGTATCAGCAACAGCATGCCCTCACCTGCTACTTTAAGCCATTCA
 +1: E   P   S   I   S   N   S   M   P   S   P   A   T   L   S   H   S

DNA: CTCTCTGAACTTCTAAATGGGCCCATTGATGTTTCTGATCTATCACTTTGC
 +1: L   S   E   L   L   N   G   P   I   D   V   S   D   L   S   L   C

DNA: AAAGCTTTCAACCAAAACCACCCTGAAAGCACAGCAGAATTCAATGATTCT
 +1: K   A   F   N   Q   N   H   P   E   S   T   A   E   F   N   D   S

DNA: GACTCCGGCATTTCACTAAACACAAGTCCCAGTGTGGCATCACCAGAACAC
 +1: D   S   G   I   S   L   N   T   S   P   S   V   A   S   P   E   H

DNA: TCAGTGGAATCTTCCAGCTATGGAGACACACTACTTGGCCTCAGTGATTCT
 +1: S   V   E   S   S   S   Y   G   D   T   L   L   G   L   S   D   S

DNA: GAAGTGGAAGAGCTAGATAGTGCCCCTGGAAGTGTCAAACAGAATGGTCCT
 +1: E   V   E   E   L   D   S   A   P   G   S   V   K   Q   N   G   P

DNA: AAAACACCAGTACATTCTTCTGGGGATATGGTACAACCCTTGTCACCATCT
 +1: K   T   P   V   H   S   S   G   D   M   V   Q   P   L   S   P   S

DNA: CAGGGGCAGAGCACTCACGTGCATGATGCCCAATGTGAGAACACACCAGAG
 +1: Q   G   Q   S   T   H   V   H   D   A   Q   C   E   N   T   P   E

DNA: AAAGAATTGCCTGTAAGTCCTGGTCATCGGAAAACCCCATTCACAAAAGAC
 +1: K   E   L   P   V   S   P   G   H   R   K   T   P   F   T   K   D

DNA: AAACATTCAAGCCGCTTGGAGGCTCATCTCACAAGAGATGAACTTAGGGCA
 +1: K   H   S   S   R   L   E   A   H   L   T   R   D   E   L   R   A

DNA: AAAGCTCTCCATATCCCATTCCCTGTAGAAAAAATCATTAACCTCCCTGTT
 +1: K   A   L   H   I   P   F   P   V   E   K   I   I   N   L   P   V

DNA: GTTGACTTCAACGAAATGATGTCCAAAGAGCAGTTCAATGAAGCTCAACTT
 +1: V   D   F   N   E   M   M   S   K   E   Q   F   N   E   A   Q   L

DNA: GCATTAATTCGGGATATACGTAGGAGGGGTAAGAATAAAGTGGCTGCTCAG
 +1: A   L   I   R   D   I   R   R   A   G   K   N   K   V   A   A   Q

DNA: AATTGCAGAAAAAGAAAACTGGAAAATATAGTAGAACTAGAGCAAGATTTA
 +1: N   C   R   K   R   K   L   E   N   I   V   E   L   E   Q   D   L

DNA: GATCATTTGAAAGATGAAAAAGAAAAATTGCTCAAAGAAAAAGGAGAAAAT
 +1: D   H   L   K   D   E   K   E   K   L   L   K   E   K   G   E   N

DNA: GACAAAAGCCTTCACCTACTGAAAAAACAACTCAGCACCTTATATCTCGAA
 +1: D   K   S   L   H   L   L   K   K   Q   L   S   T   L   Y   L   E
```

```
DNA: GTTTTCAGCATGCTACGTGATGAAGATGGAAAACCTTATTCTCCTAGTGAA
+1:  V  F  S  M  L  R  D  E  D  G  K  A  Y  S  P  S  E

DNA: TACTCCCTGCAGCAAACAAGAGATGGCAATGTTTTCCTTGTTCCCAAAAGT
+1:  Y  S  L  Q  Q  T  R  D  G  N  V  F  L  V  P  K  S

DNA: AAGAAGCCAGATGTTAAGAAAAACTAG
+1:  K  K  P  D  V  K  K  N  *
```

Human NRF2 amino acid sequence (SEQ ID NO: 6), with the NEH2 domain (SEQ ID NO: 11) underlined.

MMDLELPPPGLPSQQDMDLIDILWRQDIDLGVSREVEDFSQRRKEYELEKQKKLEKERQEQLQKEQEKAF

FAQLQLDEETGEFLPIQPAQHIQSETSGSANYSQVAHIPKSDALYFDDCMQLLAQTFPFVDDNEVSSATF

QSLVPDIPGHIESPVFIATNQAQSPETSVAQVAPVDLDGMQQDIEQVWEELLSIPELQCLNIENDKLVET

TMVPSPEAKLTEVDNYHFYSSIPSMEKEVGNCSPHFLNAFEDSFSSILSTEDPNQLTVNSLNSDATVNTD

FGDEFYSAFIAEPSISNSMPSPATLSHSLSELLNGPIDVSDLSLCKAFNQNHPESTAEFNDSDSGISLNT

SPSVASPEHSVESSSYGDTLLGLSDSEVEELDSAPGSVKQNGPKTPVHSSGDMVQPLSPSQGQSTHVHDA

QCENTPEKELPVSPGHRKTPFTKDKHSSRLEAHLTRDELRAKALHIPFPVEKIINLPVVDFNEMMSKEQF

NEAQLALIRDIRRRGKNKVAAQNCRKRKLENIVELEQDLDHLKDEKEKLLKEGENDKSLHLLKKQLSTL

YLEVFSMLRDEDGKPYSPSEYSLQQTRDGNVFLVPKSKKPDVKKN

Mouse Nrf2 (Acession No. NP_035032) (SEQ ID NO: 14), with the NEH2 domain underlined (SEQ ID NO: 15)

```
  1 MMDLELPPPG LQSQQDMDLI DILWRQDIDL GVSREVFDFS QRQKDYELEK QKKLEKERQE

61 QLQKEQEKAF FAQFQLDEET GEFLPIQPAQ HIQTDTSGSA SYSQVAHIPK QDALYFEDCM

121 QLLAETFPFV DDHESLALDI PSHAESSVFT APHQAQSLNS SLEAAMTDLS SIEQDMEQVW

181 QELFSIPELQ CLNTENKQLA DTTAVPSPEA TLTEMDSNYH FYSSISSLEK EVGNCGPHFL

241 HGFEDSFSSI LSTDDASQLT SLDSNPTLNT DFGDEFYSAF IAEPSDGGSM PSSAAISQSL

301 SELLDGTIEG CDLSLCKAFN PKHAEGTMEF NDSDSGISLN TSPSRASPEH SVESSIYGDP

361 PPGFSDSEME ELDSAPGSVK QNGPKAQPAH SPGDTVQPLS PAQGHSAPMR ESQCENTTKK

421 EVPVSPGHQK APFTKDKHSS RLEAHLTRDE LRAKALHIPF PVEKIINLPV DDFNEMMSKE

481 QFNEAQLALI RDIRRRGKNK VAAQNCRKRK LENIVELEQD LGHLKDEREK LLREKGENDR

541 NLHLLKRRLS TLYLEVFSML RDEDGKPYSP SEYSLQQTRD GNVFLVPKSK KPDTKKN
```

Chicken Nrf2 (Accession No. NP_990448) (SEQ ID NO: 16), with the NEH2 domain underlined (SEQ ID NO: 17)

```
  1 MNLIDILWRQ DIDLGARREV FDFSQRQKEY ELEKQKKLEK ERQEQLQKER EKALLAQLVL

61 DEETGEFVPA QPAQRVQSEN AEPPISFSQS TDTSKPEEAL SFDDCMQLLA EAFPFIDDNE

121 ASPAAFQSLV PDQIDSDPVF ISANQTQPPS SPGIVPLTDA ENMQNIEQVW EELLSLPELQ

181 CLNIENDNLA EVSTITSPET KPAEMHNSYD YYNSLPIMRK DVNCGPDFLE NIEGPFSSIL

241 QPDDSSQLNV NSLNNSLTLS SDFCEDFYTN FICAKGDGDT GTTNTISQSL ADILSEPIDL

301 SDFPLWRAFN DDHSGTVPEC NDSDSGISLN ANSSIASPEH SVESSTCGDK TFGCSDSEME

361 DMDSSPGSVP QGNASVYSSR FPDQVLPSVE PGTQTPSLQR MNTPKKDPPA GPGHPKAPFT

421 KDKPSGRLEA HLTRDEQRAK ALQIPFPVEK IINLPVDDFN EMMSKEQFSE AQLALIRDIR

481 RRGKNKVAAQ NCRKRKLENI VELEQDLSHL KDEREKLLKE KGENDKSLRQ MKKQLTTLYI

541 EVFSMLRDED GKSYSPSEYS LQQTRDGNIF LVPKSRKAET KL
```

---

What is claimed is:

1. A nucleic acid construct, comprising a nucleotide sequence which codes for a fusion protein which comprises an Nuclear factor (erythroid-derived 2)-like 2 (Nrf2)-ECH homologous (Neh2) domain linked to a reporter, wherein the Neh2 domain consists of an amino acid sequence having at least 95% identity with SEQ ID NO: 11.

2. The nucleic acid construct of claim 1, wherein the Neh2 domain is the native Neh2 domain of a Nrf2 molecule selected from the group consisting of human Nrf2 and mouse Nrf2.

3. The nucleic acid construct of claim 1, wherein the Neh2 domain consists of amino acids 1-97 of human Nrf2, as set forth in SEQ ID NO: 11.

4. The nucleic acid construct of claim 1, wherein the reporter is selected from the group consisting of luciferase, lactosidase, a green fluorescent protein, a yellow fluorescent protein, cyan fluorescent protein and a red fluorescent protein.

5. The nucleic acid construct of claim 1, wherein said nucleotide sequence encoding the fusion protein is operably linked to a promoter selected from a cytomegalovirus (CMV) promoter or a simian virus 40 (SV40) promoter.

6. An isolated fusion protein which comprises an Nrf2-ECH homologous (Neh2) domain operably linked to a reporter, wherein the Neh2 domain consists of an amino acid sequence having at least 95% identity with SEQ ID NO: 11.

7. The fusion protein of claim 6, wherein the Neh2 domain is the native Neh2 domain of a Nrf2 molecule selected from the group consisting of human Nrf2 and mouse Nrf2.

8. The fusion protein of claim 6, wherein the Neh2 domain consists of amino acids 1-97 of human Nrf2, as set forth in SEQ ID NO: 11.

9. The fusion protein of claim 6, wherein the reporter is selected from the group consisting of luciferase, lactosidase, a green fluorescent protein, a yellow fluorescent protein, cyan fluorescent protein and a red fluorescent protein.

10. A cell comprising the nucleic acid construct of claim 1 or the fusion protein of claim 6.

11. The cell of claim 10, wherein the cell is a human cell line.

12. The nucleic acid construct of claim 1, wherein the Neh2 domain differs from SEQ ID NO: 11 by no more than 3 amino acids and the differences reside outside of the DLG and ETGE (SEQ ID NO: 13) motifs.

* * * * *